US009406892B2

(12) United States Patent
Zeng et al.

(10) Patent No.: US 9,406,892 B2
(45) Date of Patent: Aug. 2, 2016

(54) ORGANIC ELECTROLUMINESCENT MATERIALS AND DEVICES

(71) Applicant: Universal Display Corporation, Ewing, NJ (US)

(72) Inventors: Lichang Zeng, Lawrenceville, NJ (US); Scott Joseph, Ewing, NJ (US); Walter Yeager, Yardley, PA (US); Alexey Borisovich Dyatkin, Ambler, PA (US); Chuanjun Xia, Lawrenceville, NJ (US)

(73) Assignee: UNIVERSAL DISPLAY CORPORATION, Ewing, NJ (US)

( * ) Notice: Subject to any disclaimer, the term of this patent is extended or adjusted under 35 U.S.C. 154(b) by 58 days.

(21) Appl. No.: 14/591,555

(22) Filed: Jan. 7, 2015

(65) Prior Publication Data
US 2016/0197285 A1    Jul. 7, 2016

(51) Int. Cl.
*H01L 51/00* (2006.01)
*C07D 405/10* (2006.01)
(Continued)

(52) U.S. Cl.
CPC .......... *H01L 51/0067* (2013.01); *C07D 405/10* (2013.01); *C07D 409/10* (2013.01);
(Continued)

(58) Field of Classification Search
CPC ............ H01L 51/0052; H01L 51/0058; H01L 51/0073; H01L 51/0074; H01L 51/5024; H01L 51/5072; H01L 51/5096; H01L 51/5206; H01L 51/5221
See application file for complete search history.

(56) References Cited

U.S. PATENT DOCUMENTS 4,769,292 A    9/1988    Tang et al.
5,061,569 A    10/1991    VanSlyke et al.
(Continued)

FOREIGN PATENT DOCUMENTS

EP    0650955    5/1995
EP    1725079    11/2006
(Continued)

OTHER PUBLICATIONS

Adachi, Chihaya et al., "Organic Electroluminescent Device Having a Hole Conductor as an Emitting Layer," Appl. Phys. Lett., 55(15): 1489-1491 (1989).
(Continued)

*Primary Examiner* — Mamadou Diallo
(74) *Attorney, Agent, or Firm* — Duane Morris LLP

(57) ABSTRACT

A compound having a structure of Formula I:

Formula I, is disclosed. In the structure of Formula I: X is selected from a group consisting of O, S and Se; $G^2$ and $G^3$ are each independently selected from benzene, biphenyl, fluorene, naphthalene, phenanthrene, triphenylene, dibenzofuran, dibenzothiophene, dibenzoselenophene, pyridine, pyrimidine, quinoline, isoquinoline, phenanthroline, azafluorene, and combinations thereof; L is selected from phenyl, biphenyl, terphenyl and pyridine, and combinations thereof; $G^2$, $G^3$ and L are each optionally further substituted with one or more unfused substituents; $R^1$, $R^2$, and each $R^3$, $R^4$, $R^5$ and $R^6$ are an unfused substituent selected from hydrogen, deuterium, alkyl, alkoxyl, cycloalkyl, cycloalkoxyl, halogen, nitro, nitrile, silyl, benzene, biphenyl, terphenyl, pyridine, and combinations thereof; and $R^1$ and $R^2$ are optionally joined to form a ring. Formulations and devices, such as an OLEDs, that include the compound of Formula I, and, optionally a co-host, are also described.

20 Claims, 3 Drawing Sheets

Formula I

(51) Int. Cl.
*C07D 409/10* (2006.01)
*H01L 51/52* (2006.01)
*H01L 51/50* (2006.01)

(52) U.S. Cl.
CPC ........ *H01L51/0052* (2013.01); *H01L 51/0058* (2013.01); *H01L 51/0073* (2013.01); *H01L 51/0074* (2013.01); *H01L 51/5024* (2013.01); *H01L 51/5072* (2013.01); *H01L 51/5096* (2013.01); *H01L 51/5206* (2013.01); *H01L 51/5221* (2013.01); *H01L 2251/562* (2013.01)

(56) References Cited

U.S. PATENT DOCUMENTS

| | | | |
|---|---|---|---|
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,844,363 | A | 12/1998 | Gu et al. |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,528,187 | B1 | 3/2003 | Okada |
| 6,687,266 | B1 | 2/2004 | Ma et al. |
| 6,821,643 | B1 | 11/2004 | Hu et al. |
| 6,835,469 | B2 | 12/2004 | Kwong et al. |
| 6,921,915 | B2 | 7/2005 | Takiguchi et al. |
| 7,087,321 | B2 | 8/2006 | Kwong et al. |
| 7,090,928 | B2 | 8/2006 | Thompson et al. |
| 7,154,114 | B2 | 12/2006 | Brooks et al. |
| 7,250,226 | B2 | 7/2007 | Tokito et al. |
| 7,279,704 | B2 | 10/2007 | Walters et al. |
| 7,332,232 | B2 | 2/2008 | Ma et al. |
| 7,338,722 | B2 | 3/2008 | Thompson et al. |
| 7,393,599 | B2 | 7/2008 | Thompson et al. |
| 7,396,598 | B2 | 7/2008 | Takeuchi et al. |
| 7,431,968 | B1 | 10/2008 | Shtein et al. |
| 7,445,855 | B2 | 11/2008 | Mackenzie et al. |
| 7,534,505 | B2 | 5/2009 | Lin et al. |
| 2002/0034656 | A1 | 3/2002 | Thompson et al. |
| 2002/0134984 | A1 | 9/2002 | Igarashi |
| 2002/0158242 | A1 | 10/2002 | Son et al. |
| 2003/0138657 | A1 | 7/2003 | Li et al. |
| 2003/0151042 | A1 | 8/2003 | Hueschen |
| 2003/0152802 | A1 | 8/2003 | Tsuboyama et al. |
| 2003/0175553 | A1 | 9/2003 | Thompson et al. |
| 2003/0230980 | A1 | 12/2003 | Forrest et al. |
| 2004/0036077 | A1 | 2/2004 | Ise |
| 2004/0038075 | A1* | 2/2004 | Wang ............... C08G 61/122 428/690 |
| 2004/0137267 | A1 | 7/2004 | Igarashi et al. |
| 2004/0137268 | A1 | 7/2004 | Igarashi et al. |
| 2004/0174116 | A1 | 9/2004 | Lu et al. |
| 2005/0025993 | A1 | 2/2005 | Thompson et al. |
| 2005/0112407 | A1 | 5/2005 | Ogasawara et al. |
| 2005/0238919 | A1 | 10/2005 | Ogasawara |
| 2005/0244673 | A1 | 11/2005 | Satoh et al. |
| 2005/0260441 | A1 | 11/2005 | Thompson et al. |
| 2005/0260449 | A1 | 11/2005 | Walters et al. |
| 2006/0008670 | A1 | 1/2006 | Lin et al. |
| 2006/0202194 | A1 | 9/2006 | Jeong et al. |
| 2006/0240279 | A1 | 10/2006 | Adamovich et al. |
| 2006/0251923 | A1 | 11/2006 | Lin et al. |
| 2006/0263635 | A1 | 11/2006 | Ise |
| 2006/0280965 | A1 | 12/2006 | Kwong et al. |
| 2007/0190359 | A1 | 8/2007 | Knowles et al. |
| 2007/0278938 | A1 | 12/2007 | Yabunouchi et al. |
| 2008/0015355 | A1 | 1/2008 | Schafer et al. |
| 2008/0018221 | A1 | 1/2008 | Egen et al. |
| 2008/0106190 | A1 | 5/2008 | Yabunouchi et al. |
| 2008/0124572 | A1 | 5/2008 | Mizuki et al. |
| 2008/0220265 | A1 | 9/2008 | Xia et al. |
| 2008/0297033 | A1 | 12/2008 | Knowles et al. |
| 2009/0008605 | A1 | 1/2009 | Kawamura et al. |
| 2009/0009065 | A1 | 1/2009 | Nishimura et al. |
| 2009/0017330 | A1 | 1/2009 | Iwakuma et al. |
| 2009/0030202 | A1 | 1/2009 | Iwakuma et al. |
| 2009/0039776 | A1 | 2/2009 | Yamada et al. |
| 2009/0045730 | A1 | 2/2009 | Nishimura et al. |
| 2009/0045731 | A1 | 2/2009 | Nishimura et al. |
| 2009/0101870 | A1 | 4/2009 | Prakash et al. |
| 2009/0108737 | A1 | 4/2009 | Kwong et al. |
| 2009/0115316 | A1 | 5/2009 | Zheng et al. |
| 2009/0165846 | A1 | 7/2009 | Johannes et al. |
| 2009/0167162 | A1 | 7/2009 | Lin et al. |
| 2009/0179554 | A1 | 7/2009 | Kuma et al. |
| 2013/0126832 | A1* | 5/2013 | Yamamoto ......... H01L 51/0058 257/40 |
| 2013/0264560 | A1 | 10/2013 | Dobbs et al. |
| 2014/0217392 | A1* | 8/2014 | Hong ................ H01L 51/0052 257/40 |
| 2014/0316134 | A1* | 10/2014 | Stoessel ............. C07D 221/20 544/180 |
| 2015/0111337 | A1* | 4/2015 | Welker ................ C09B 57/00 438/99 |

FOREIGN PATENT DOCUMENTS

| | | |
|---|---|---|
| EP | 2034538 | 3/2009 |
| JP | 2005011610 | 1/2005 |
| JP | 2007123392 | 5/2007 |
| JP | 2007254297 | 10/2007 |
| JP | 2008074939 | 4/2008 |
| KR | 20120031684 | 4/2012 |
| KR | 20120078301 | 7/2012 |
| KR | 20120129733 | 11/2012 |
| WO | 0139234 | 5/2001 |
| WO | 0202714 | 1/2002 |
| WO | 0215645 | 2/2002 |
| WO | 03040257 | 5/2003 |
| WO | 03060956 | 7/2003 |
| WO | 2004093207 | 10/2004 |
| WO | 2004107822 | 12/2004 |
| WO | 2005014551 | 2/2005 |
| WO | 2005019373 | 3/2005 |
| WO | 2005030900 | 4/2005 |
| WO | 2005089025 | 9/2005 |
| WO | 2005123873 | 12/2005 |
| WO | 2006009024 | 1/2006 |
| WO | 2006056418 | 6/2006 |
| WO | 2006072002 | 7/2006 |
| WO | 2006082742 | 8/2006 |
| WO | 2006098120 | 9/2006 |
| WO | 2006100298 | 9/2006 |
| WO | 2006103874 | 10/2006 |
| WO | 2006114966 | 11/2006 |
| WO | 2006132173 | 12/2006 |
| WO | 2007002683 | 1/2007 |
| WO | 2007004380 | 1/2007 |
| WO | 2007063754 | 6/2007 |
| WO | 2007063796 | 6/2007 |
| WO | 2008056746 | 5/2008 |
| WO | 2008101842 | 8/2008 |
| WO | 2008132085 | 11/2008 |
| WO | 2009000673 | 12/2008 |
| WO | 2009003896 | 1/2009 |
| WO | 2009008311 | 1/2009 |
| WO | 2009018009 | 2/2009 |
| WO | 2009050290 | 4/2009 |
| WO | 2009021126 | 5/2009 |
| WO | 2009062578 | 5/2009 |
| WO | 2009063833 | 5/2009 |
| WO | 2009066778 | 5/2009 |
| WO | 2009066779 | 5/2009 |
| WO | 2009086028 | 7/2009 |
| WO | 2009100991 | 8/2009 |
| WO | 2012033061 | 3/2012 |
| WO | 2012133644 | 10/2012 |

(56) References Cited

FOREIGN PATENT DOCUMENTS

| WO | 2013032297 | 3/2013 |
|---|---|---|
| WO | 2013122402 | 8/2013 |
| WO | 2013191177 | 12/2013 |
| WO | 2014010823 | 1/2014 |
| WO | 2014015931 | 1/2014 |

OTHER PUBLICATIONS

Adachi, Chihaya et al., "Nearly 100% Internal Phosphorescence Efficiency in an Organic Light Emitting Device," J. Appl. Phys., 90(10): 5048-5051 (2001).

Adachi, Chihaya et al., "High-Efficiency Red Electrophosphorescence Devices," Appl. Phys. Lett., 78(11)1622-1624 (2001).

Aonuma, Masaki et al., "Material Design of Hole Transport Materials Capable of Thick-Film Formation in Organic Light Emitting Diodes," Appl. Phys. Lett., 90:183503-1-183503-3.

Baldo et al., Highly Efficient Phosphorescent Emission from Organic Electroluminescent Devices, Nature, vol. 395, 151-154, (1998).

Baldo et al., Very high-efficiency green organic light-emitting devices based on electrophosphorescence, Appl. Phys. Lett., vol. 75, No. 3, 4-6 (1999).

Gao, Zhiqiang et al., "Bright-Blue Electroluminescence from a Silyl-Substituted ter-(phenylene-vinylene) derivative," Appl, Phys. Lett., 74(6): 865-867 (1990).

Guo, Tzung-Fang et al., "Highly Efficient Electrophosphorescent Polymer Light-Emitting Devices," Organic Electronics, 115-20 (2000).

Hamada, Yuji et al., "High Luminance in Organic Electroluminescent Devices with Bis(10-hydroxybenzo[h]quinolinato)beryllium as an Emitter," Chem. Lett., 905-906 (1993).

Holmes, R.J. et al., "Blue Organic Electrophosphorescence Using Exothermic Host-Guest Energy Transfer," Appl. Phys. Lett., 82(15):2422-2424 (2003).

Hu, Nan-Xing et al., "Novel High Tg Hole-Transport Molecules Based on Indolo[3,2-b]carbazoles for Organic Light-Emitting Devices," Synthetic Metals, 111-112:421-424 (2000).

Huang, Jinsong et al., "Highly Efficient Red-Emission Polymer Phosphorescent Light-Emitting Diodes Based on Two Novel Tris(1-phenylisoquinolinato-C2,N)iridium(III) Derivates," Adv. Mater., 19 739-743 (2007).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Hung, L.S. et al., "Anode Modification in Organic Light-Emitting Diodes by Low-Frequency Plasma Polymerization of CHF3," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Ikeda, Hisao et al., "P-185 Low-Drive-Voltage OLEDs with a Buffer Layer Having Molybdenum Oxide," SID Symposium Digest, 37:923-925 (2006).

Inada, Hiroshi and Shirota, Yasuhiko,"1,3,5-Tris[4-(diphenylamino)phenl]benzene and its Methylsubstituted Derivatives as a Novel Class of Amorphous Molecular Materials," J. Mater. Chem., 3(3):319-320 (1993).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Kido, Junji et al., 1,2,4-Triazole Derivatives as an Electron Transport Layer in Organic Electroluminescent Devices, Jpn. J. Appl. Phys., 32:L917-L920 (1993).

Kuwabara, Yoshiyuki et al., "Thermally Stable Multilayered Organic Electroluminescent Devices Using Novel Starburst Molecules. 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).

Kwong, Raymond C. et al., "High Operational Stability of Electrophosphorescent Devices," Appl. Phys. Lett., 81(1) 162-164 (2002).

Lamansky, Sergey et al., "Synthesis and Characterization of Phosphorescent Cyclometalated Iridium Complexes," Inorg. Chem., 40(7):1704-1711 (2001).

Lee, Chang-Lyoul et al., "Polymer Phosphorescent Light-Emitting Devices Doped with Tris(2-phenylpyridine) Iridium as a Triplet Emitter," Appl. Phys. Lett. 77(15):2280-2282 (2000).

Lo, Shih-Chun et al., "Blue Phosphorescence from Iridium(III) Complexes at Room Temperature," Chem. Mater., 18(21)5119-5129 (2006).

Ma, Yuguang et al., "Triplet Luminescent Dinuclear-Gold(I) Complex-Based Light-Emitting Diodes with Low Turn-On voltage," Appl. Phys. Lett., 74(10):1361-1363 (1999).

Mi, Bao-Xiu et al., "Thermally Stable Hole-Transporting Material for Organic Light-Emitting Diode an Isoindole Derivative," Chem. Mater., 15(16):3148-3151 (2003).

Nishida, Jun-ichl et al., "Preparation, Characterization, and Electroluminescence Characteristics of α-Diimine-type Platinum(II) Complexes with Perfluorinated Phenyl Groups as Ligands," Chem. Lett., 34(4): 592-593 (2005).

Niu, Yu-Hua et al., "Highly Efficient Electrophosphorescent Devices with Saturated Red Emission from a Neutral Osmium Complex," Chem. Mater., 17(13):3532-3536 (2005).

Noda, Tetsuya and Shirota,Yasuhiko, "5,5'-Bis(dimesitylboryl)-2,2'-bithiophene and 5,5'-Bis(dimesitylboryl)-2,2'5',2"-terthiophene as a Novel Family of Electron-Transporting Amorphous Molecular Materials," J. Am. Chem. Soc., 120 (37):9714-9715 (1998).

Okumoto, Kenji et al., "Green Fluorescent Organic Light-Emitting Device with External Quantum Efficiency of Nearly 10%," Appl. Phys. Lett. 89:063504-1-063504-3 (2006).

Palilis, Leonidas C., "High Efficiency Molecular Organic Light-Emittng Diodes Based on Sitole Derivatives and Their Exciplexes," Organic Electronics, 4:113-121 (2003).

Paulose, Betty Marie Jennifer S. et al., "First Examples of Alkenyl Pyridines as Organic Ligands for Phosphorescent Iridium Complexes," 16(22):2003-2007 (2004).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Sakamoto, Youichi et al., "Synthesis, Characterization, and Electron-Transport Property of Perfluorinated Phenylene Dendrimers," J. Am. Chem. Soc., 122(8):1832-1833 (2000).

Salbeck, J. et al., "Low Molecular Organic Glasses for Blue Electroluminescence," Synthetic Metals, 91209-215 (1997).

Shirota, Yasuhiko et al., "Starburst Molecules Based on p-Electron Systems as Materials for Organic Electroluminescent Devices," Journal of Luminescence, 72-74;985-991 (1997).

Sotoyama, Wataru et al., "Efficient Organic Light-Emitting Diodes with Phosphorescent Platinum Complexes Containing $N^{\wedge}C^{\wedge}N$-Co-ordinating Tridentate Ligand," Appl. Phys. Lett., 86:153505-1-153505-3 (2006).

Sun, Yiru and Forrest, Stephen R.,"High Efficiency White Organic Light Emitting Devices with Three Separate Phosphorescent Emission Layers," Appl. Phys. Lett., 91:263503-1-263503-3 (2007).

T. Ostergård et al., "Langmuir-Blodgett Light Emitting Diodes of Poly(3-Hexylthiophene) Electro-Optical Characteristics Related to Structure," Synthetic Metals, 87:171-177 (1997).

Takizawa, Shin-ya et al., "Phosphorescent Iridium Complexes Based on 2-Phenylimidazo[1,2- α]pyridine Ligands Tuning of Emission Color toward the Blue Region and Application to Polymer Light-Emitting Devices," Inorg. Chem., 46(10):4308-4319 (2007).

Tang, C.W. and VanSlyke, S.A., "Organic Electroluminescent Diodes," Appl. Phys. Lett., 51(12):913-915 (1987).

Tung, Yung-Liang et al., "Organic Light-Emitting Diodes Based on Charge-Neutral Ru II PHosphorescent Emitters," Adv. Mater., 17(8)1059-1064 (2005).

(56) References Cited

OTHER PUBLICATIONS

Van Slyke, S. A. et al., "Organic Electroluminescent Devices with Improved Stability," Appl. Phys. Lett., 69(15):2160-2162 (1996).
Wang, Y. et al., "Highly Efficient Electroluminescent Materials Based on Fluorinated Organometallic Iridium Compounds," Appl. Phys. Lett., 79(4):449-451 (2001).
Wong, Keith Man-Chung et al., A Novel Class of Phosphorescent Gold(II) Alkynyl-Based Organic Light-Emitting Devices with Tunable Colour, Chem. Commun., 2906-2908 (2005).
Wong, Wai-Yeung, "Multifunctional Iridium Complexes Based on Carbazole Modules as Highly Efficient Electrophosphors," Angew. Chem. Int. Ed., 45:7800-7803 (2006).

\* cited by examiner

ORGANIC ELECTROLUMINESCENT MATERIALS AND DEVICES

PARTIES TO A JOINT RESEARCH AGREEMENT

The claimed invention was made by, on behalf of, and/or in connection with one or more of the following parties to a joint university corporation research agreement: Regents of the University of Michigan, Princeton University, University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to compounds for use as hosts or co-hosts and devices, such as organic light emitting diodes, including the same.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted $Ir(ppy)_3$, which has the following structure:

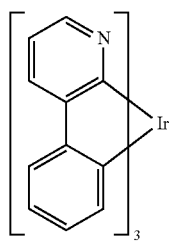

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY OF THE INVENTION

According to an embodiment, a compound having a structure of Formula I shown below:

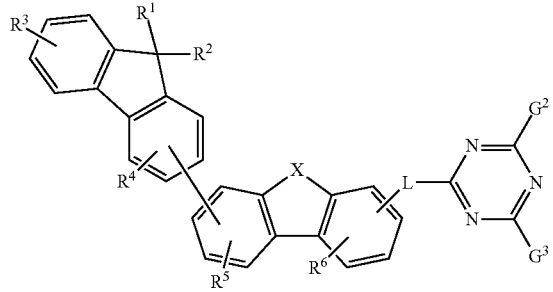

is provided. In the structure of Formula I:

X is selected from a group consisting of O, S and Se;

$G^2$ and $G^3$ are each independently selected from the group consisting of benzene, biphenyl, fluorene, naphthalene, phenanthrene, triphenylene, dibenzofuran, dibenzothiophene, dibenzoselenophene, pyridine, pyrimidine, quinoline, isoquinoline, phenanthroline, aza-fluorene, and combinations thereof;

L is selected from the group consisting of phenyl, biphenyl, terphenyl and pyridine, and combinations thereof;

$G^2$, $G^3$ and L are each optionally further substituted with one or more unfused substituents selected from the group consisting of deuterium, alkyl, alkoxyl, cycloalkyl, cycloalkoxyl, halogen, nitro, nitrile, silyl, benzene, biphenyl, terphenyl, pyridine, and combinations thereof;

$R^3$ represents mono, di, tri, or tetra substitution, or no substitution;

$R^4$, $R^5$ and $R^6$ each independently represent mono, di, or tri substitution, or no substitution;

$R^1$, $R^2$, and each $R^3$, $R^4$, $R^5$ and $R^6$ are an unfused substituent selected from the group consisting of hydrogen, deuterium, alkyl, alkoxyl, cycloalkyl, cycloalkoxyl, halogen, nitro, nitrile, silyl, benzene, biphenyl, terphenyl, pyridine, and combinations thereof; and $R^1$ and $R^2$ are optionally joined to form a ring.

According to another aspect of the present disclosure, a device that includes one or more organic light emitting devices is also provided. At least one of the organic light emitting devices can include an anode, a cathode, and an organic layer disposed between the anode and the cathode. The organic layer can include one or more emitter dopants. The organic layer can include a compound according to Formula I, and its variations, as described herein. The compound according to Formula I can be a host and the organic layer can be an emissive layer.

According to yet another embodiment, a formulation containing a compound of Formula I is provided.

According to another embodiment, a composition comprising a first and second compound is provided. The first compound can have a structure of Formula I and its variations as described herein, while the second compound can have a structure of Formula III:

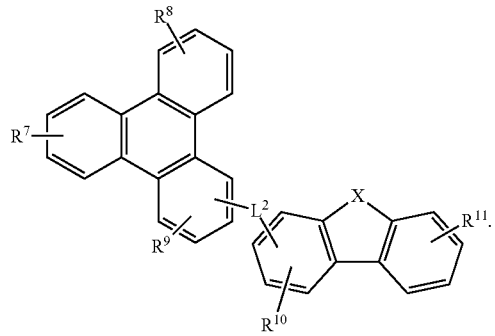

In the structure of Formula III:

X is selected from the group consisting of S, O, Se, and NR', $L^2$ is selected from a group consisting of direct bond, phenyl, biphenyl, terphenyl, fluorene, triphenylene, dibenzofuran, dibenzothiophene, dibenzoselenophene, carbazole and pyridine, and combinations thereof, $L^2$ is optionally further substituted with one or more substituents selected from a group consisting of hydrogen, deuterium, alkyl, alkoxyl, cycloalkyl, cycloalkoxyl, halogen, nitro, nitrile, silyl, aryl, heteroaryl, and combinations thereof, R', $R^7$, $R^8$, $R^9$, $R^{10}$ and $R^{11}$ are each an unfused substituent selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, $R^7$, $R^8$ and $R^{11}$ each independently represent mono, di, tri, or tetra substitution, or no substitution, and $R^9$ and $R^{10}$ each independently represent mono, di, or tri substitution, or no substitution.

In another embodiment of the present disclosure, a method for fabricating an organic light emitting device comprising a first electrode, a second electrode, and a first organic layer disposed between the first electrode and the second electrode, where the first organic layer comprises a first composition comprising a mixture of a first compound and a second compound is provided. The method includes providing a substrate having the first electrode disposed thereon; depositing the first composition over the first electrode; and depositing the second electrode over the first organic layer. The depositing step can be implemented using a chemical vapor deposition technique (e.g., vacuum thermal evaporation). The first compound can have a structure of Formula I and its variations as described herein, while the second compound can have a structure of Formula III, and its variations as described herein.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
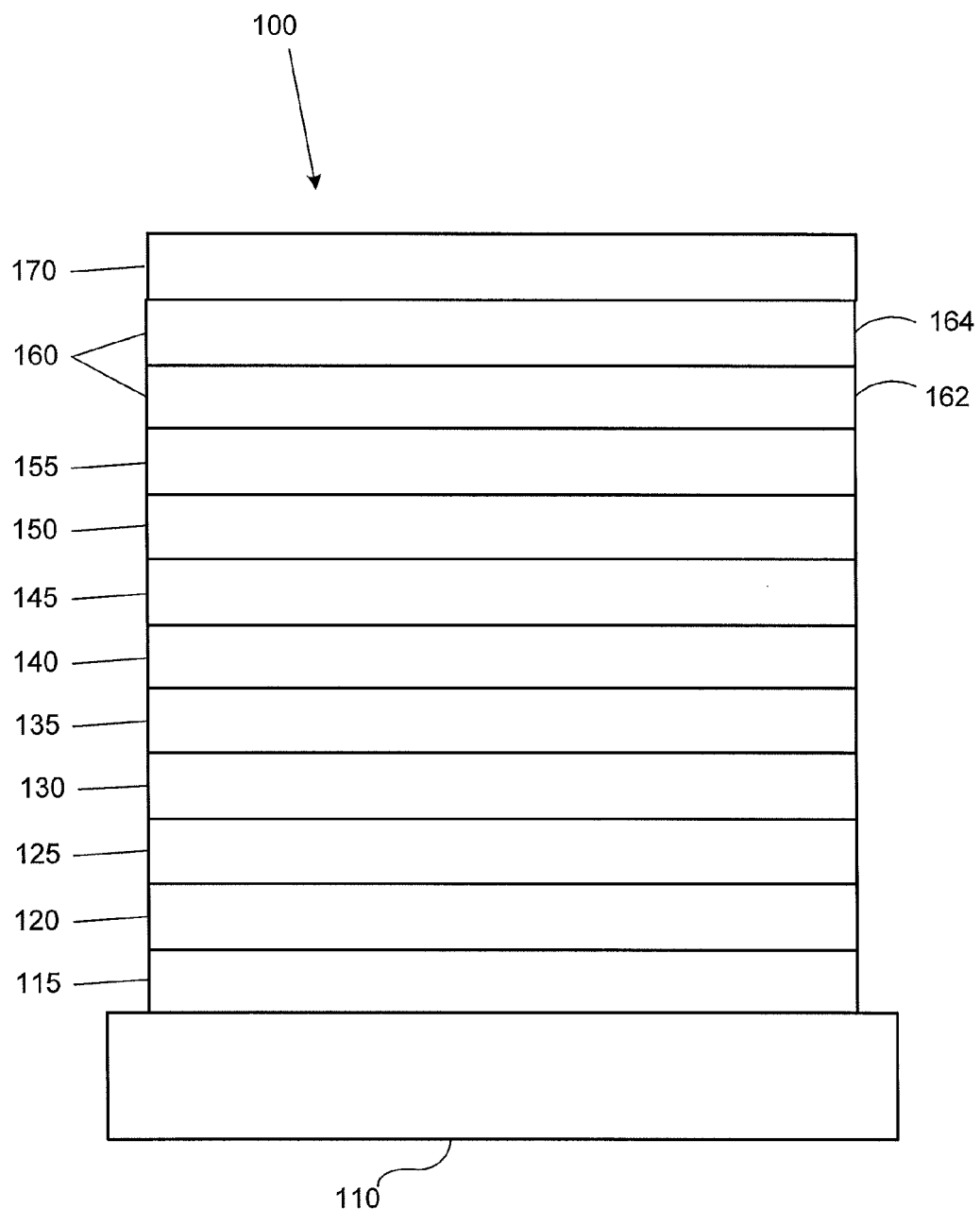
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
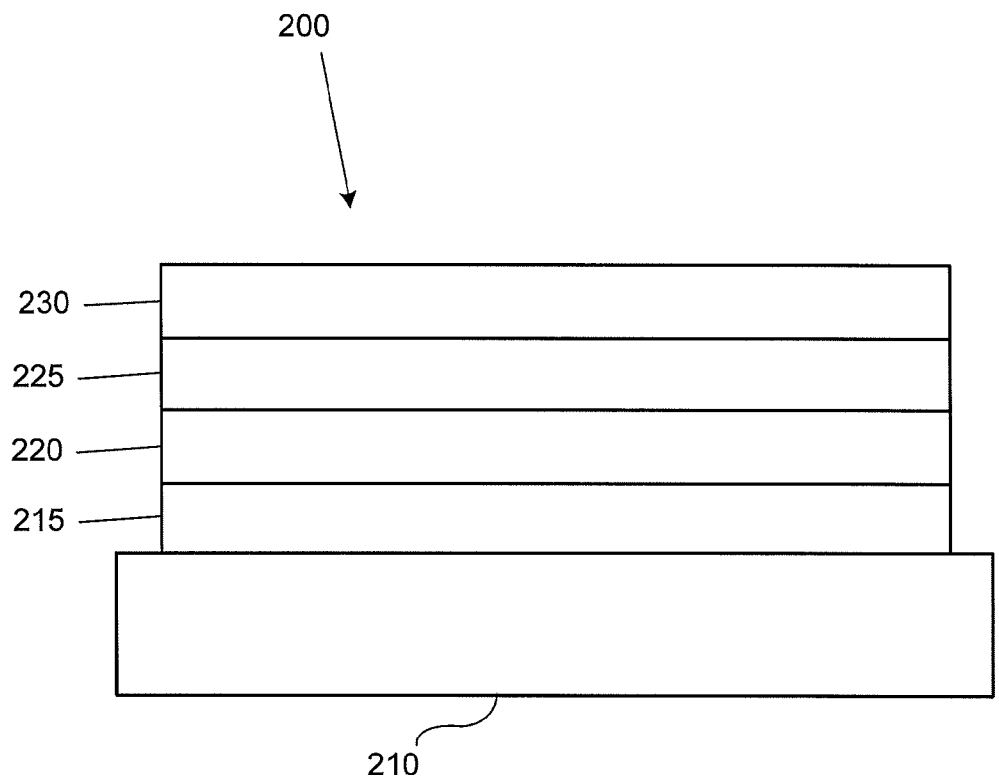
FIG. 2 shows an inverted organic light emitting device that does not have a separate electron transport layer.
Figure 3:
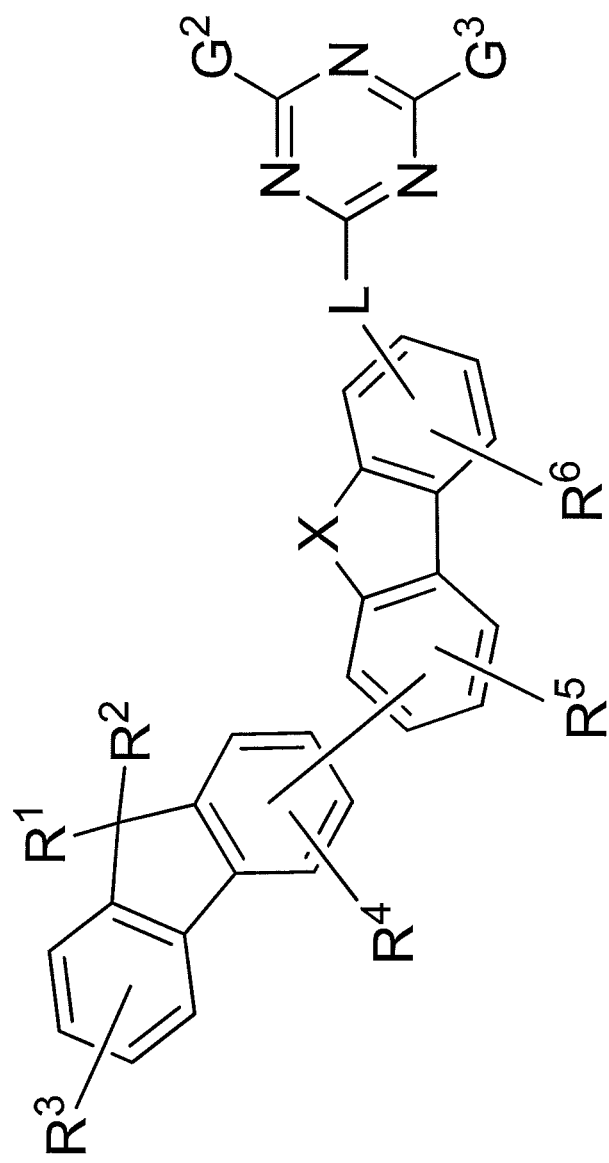
FIG. 3 shows Formula I as disclosed herein.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, cell phones, tablets, phablets, personal digital assistants (PDAs), laptop computers, digital cameras, camcorders, viewfinders, micro-displays, 3-D displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.), but could be used outside this temperature range, for example, from −40 degree C. to +80 degree C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The term "halo," "halogen," or "halide" as used herein includes fluorine, chlorine, bromine, and iodine.

The term "alkyl" as used herein contemplates both straight and branched chain alkyl radicals. Preferred alkyl groups are those containing from one to fifteen carbon atoms and includes methyl, ethyl, propyl, isopropyl, butyl, isobutyl, tert-butyl, and the like. Additionally, the alkyl group may be optionally substituted.

The term "cycloalkyl" as used herein contemplates cyclic alkyl radicals. Preferred cycloalkyl groups are those containing 3 to 7 carbon atoms and includes cyclopropyl, cyclopentyl, cyclohexyl, and the like. Additionally, the cycloalkyl group may be optionally substituted.

The term "alkenyl" as used herein contemplates both straight and branched chain alkene radicals. Preferred alkenyl groups are those containing two to fifteen carbon atoms. Additionally, the alkenyl group may be optionally substituted.

The term "alkynyl" as used herein contemplates both straight and branched chain alkyne radicals. Preferred alkyl groups are those containing two to fifteen carbon atoms. Additionally, the alkynyl group may be optionally substituted.

The terms "aralkyl" or "arylalkyl" as used herein are used interchangeably and contemplate an alkyl group that has as a substituent an aromatic group. Additionally, the aralkyl group may be optionally substituted.

The term "heterocyclic group" as used herein contemplates aromatic and non-aromatic cyclic radicals. Hetero-aromatic cyclic radicals also means heteroaryl. Preferred hetero-non-aromatic cyclic groups are those containing 3 or 7 ring atoms which includes at least one hetero atom, and includes cyclic amines such as morpholino, piperdino, pyrrolidino, and the like, and cyclic ethers, such as tetrahydrofuran, tetrahydropyran, and the like. Additionally, the heterocyclic group may be optionally substituted.

The term "aryl" or "aromatic group" as used herein contemplates single-ring groups and polycyclic ring systems. The polycyclic rings may have two or more rings in which two carbons are common to two adjoining rings (the rings are "fused") wherein at least one of the rings is aromatic, e.g., the other rings can be cycloalkyls, cycloalkenyls, aryl, heterocycles, and/or heteroaryls. Additionally, the aryl group may be optionally substituted.

The term "heteroaryl" as used herein contemplates single-ring hetero-aromatic groups that may include from one to three heteroatoms, for example, pyrrole, furan, thiophene, imidazole, oxazole, thiazole, triazole, pyrazole, pyridine, pyrazine and pyrimidine, and the like. The term heteroaryl also includes polycyclic hetero-aromatic systems having two or more rings in which two atoms are common to two adjoining rings (the rings are "fused") wherein at least one of the rings is a heteroaryl, e.g., the other rings can be cycloalkyls, cycloalkenyls, aryl, heterocycles, and/or heteroaryls. Additionally, the heteroaryl group may be optionally substituted.

The alkyl, cycloalkyl, alkenyl, alkynyl, aralkyl, heterocyclic group, aryl, and heteroaryl may be optionally substituted with one or more substituents selected from the group consisting of hydrogen, deuterium, halogen, alkyl, cycloalkyl, heteroalkyl, arylalkyl, alkoxy, aryloxy, amino, cyclic amino, silyl, alkenyl, cycloalkenyl, heteroalkenyl, alkynyl, aryl, heteroaryl, acyl, carbonyl, carboxylic acid, ether, ester, nitrile, isonitrile, sulfanyl, sulfinyl, sulfonyl, phosphino, and combinations thereof.

As used herein, "substituted" indicates that a substituent other than H is bonded to the relevant position, such as carbon. Thus, for example, where $R^1$ is mono-substituted, then one $R^1$ must be other than H. Similarly, where $R^1$ is di-substituted, then two of $R^1$ must be other than H. Similarly, where $R^1$ is unsubstituted, $R^1$ is hydrogen for all available positions.

The "aza" designation in the fragments described herein, i.e. aza-dibenzofuran, aza-dibenzonethiophene, etc. means that one or more of the C—H groups in the respective fragment can be replaced by a nitrogen atom, for example, and without any limitation, azatriphenylene encompasses both dibenzo[f,h]quinoxaline and dibenzo[f,h]quinoline. One of ordinary skill in the art can readily envision other nitrogen analogs of the aza-derivatives described above, and all such analogs are intended to be encompassed by the terms as set forth herein.

It is to be understood that when a molecular fragment is described as being a substituent or otherwise attached to another moiety, its name may be written as if it were a fragment (e.g. phenyl, phenylene, naphthyl, dibenzofuryl) or as if it were the whole molecule (e.g. benzene, naphthalene, dibenzofuran). As used herein, these different ways of designating a substituent or attached fragment are considered to be equivalent.

The compounds disclosed herein contain triazine linked to a fluorene-dibenzothiophene/dibenzofuran/dibenzoselenophene moiety. Fluorene, dibenzothiophene and its analogues are excellent charge transport moieties due to their rigid chemical structures conducive to molecular assembly. Triazine has a deep LUMO level that enables efficient electron injection from adjacent layers. The compounds contain two modules connected by benzene or pyridine-based linkers. One module contains fluorene connected directly to dibenzothiophene, or an analogue thereof, to produce an extended rigid structure to further promote molecular assembly. The other module contains an electron-deficient triazine moiety to provide sufficiently deep LUMO levels for electron injection. It has been determined that the separation of these two modules by the benzene or pyridine-based linkers enables individual tuning of the two modules. Compounds of this novel chemical structure improve OLED device performance.

According to one embodiment, a compound having a structure of Formula I shown below:

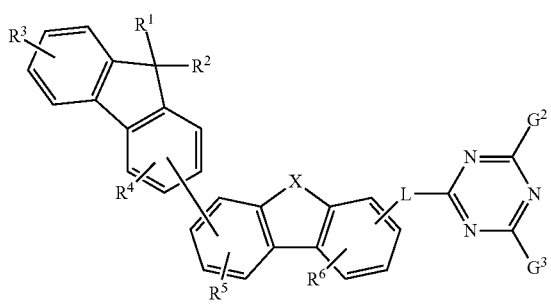

is disclosed. In the structure of Formula I:

X is selected from a group consisting of O, S and Se;

$G^2$ and $G^3$ are each independently selected from the group consisting of benzene, biphenyl, fluorene, naphthalene, phenanthrene, triphenylene, dibenzofuran, dibenzothiophene, dibenzoselenophene, pyridine, pyrimidine, quinoline, isoquinoline, phenanthroline, aza-fluorene, and combinations thereof;

L is selected from the group consisting of phenyl, biphenyl, terphenyl and pyridine, and combinations thereof;

$G^2$, $G^3$ and L are each optionally further substituted with one or more unfused substituents selected from the group consisting of deuterium, alkyl, alkoxyl, cycloalkyl, cycloalkoxyl, halogen, nitro, nitrile, silyl, benzene, biphenyl, terphenyl, pyridine, and combinations thereof;

$R^3$ represents mono, di, tri, or tetra substitution, or no substitution;

$R^4$, $R^5$ and $R^6$ each independently represent mono, di, or tri substitution, or no substitution;

$R^1$, $R^2$, and each $R^3$, $R^4$, $R^5$ and $R^6$ are an unfused substituent selected from the group consisting of hydrogen, deuterium, alkyl, alkoxyl, cycloalkyl, cycloalkoxyl, halogen, nitro, nitrile, silyl, benzene, biphenyl, terphenyl, pyridine, and combinations thereof; and $R^1$ and $R^2$ are optionally joined to form a ring.

In some embodiments, $R^1$ and $R^2$ are not joined to form a ring. In other embodiments, $R^1$ and $R^2$ are joined to form a ring.

In some embodiments, $R^1$, $R^2$, and each $R^3$, $R^4$, $R^5$ and $R^6$ are an unfused substituent selected from the group consisting of hydrogen, deuterium, halogen, nitro, methyl, ethyl, propyl, butyl, pentyl, hexyl, heptyl, octyl, isopropyl, isobutyl, tert-butyl, tert-butylmethyl, 2-ethylhexyl, 2-ethyloctyl, cyclopentyl, cyclohexyl, benzene, biphenyl, terphenyl, pyridine, naphthalene, quinoline, and combinations thereof.

In some embodiments, the compound is selected from the group consisting of:

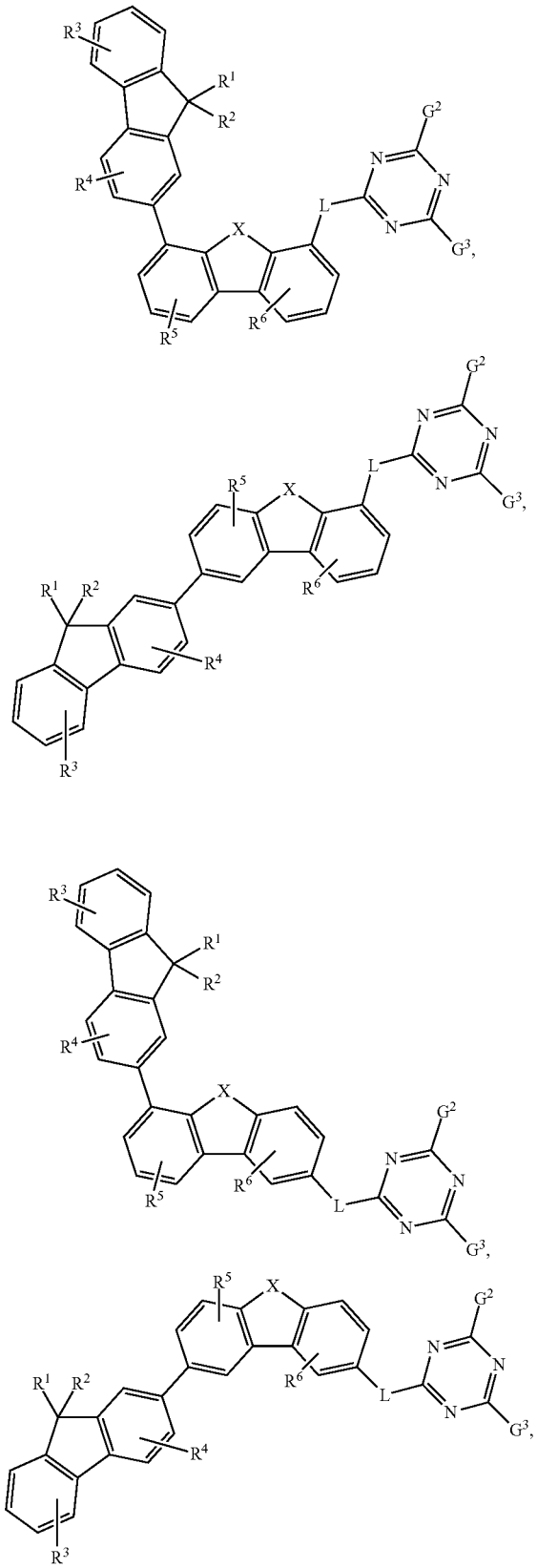

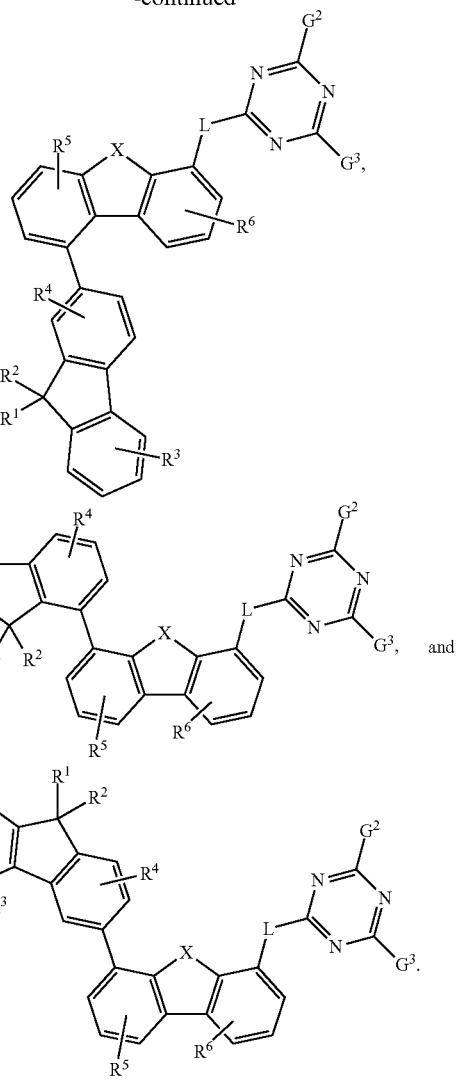

In some embodiments, the compound has a structure of Formula II

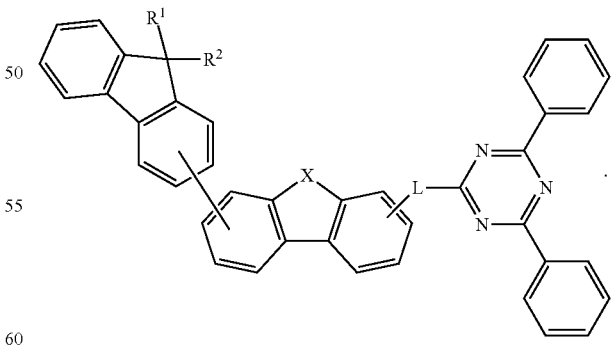

In some embodiments, the structure of Formula II is not further substituted. In some embodiments, the structure of Formula II may be further substituted by one or more of the following: deuterium, alkyl, alkoxyl, cycloalkyl, cycloalkoxyl, halogen, nitro, nitrile, silyl, benzene, biphenyl, terphenyl, pyridine, and combinations thereof.

In some embodiments, $G^2$ and $G^3$ are each independently a moiety selected from the group consisting of:

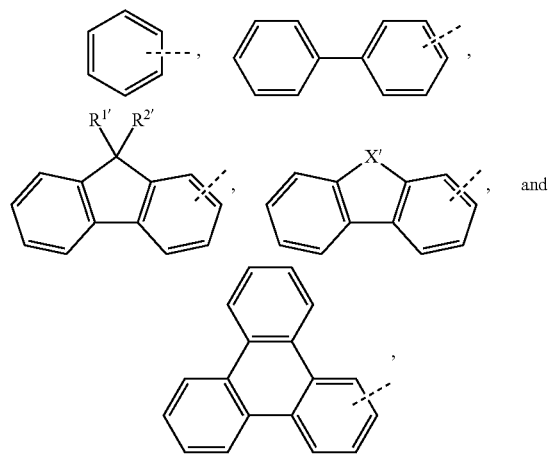

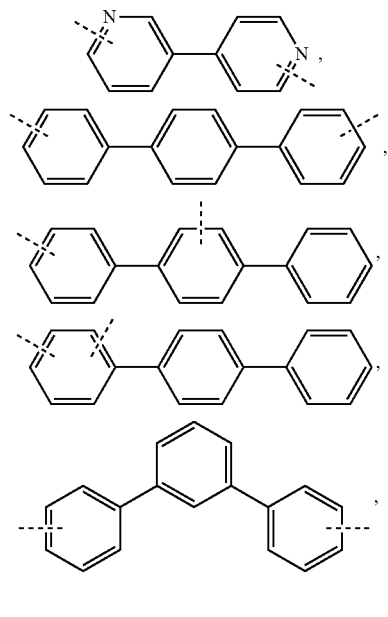

wherein $R^{1'}$ and $R^{2'}$ are independently selected from the group consisting of hydrogen, deuterium, methyl, ethyl, propyl, butyl, pentyl, hexyl, heptyl, octyl, isopropyl, isobutyl, terbutyl, terbutylmethyl, 2-ethylhexyl, 2-ethyloctyl, cyclopentyl, cyclohexyl, benzene, biphenyl, terphenyl, and combinations thereof;

wherein $R^{1'}$ and $R^{2'}$ are optionally joined to form a ring; and wherein X' is selected from a group consisting of O, S and Se. In some embodiments, $G^2$ and $G^3$ are not further substituted. In other embodiments, $G^2$ and $G^3$ are further substituted by one or more of deuterium, alkyl, alkoxyl, cycloalkyl, cycloalkoxyl, halogen, nitro, nitrile, silyl, benzene, biphenyl, terphenyl, pyridine.

In some embodiments, L is a moiety selected from the group consisting of:

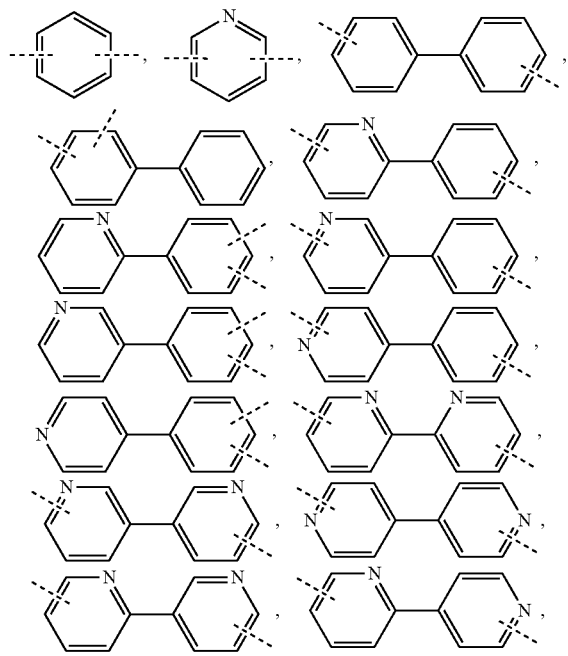

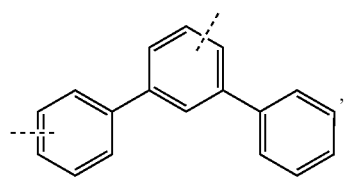

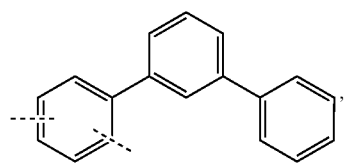

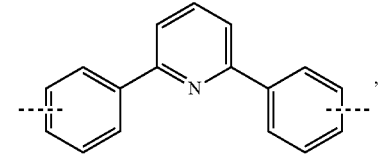

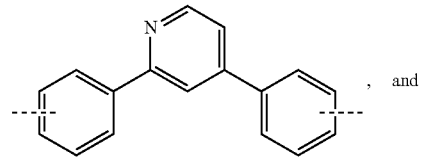

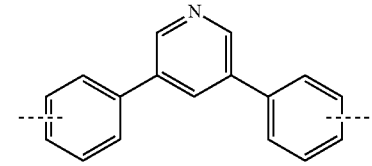

In some embodiments, L is not further substituted. In other embodiments, L is further substituted by one or more of deuterium, alkyl, alkoxyl, cycloalkyl, cycloalkoxyl, halogen, nitro, nitrile, silyl, benzene, biphenyl, terphenyl, pyridine.

In some more specific embodiments, the compound is selected from the group consisting of:

Compounds 1 through 3, each represented by the formula:

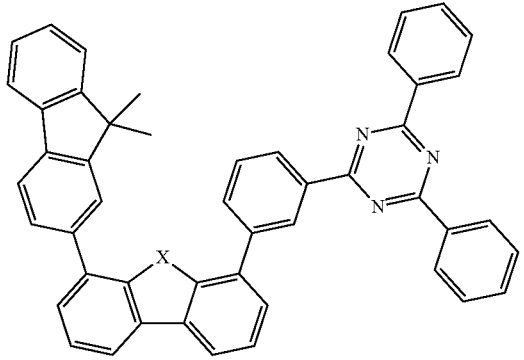

where in Compound 1: X = O,
in Compound 2, X = S, and
in Compound 3, X = Se,

Compounds 4 through 6, each represented by the formula:

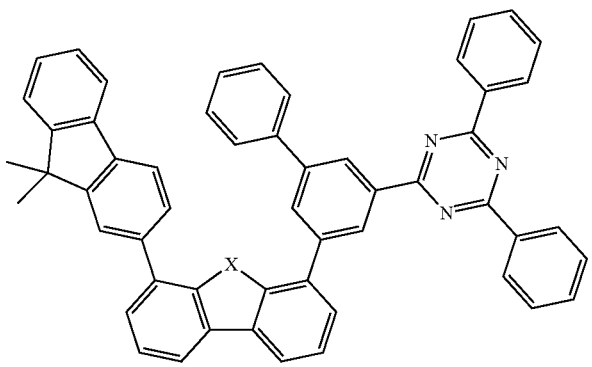

where in Compound 4: X = O,
in Compound 5, X = S, and
in Compound 6, X = Se,

Compounds 7 through 9, each represented by the formula:

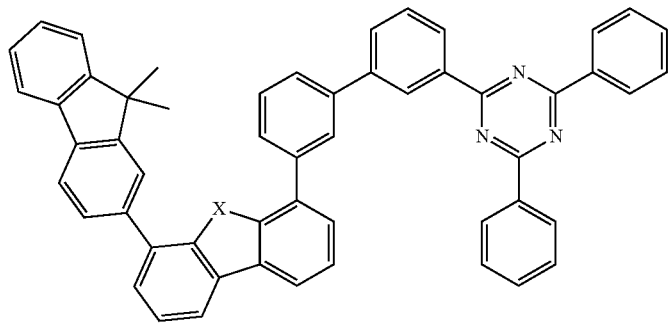

where in Compound 7: X = O,
in Compound 8, X = S, and
in Compound 9, X = Se,

Compounds 10 through 12, each represented by the formula:
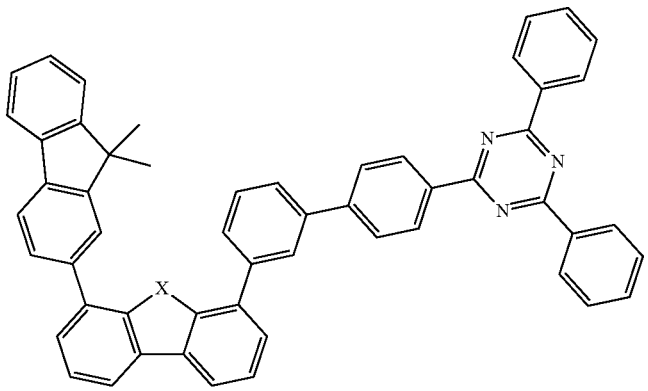
where in Compound 10: X = O,
in Compound 11, X = S, and
in Compound 12, X = Se,
Compounds 13 through 15, each represented by the formula:
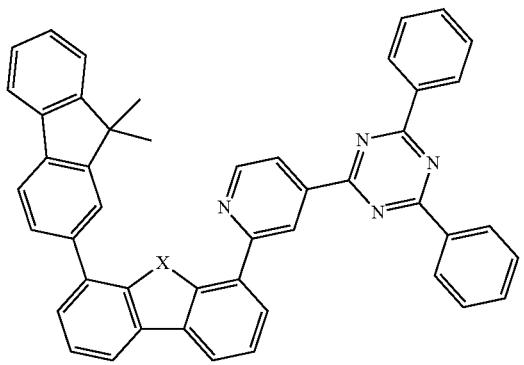
where in Compound 13: X = O,
in Compound 14, X = S, and
in Compound 15, X = Se,
Compounds 16 through 18, each represented by the formula:
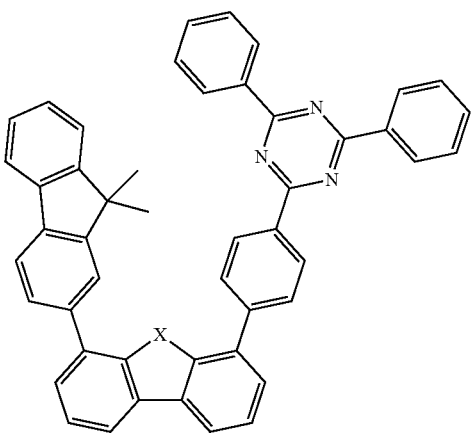
where in Compound 16: X = O,
in Compound 17, X = S, and
in Compound 18, X = Se, -continued
Compounds 19 through 21, each represented by the formula:
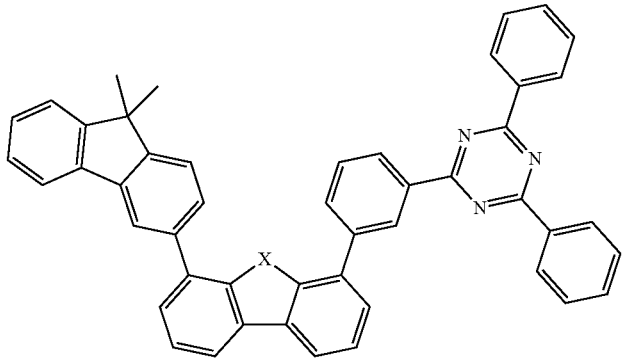
where in Compound 19: X = O,
in Compound 20, X = S, and
in Compound 21, X = Se,
Compounds 22 through 24, each represented by the formula:
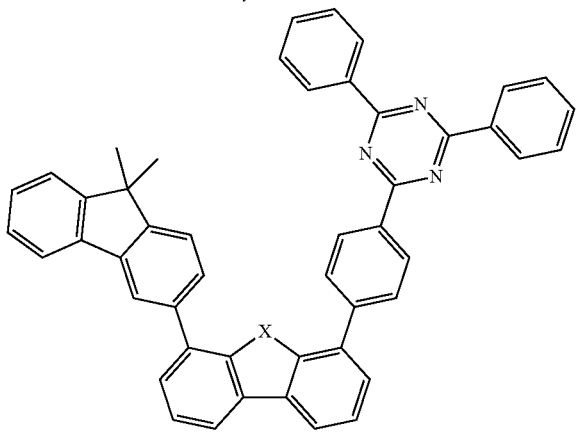
where in Compound 22: X = O,
in Compound 23, X = S, and
in Compound 24, X = Se,
Compounds 25 through 27, each represented by the formula:
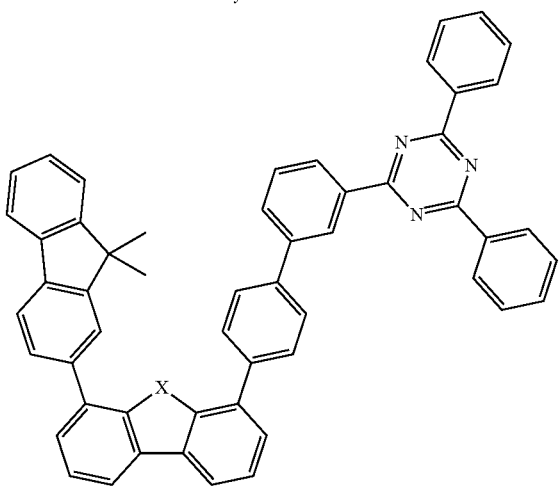
where in Compound 25: X = O,
in Compound 26, X = S, and
in Compound 27, X = Se, Compounds 28 through 30, each represented by the formula:
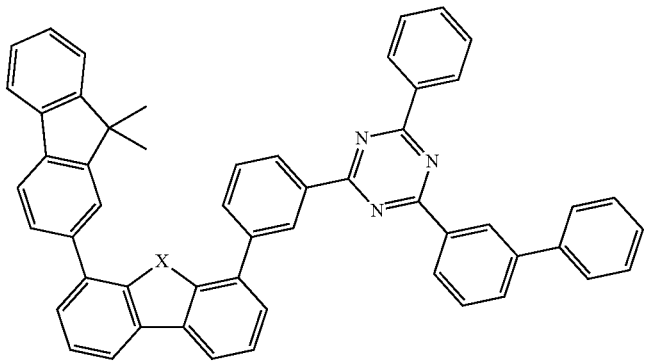
where in Compound 28: X = O,
in Compound 29, X = S, and
in Compound 30, X = Se,
Compounds 31 through 33, each represented by the formula:
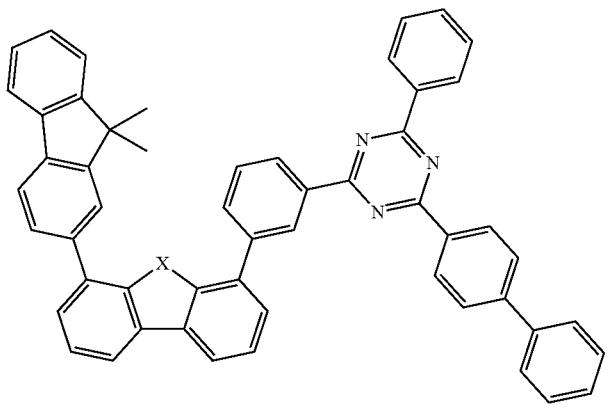
where in Compound 31: X = O,
in Compound 32, X = S, and
in Compound 33, X = Se,
Compounds 34 through 36, each represented by the formula:
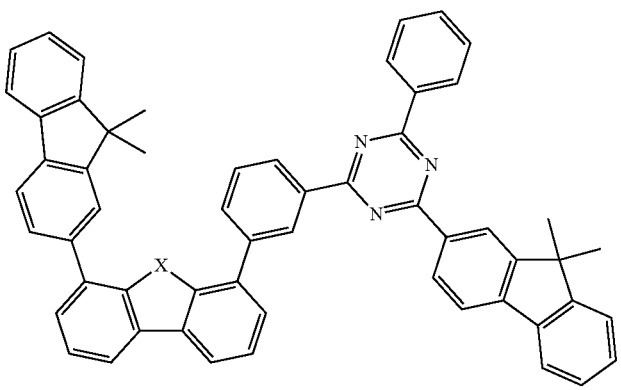
where in Compound 34: X = O,
in Compound 35, X = S, and
in Compound 36, X = Se, -continued
Compounds 37 through 39, each represented by the formula:
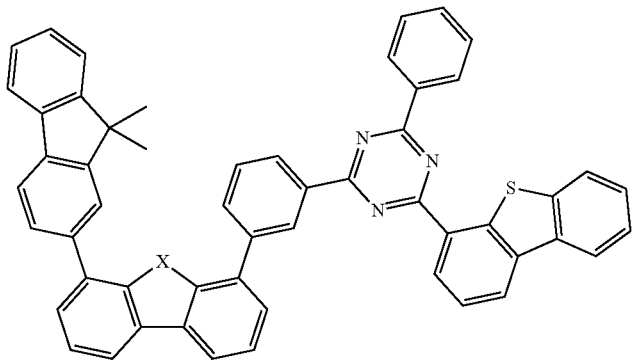
where in Compound 37: X = O,
in Compound 38, X = S, and
in Compound 39, X = Se,
Compounds 40 through 42, each represented by the formula:
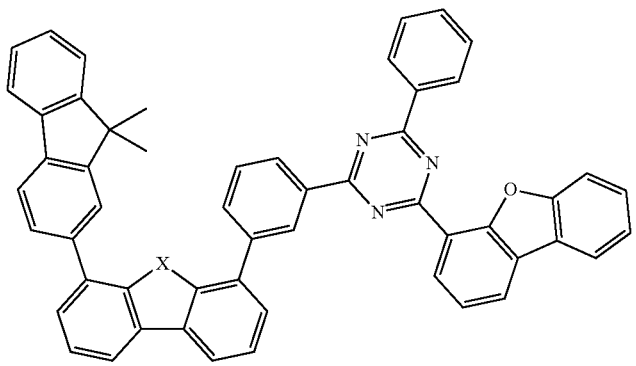
where in Compound 40: X = O,
in Compound 41, X = S, and
in Compound 42, X = Se,
Compounds 43 through 45, each represented by the formula:
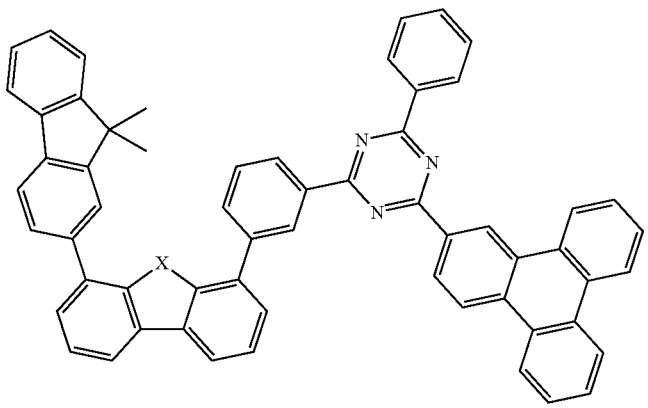
where in Compound 43: X = O,
in Compound 44, X = S, and
in Compound 45, X = Se, Compounds 46 through 48, each represented by the formula:
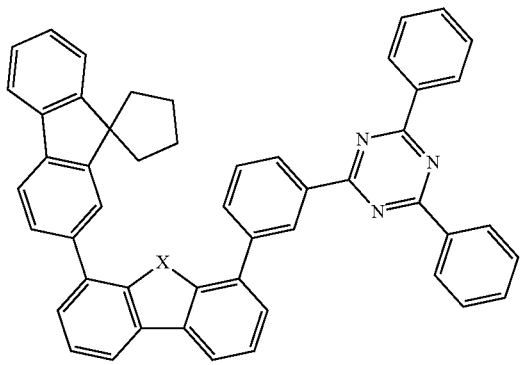
where in Compound 46: X = O,
in Compound 47, X = S, and
in Compound 48, X = Se,
Compounds 49 through 51, each represented by the formula:
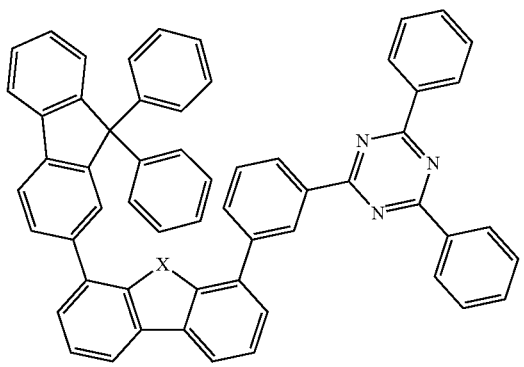
where in Compound 49: X = O,
in Compound 50, X = S, and
in Compound 51, X = Se,
Compounds 52 through 54, each represented by the formula:
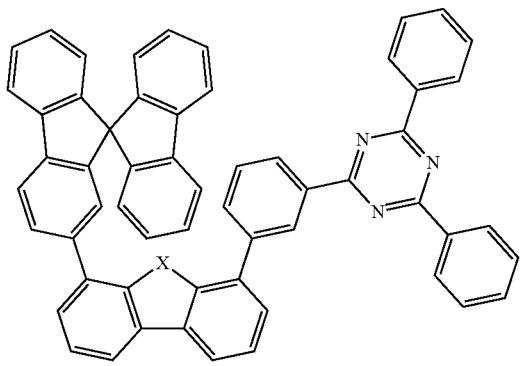
where in Compound 52: X = O,
in Compound 53, X = S, and
in Compound 54, X = Se, -continued
Compounds 55 through 57, each represented by the formula:
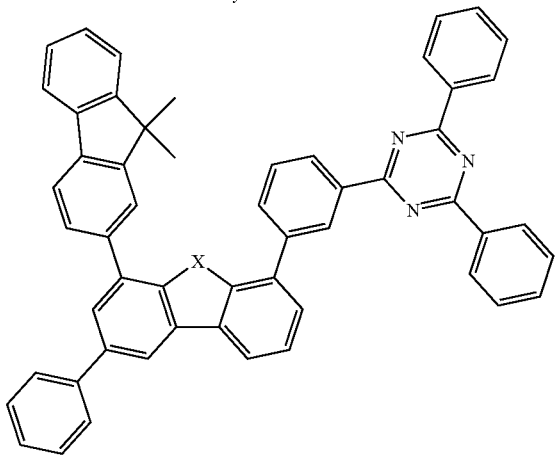
where in Compound 55: X = O,
in Compound 56, X = S, and
in Compound 57, X = Se,
Compounds 58 through 60, each represented by the formula:
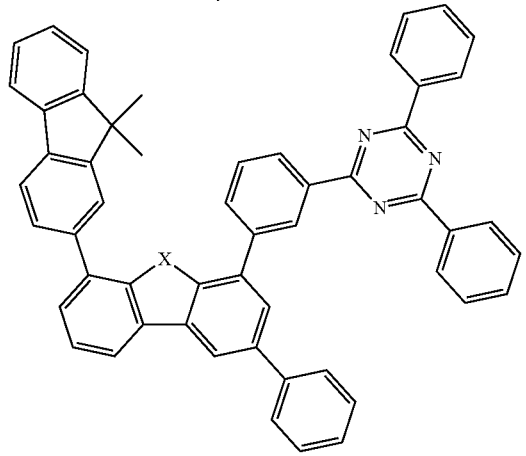
where in Compound 58: X = O,
in Compound 59, X = S, and
in Compound 60, X = Se,
Compounds 61 through 63, each represented by the formula:
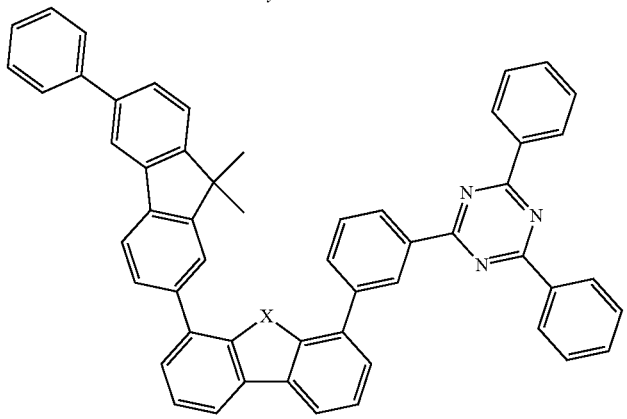
where in Compound 61: X = O,
in Compound 62, X = S, and
in Compound 63, X = Se, Compounds 64 through 66, each represented by the formula:
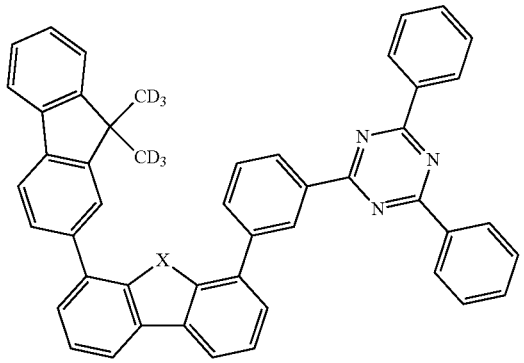
where in Compound 64: X = O,
in Compound 65, X = S, and
in Compound 66, X = Se,
Compounds 67 through 69, each represented by the formula:
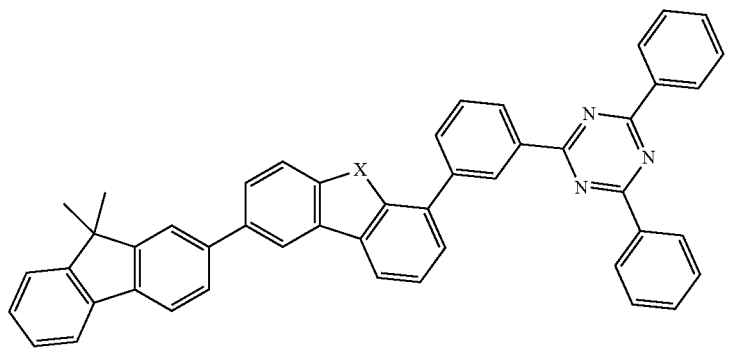
where in Compound 67: X = O,
in Compound 68, X = S, and
in Compound 69, X = Se,
Compounds 70 through 72, each represented by the formula:
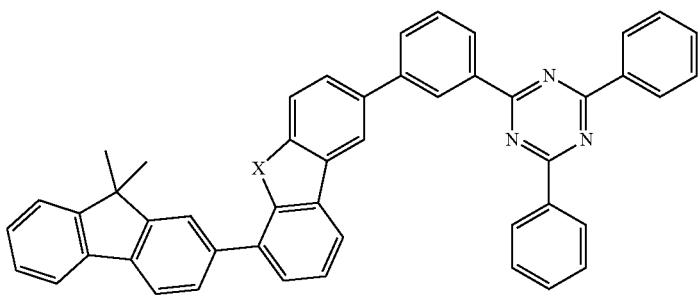
where in Compound 70: X = O,
in Compound 71, X = S, and
in Compound 72, X = Se, Compounds 73 through 75, each represented by the formula:
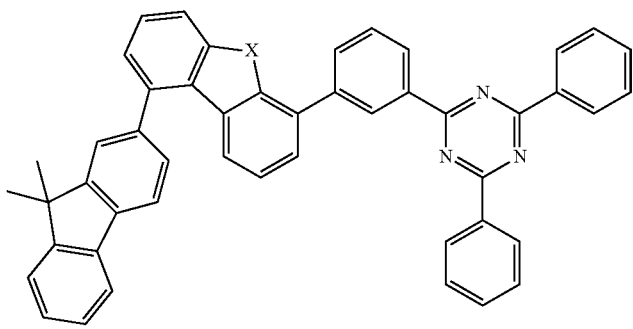
where in Compound 73: X = O,
in Compound 74, X = S, and
in Compound 75, X = Se,
Compounds 76 through 78, each represented by the formula:
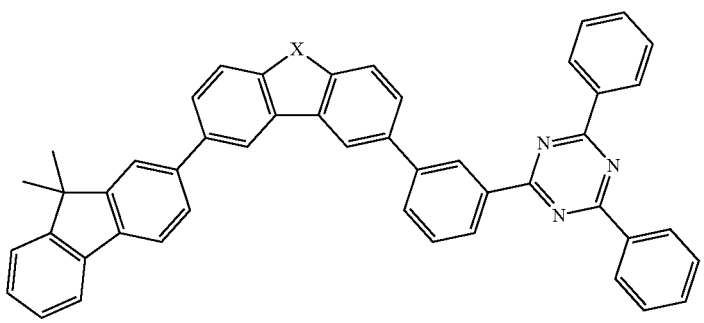
where in Compound 76: X = O,
in Compound 77, X = S, and
in Compound 78, X = Se,
Compounds 79 through 81, each represented by the formula:
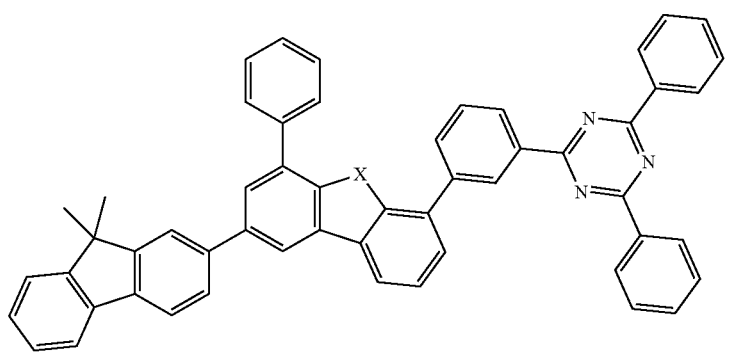
where in Compound 79: X = O,
in Compound 80, X = S, and
in Compound 81, X = Se, Compounds 79 through 81, each represented by the formula:
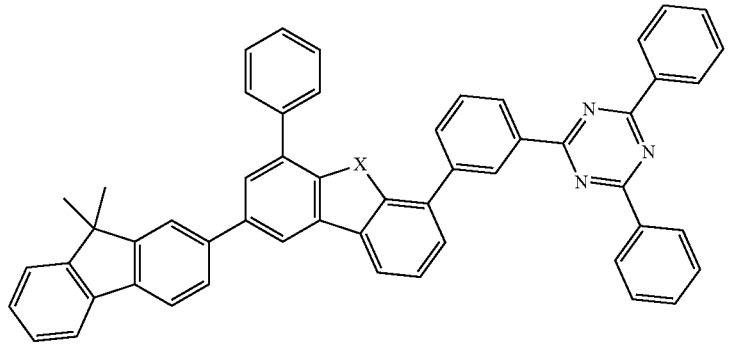
where in Compound 79: X = O,
in Compound 80, X = S, and
in Compound 81, X = Se,
Compounds 82 through 84, each represented by the formula:
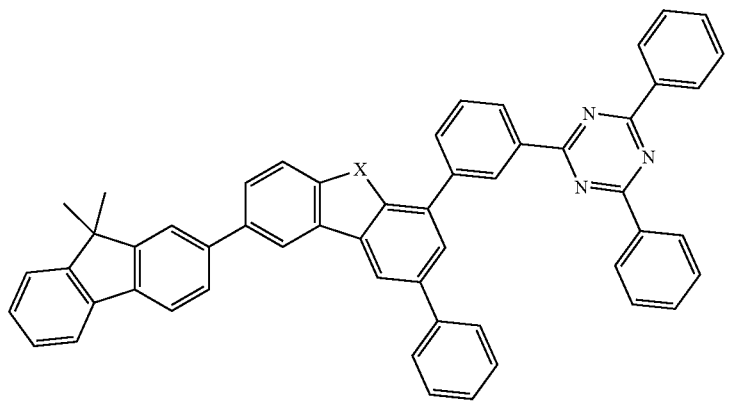
where in Compound 82: X = O,
in Compound 83, X = S, and
in Compound 84, X = Se,
Compounds 85 through 87, each represented by the formula:
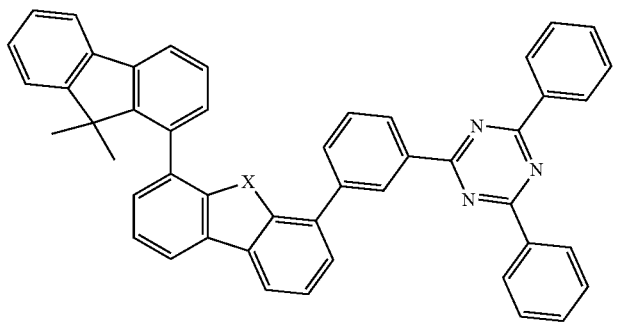
where in Compound 85: X = O,
in Compound 86, X = S, and
in Compound 87, X = Se, -continued
Compounds 88 through 90 each represented by the formula:
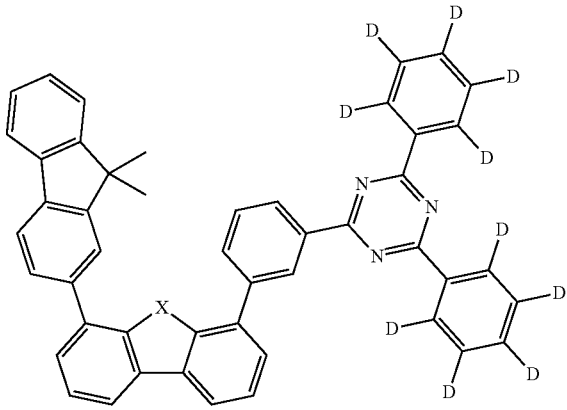
where in Compound 88: X = O,
in Compound 89, X = S, and
in Compound 90, X = Se,
Compounds 91 through 93 each represented by the formula:
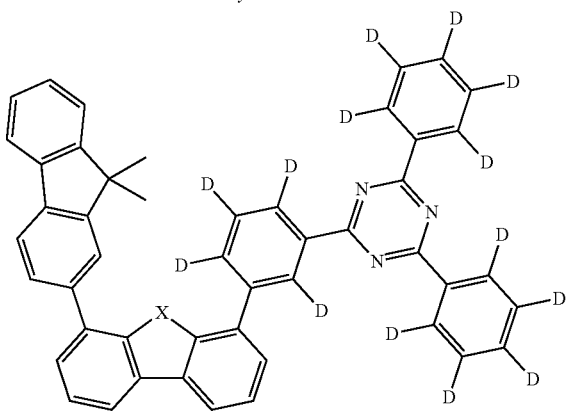
where in Compound 91: X = O,
in Compound 92, X = S, and
in Compound 93, X = Se,
Compounds 94 through 96, each represented by the formula:
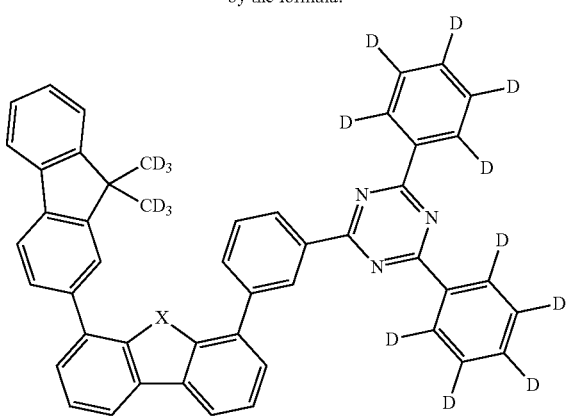
where in Compound 94: X = O,
in Compound 95, X = S, and
in Compound 96, X = Se and Compounds 97 through 99, each represented by the formula:

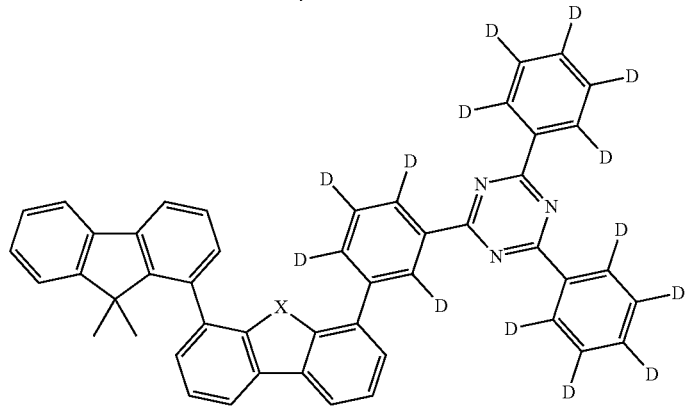

where in Compound 97: X = O,
in Compound 98, X = S, and
in Compound 99, X = Se.

According to another aspect of the present disclosure, a device that includes at least one organic light emitting device is also provided. At least one of the organic light emitting devices can include an anode, a cathode, and an organic layer disposed between the anode and the cathode. The organic layer can include one or more emitter dopants. The organic layer can include a compound according to Formula I, and its variations, as described herein. The compound according to Formula I can be a host and the organic layer can be an emissive layer.

In some embodiments, the organic layer further comprises an emissive dopant. In some embodiments, the emissive dopant is a transition metal complex having at least one ligand selected from the group consisting of:

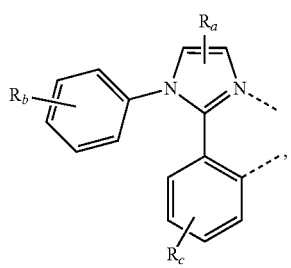

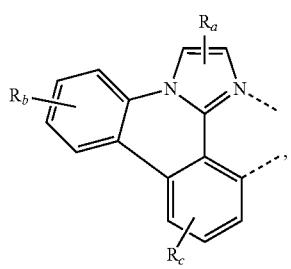

-continued

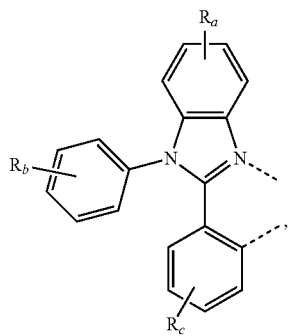

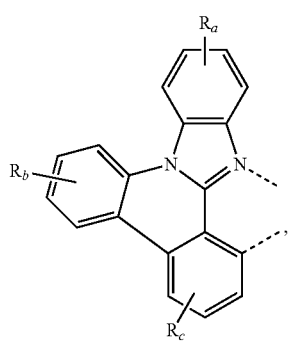

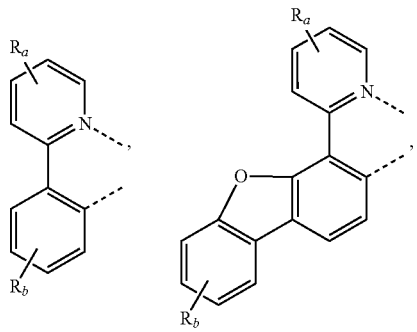

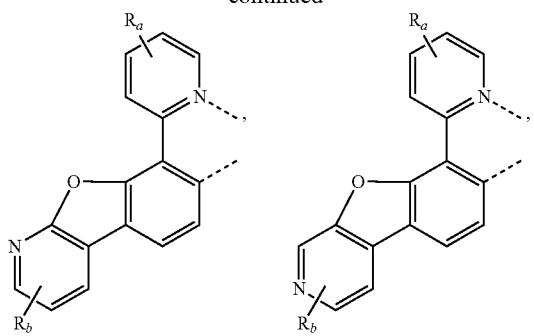
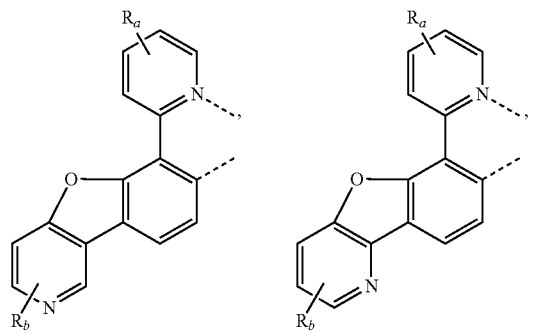
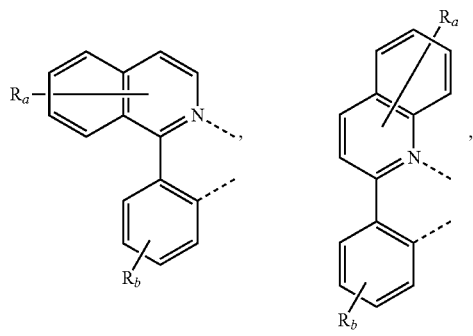
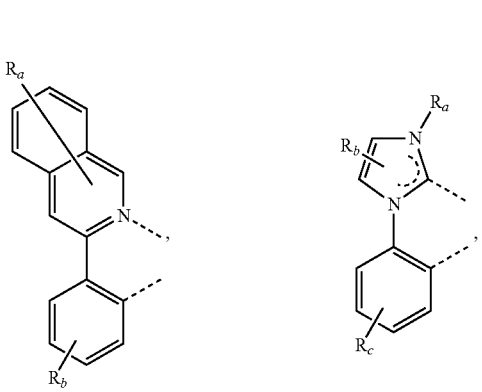
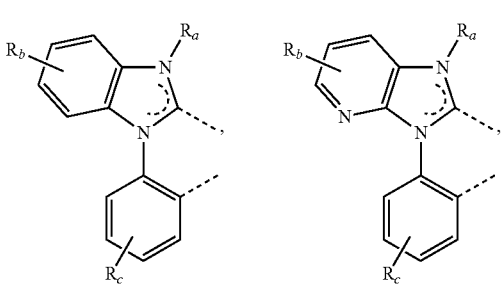
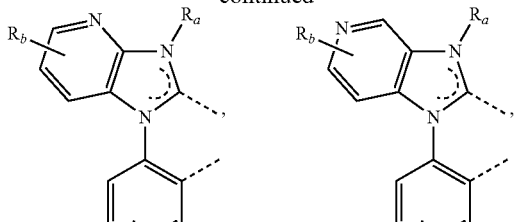
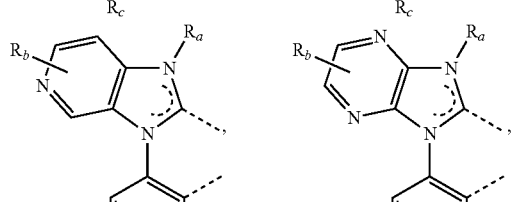
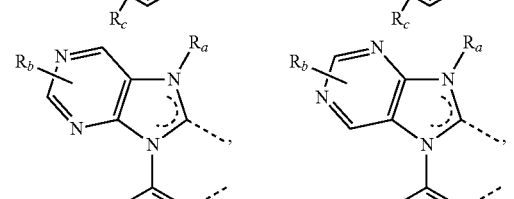
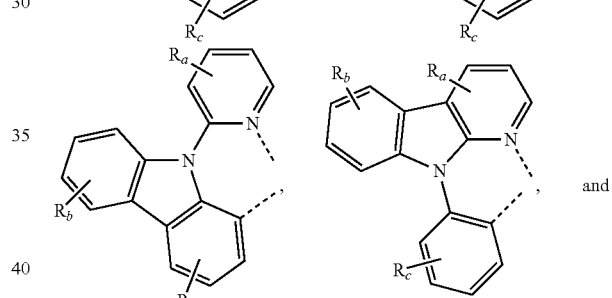
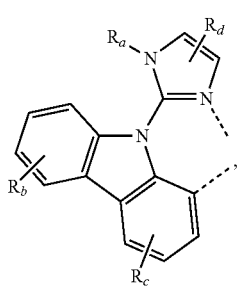

wherein $R_a$, $R_b$, $R_c$, and $R_d$ may represent mono, di, tri, or tetra substitution, or no substitution; wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

In some embodiments, the organic layer is a blocking layer and the compound having Formula I is a blocking material in the organic layer.

In some embodiments, the organic layer is an electron transporting layer and the compound having Formula I is an electron transporting material in the organic layer.

In some embodiments, the device is selected from the group consisting of a consumer product, an electronic component module, an organic light-emitting device, and a lighting panel.

In some embodiments, the organic layer comprises a first composition that includes a first compound and a second compound. In some embodiments, the first compound is a compound according to Formula I, and its variations, while the second compound has a structure of Formula III:

Formula III

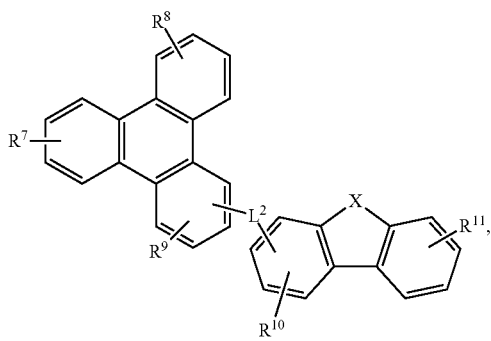

X is selected from the group consisting of S, O, Se, and NR', wherein $L^2$ is selected from a group consisting of direct bond, phenyl, biphenyl, terphenyl, fluorene, triphenylene, dibenzofuran, dibenzothiophene, dibenzoselenophene, carbazole and pyridine, and combinations thereof, wherein $L^2$ is optionally further substituted with one or more substituents selected from a group consisting of hydrogen, deuterium, alkyl, alkoxyl, cycloalkyl, cycloalkoxyl, halogen, nitro, nitrile, silyl, aryl, heteroaryl, and combinations thereof, wherein R', $R^7$, $R^8$, $R^9$, $R^{10}$ and $R^{11}$ are each an unfused substituent selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof, wherein $R^7$, $R^8$ and $R^{11}$ each independently represent mono, di, tri, or tetra substitution, or no substitution, and wherein $R^9$ and $R^{10}$ each independently represent mono, di, or tri substitution, or no substitution.

In some embodiments, R', $R^7$, $R^8$, $R^9$, $R^{10}$ and $R^{11}$ are each an unfused substituent selected from the group consisting of hydrogen, deuterium, alkyl, alkoxyl, cycloalkyl, cycloalkoxyl, halogen, nitro, nitrile, silyl, benzene, biphenyl, terphenyl, pyridine, and combinations thereof In yet another aspect of the present disclosure, a formulation that comprises a compound according to Formula I, and its variations, is described. The formulation can include one or more components selected from the group consisting of a solvent, a co-host, an emissive material, a hole injection material, hole transport material, and an electron transport layer material, disclosed herein.

Often, the emissive layer (EML) of OLED devices exhibiting good lifetime and efficiency requires more than two components (e.g., 3 or 4 components). In one example, the EML can include two host-type compounds and an emitter combination (e.g., a hole transporting co-host (h-host), an electron transporting co-host (e-host), and a compound capable of functioning as an emitter in an OLED at room temperature). In another example, the EML can consist of one host-type compound and two emitter-type compounds (e.g., a host compound and two compounds each capable of functioning as an emitter in an OLED at room temperature). Conventionally, in order to fabricate such EMLs having three or more components, the VTE process requires three or more evaporation sources, one for each of the components. Because the concentrations of the components are important for the device performance, typically, the rate of deposition of each component is measured and controlled individually during the deposition process. This makes the VTE process complicated and costly.

Premixing two or more materials and evaporating them from one VTE sublimation crucible reduces the complexity of the fabrication process. However, in a typical manufacturing process, multiple films are deposited with one single loading of the source materials. This single-source two-component co-evaporation must be stable and produce a composition that remains constant for all the evaporated films through the evaporation process, as variations in the film composition may adversely affect the device performance. In a stable co-evaporation, the ratio of the components in the mixture should be the same as the ratio of the components in the evaporation deposited films from these premixed materials. Therefore, the concentration of the two components in the deposited film is determined by their concentration in the premixed evaporation source.

In order to obtain a stable co-evaporation from a mixture of compounds under vacuum, one would assume that the materials must have the same evaporation temperature under the same conditions. However, this may not be the only parameter one has to consider. When two compounds are mixed together, they may interact with each other and the evaporation property of the mixture may differ from their individual properties. On the other hand, materials with slightly different evaporation temperatures may form a stable co-evaporation mixture. "Evaporation temperature" of a material is measured in a vacuum deposition tool at a constant pressure, normally between $1\times10^{-7}$ Torr to $1\times10^{-8}$ Torr, at a 2 Å/sec deposition rate on a surface positioned at a set distance away from the evaporation source of the material being evaporated, e.g., sublimation crucible in a VTE tool. The various measured values such as temperature, pressure, deposition rate, etc. disclosed herein are expected to have nominal variations because of the expected tolerances in the measurements that produced these quantitative values as understood by one of ordinary skill in the art.

Many factors other than temperature can contribute to the ability to achieve stable co-evaporation, such as the miscibility of the different materials and the phase transition temperatures of the different materials. The inventors found that when two materials have similar evaporation temperatures, and similar mass loss rate or similar vapor pressures, the two materials can co-evaporate consistently. "Mass loss rate" of a material is defined as the mass lost over time ("milligram/minute" or "mg/min") and is determined by measuring the isothermal weight loss of the sample material over a predetermined time span by thermal gravity analysis (TGA) at a given constant temperature under a set of predefined experimental conditions. The given constant temperature is one temperature point that is chosen so that the value of mass loss rate is between about 0.005 to 0.05 mg/min. A skilled person in this field should appreciate that in order to compare two parameters, the experimental condition should be consistent. The method of measuring mass loss rate and vapor pressure is well known in the art and can be found, for example, in Bull. et al. Mater. Sci. 2011, 34, 7.

In the state of the art OLED devices, the EML may consist of three or more components. If any two of the three or more components of the EMLs can be premixed and form a stable mixture of co-evaporation source, then the number of evaporation sources required for EML layer fabrication would be reduced. In order for materials to be premixable into an evaporation source, they should co-evaporate and deposit uniformly without changing the ratio. The ratio of the components in the mixture should be the same as the ratio of the components in the evaporation deposited films from these premixed materials. Therefore, the concentration of the two components in the deposited film is controlled by their concentration in the premixed evaporation source. Thus, it is desired to premix at least two of the components of such EMLs to reduce the number of VTE evaporation sources.

In some embodiments, this disclosure describes a new class of h- and e-hosts that can be premixed and stably co-evaporated from a single source.

In another aspect of the present disclosure, a composition comprising a first and second compound is described. The first compound can have a structure of Formula I and its variations as described herein, while the second compound can have a structure of Formula III:

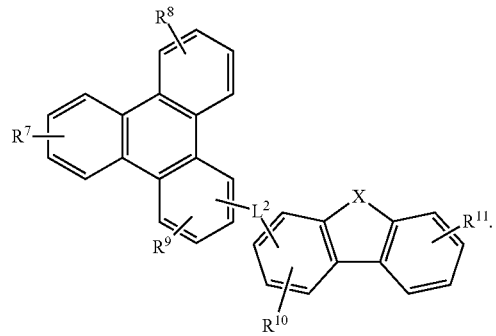

Formula III

In the structure of Formula III:

X is selected from the group consisting of S, O, Se, and NR', $L^2$ is selected from a group consisting of direct bond, phenyl, biphenyl, terphenyl, fluorene, triphenylene, dibenzofuran, dibenzothiophene, dibenzoselenophene, carbazole and pyridine, and combinations thereof, $L^2$ is optionally further substituted with one or more substituents selected from a group consisting of hydrogen, deuterium, alkyl, alkoxyl, cycloalkyl, cycloalkoxyl, halogen, nitro, nitrile, silyl, aryl, heteroaryl, and combinations thereof, R', $R^7$, $R^8$, $R^9$, $R^{10}$ and $R^{11}$ are each an unfused substituent selected from the group consisting of hydrogen, deuterium, alkyl, alkoxyl, cycloalkyl, cycloalkoxyl, halogen, nitro, nitrile, silyl, benzene, biphenyl, terphenyl, pyridine, and combinations thereof, $R^7$, $R^8$ and $R^{11}$ each independently represent mono, di, tri, or tetra substitution, or no substitution, and $R^9$ and $R^{10}$ each independently represent mono, di, or tri substitution, or no substitution.

In some embodiments, the second compound is selected from the group consisting of:

---

Compounds H1 through H3, each represented by the formula:

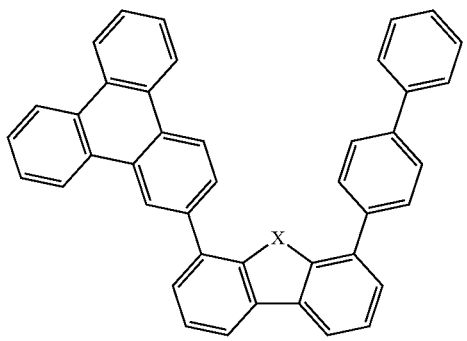

where in Compound H1: X = O, in Compound H2, X = S, and in Compound H3, X = Se,

Compounds H4 through H6, each represented by the formula:
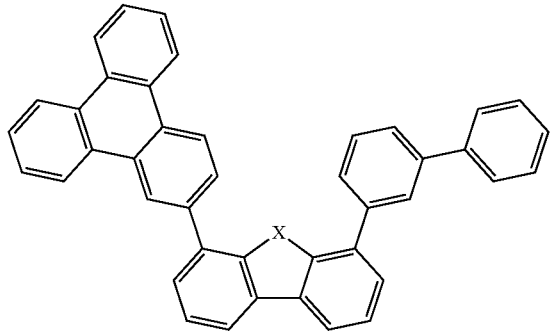
where in Compound H4: X = O,
in Compound H5, X = S, and
in Compound H6, X = Se,
Compounds H7 through H9, each represented by the formula:
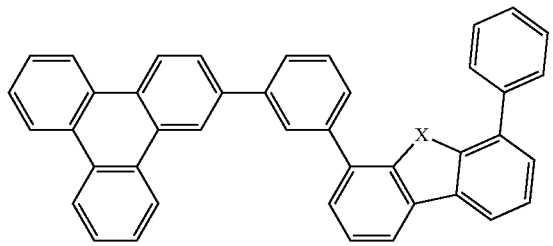
where in Compound H7: X = O,
in Compound H8, X = S, and
in Compound H9, X = Se,
Compounds H10 through H12, each represented by the formula:
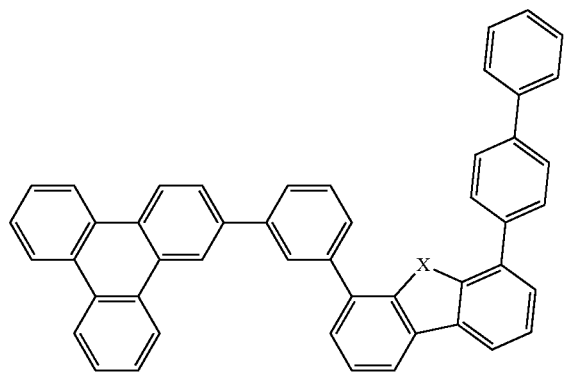
where in Compound H10: X = O,
in Compound H11, X = S, and
in Compound H12, X = Se, Compounds H13 through H15, each represented by the formula:
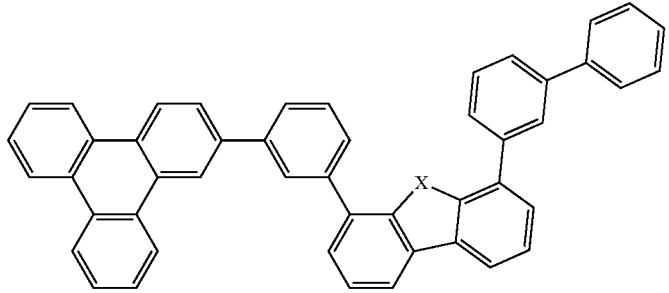
where in Compound H13: X = O,
in Compound H14, X = S, and
in Compound H15, X = Se,
Compounds H16 through H18, each represented by the formula:
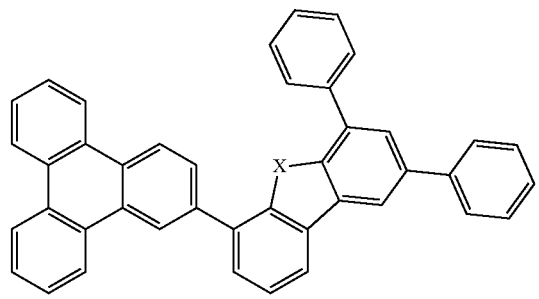
where in Compound H16: X = O,
in Compound H17, X = S, and
in Compound H18, X = Se,
Compounds H19 through H21, each represented by the formula:
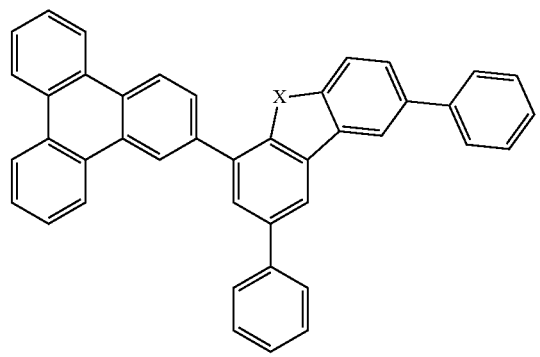
where in Compound H19: X = O,
in Compound H20, X = S, and
in Compound H21, X = Se, Compounds H22 through H24, each represented by the formula:

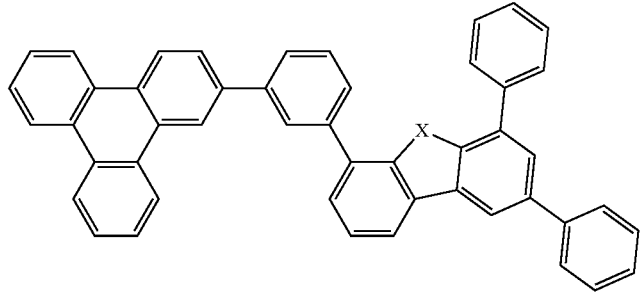

where in Compound H22: X = O,
in Compound H23, X = S, and
in Compound H24, X = Se, Compounds H25 through H27, each represented by the formula:

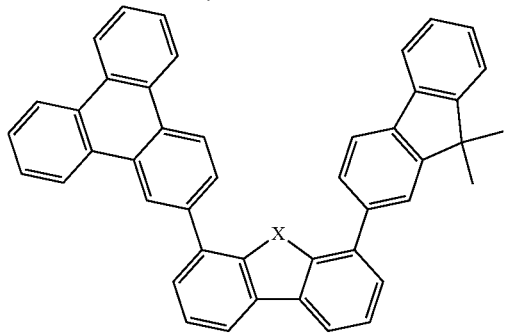

where in Compound H25: X = O,
in Compound H26, X = S, and
in Compound H27, X = Se and Compounds H28 through H30, each represented by the formula:

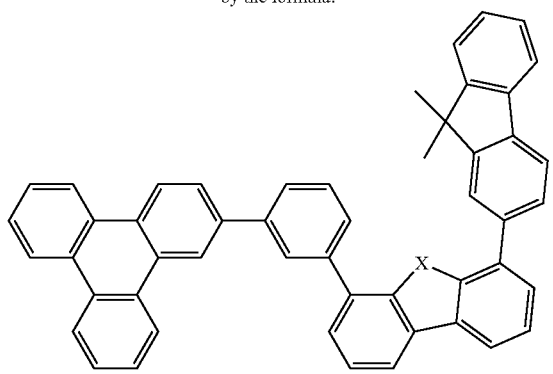

where in Compound H28: X = O,
in Compound H29, X = S, and
in Compound H30, X = Se.

In some embodiments, the composition comprises at least one compound selected from compound 1 through compound 99, and at least one compound selected from compound H1 through compound H30. In some embodiments, the composition is selected from CP1 through CP10, as described below:

| Compositions | First compound | Second compound |
| --- | --- | --- |
| CP1 | Compound 2 | Compound H2 |
| CP2 | Compound 2 | Compound H5 |
| CP3 | Compound 2 | Compound H8 |
| CP4 | Compound 2 | Compound H17 |

-continued

| Compositions | First compound | Second compound |
|---|---|---|
| CP5 | Compound 2 | Compound H26 |
| CP6 | Compound 5 | Compound H11 |
| CP7 | Compound 5 | Compound H14 |
| CP8 | Compound 5 | Compound H29 |
| CP9 | Compound 65 | Compound H2 |
| CP10 | Compound 65 | Compound H5 |

In some embodiments, the first compound has an evaporation temperature T1 of 150 to 350° C.; the second compound has an evaporation temperature T2 of 150 to 350° C.; the absolute value of T1−T2 is less than 20° C.; the first compound has a concentration C1 in said mixture and a concentration C2 in a film formed by evaporating the mixture in a vacuum deposition tool at a constant pressure between $1\times10^{-6}$ Torr to $1\times10^{-9}$ Torr, at a 2 Å/sec deposition rate on a surface positioned at a predefined distance away from the mixture being evaporated; and the absolute value of (C1−C2)/C1 is less than 5%. In some embodiments, the absolute value of (C1−C2)/C1 is less than 3%.

In some embodiments, the first compound has evaporation temperature T1 of 200 to 350° C. and the second compound has evaporation temperature T2 of 200 to 350° C. In some embodiments, the composition is in liquid form at a temperature less than T1 and T2.

In some embodiments, the first compound has a vapor pressure of P1 at T1 at 1 atm, the second compound has a vapor pressure of P2 at T2 at 1 atm; and the ratio of P1/P2 is within the range of 0.90 to 1.10.

In some embodiments, the first compound has a first mass loss rate and the second compound has a second mass loss rate, and the ratio between the first mass loss rate and the second mass loss rate is within the range of 0.90 to 1.10. In some embodiments, the ratio between the first mass loss rate and the second mass loss rate is within the range of 0.95 to 1.05. In some embodiments, the ratio between the first mass loss rate and the second mass loss rate is within the range of 0.97 to 1.03.

In some embodiments, the first compound and the second compound each has a purity in excess of 99% as determined by high pressure liquid chromatography.

In some embodiments, the composition further comprises a third compound, where the third compound has a different chemical structure than the first and second compounds, the third compound has an evaporation temperature T3 of 150 to 350° C., and where the absolute value of T1−T3 is less than 20° C. In some embodiments comprising a third compound different from the first and second compounds, the third compound has a third mass loss rate, and the ratio between the first mass loss rate and third mass loss rate is within the range of 0.90 to 1.10.

In another aspect of the present disclosure, a method for fabricating an organic light emitting device comprising a first electrode, a second electrode, and a first organic layer disposed between the first electrode and the second electrode, where the first organic layer comprises a first composition comprising a mixture of a first compound and a second compound is described. The method includes providing a substrate having the first electrode disposed thereon; depositing the first composition over the first electrode; and depositing the second electrode over the first organic layer. The depositing step can be implemented using a chemical vapor deposition technique (e.g., vacuum thermal evaporation). The first compound can have a structure of Formula I and its variations as described herein, while the second compound can have a structure of Formula III, and its variations as described herein.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

HIL/HTL:

A hole injecting/transporting material to be used in the present invention is not particularly limited, and any compound may be used as long as the compound is typically used as a hole injecting/transporting material. Examples of the material include, but are not limited to: a phthalocyanine or porphyrin derivative; an aromatic amine derivative; an indolocarbazole derivative; a polymer containing fluorohydrocarbon; a polymer with conductivity dopants; a conducting polymer, such as PEDOT/PSS; a self-assembly monomer derived from compounds such as phosphonic acid and silane derivatives; a metal oxide derivative, such as $MoO_x$; a p-type semiconducting organic compound, such as 1,4,5,8,9,12-Hexaazatriphenylenehexacarbonitrile; a metal complex, and a cross-linkable compound.

Examples of aromatic amine derivatives used in HIL or HTL include, but are not limited to the following general structures:

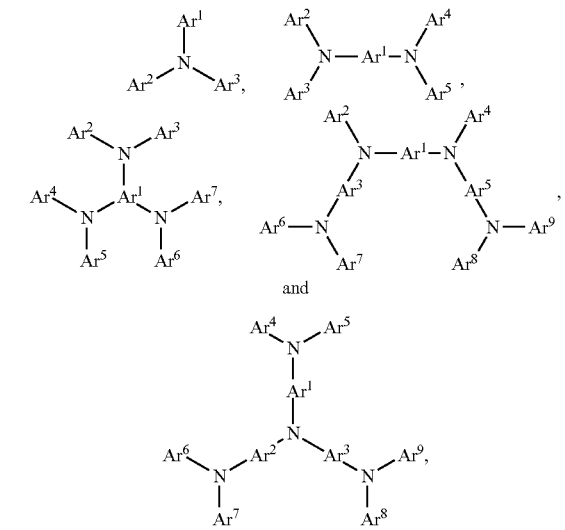

Each of $Ar^1$ to $Ar^9$ is selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each Ar is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, $Ar^1$ to $Ar^9$ is independently selected from the group consisting of:

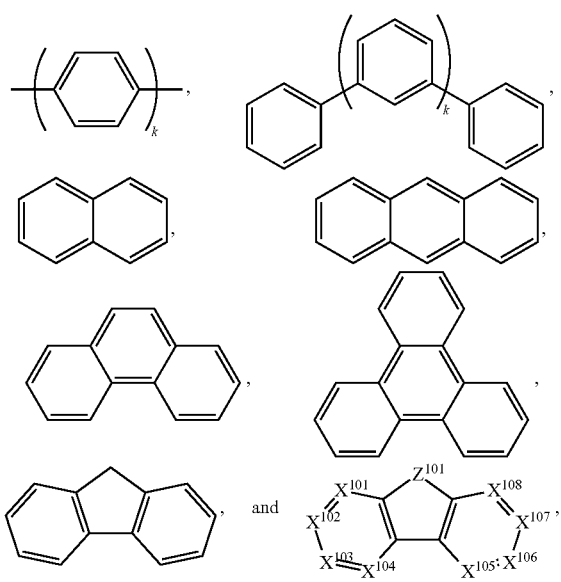

wherein k is an integer from 1 to 20; $X^{101}$ to $X^{108}$ is C (including CH) or N; $Z^{101}$ is $NAr^1$, O, or S; $Ar^1$ has the same group defined above.

Examples of metal complexes used in HIL or HTL include, but not are limited to the following general formula:

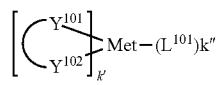

wherein Met is a metal, which can have an atomic weight greater than 40; $(Y^{101}\text{-}Y^{102})$ is a bidentate ligand, $Y^{101}$ and $Y^{102}$ are independently selected from C, N, O, P, and S; $L^{101}$ is an ancillary ligand; k' is an integer value from 1 to the maximum number of ligands that may be attached to the metal; and k'+k" is the maximum number of ligands that may be attached to the metal.

In one aspect, $(Y^{101}\text{-}Y^{102})$ is a 2-phenylpyridine derivative. In another aspect, $(Y^{101}\text{-}Y^{102})$ is a carbene ligand. In another aspect, Met is selected from Ir, Pt, Os, and Zn. In a further aspect, the metal complex has a smallest oxidation potential in solution vs. $Fc^+/Fc$ couple less than about 0.6 V.

Host:

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. While the Table below categorizes host materials as preferred for devices that emit various colors, any host material may be used with any dopant so long as the triplet criteria is satisfied.

Examples of metal complexes used as host are preferred to have the following general formula:

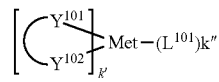

wherein Met is a metal; $(Y^{103}\text{-}Y^{104})$ is a bidentate ligand, $Y^{103}$ and $Y^{104}$ are independently selected from C, N, O, P, and S; $L^{101}$ is an another ligand; k' is an integer value from 1 to the maximum number of ligands that may be attached to the metal; and k'+k" is the maximum number of ligands that may be attached to the metal.

In one aspect, the metal complexes are:

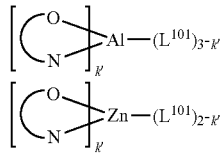

wherein (O—N) is a bidentate ligand, having metal coordinated to atoms O and N.

In another aspect, Met is selected from Ir and Pt. In a further aspect, $(Y^{103}\text{-}Y^{104})$ is a carbene ligand.

Examples of organic compounds used as host are selected from the group consisting of aromatic hydrocarbon cyclic compounds such as benzene, biphenyl, triphenyl, triphenylene, naphthalene, anthracene, phenalene, phenanthrene, fluorene, pyrene, chrysene, perylene, and azulene; the group consisting of aromatic heterocyclic compounds such as dibenzothiophene, dibenzofuran, dibenzoselenophene, furan, thiophene, benzofuran, benzothiophene, benzoselenophene, carbazole, indolocarbazole, pyridylindole, pyrrolodipyridine, pyrazole, imidazole, triazole, oxazole, thiazole, oxadiazole, oxatriazole, dioxazole, thiadiazole, pyridine, pyridazine, pyrimidine, pyrazine, triazine, oxazine, oxathiazine, oxadiazine, indole, benzimidazole, indazole, indoxazine, benzoxazole, benzisoxazole, benzothiazole, quinoline, isoquinoline, cinnoline, quinazoline, quinoxaline, naphthyridine, phthalazine, pteridine, xanthene, acridine, phenazine, phenothiazine, phenoxazine, benzofuropyridine, furodipyridine, benzothienopyridine, thienodipyridine, benzoselenophenopyridine, and selenophenodipyridine; and the group consisting of 2 to 10 cyclic structural units which are groups of the same type or different types selected from the aromatic hydrocarbon cyclic group and the aromatic heterocyclic group and are bonded to each other directly or via at least one of oxygen atom, nitrogen atom, sulfur atom, silicon atom, phosphorus atom, boron atom, chain structural unit and the aliphatic cyclic group. Wherein each group is further substituted by a substituent selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof.

In one aspect, host compound contains at least one of the following groups in the molecule:

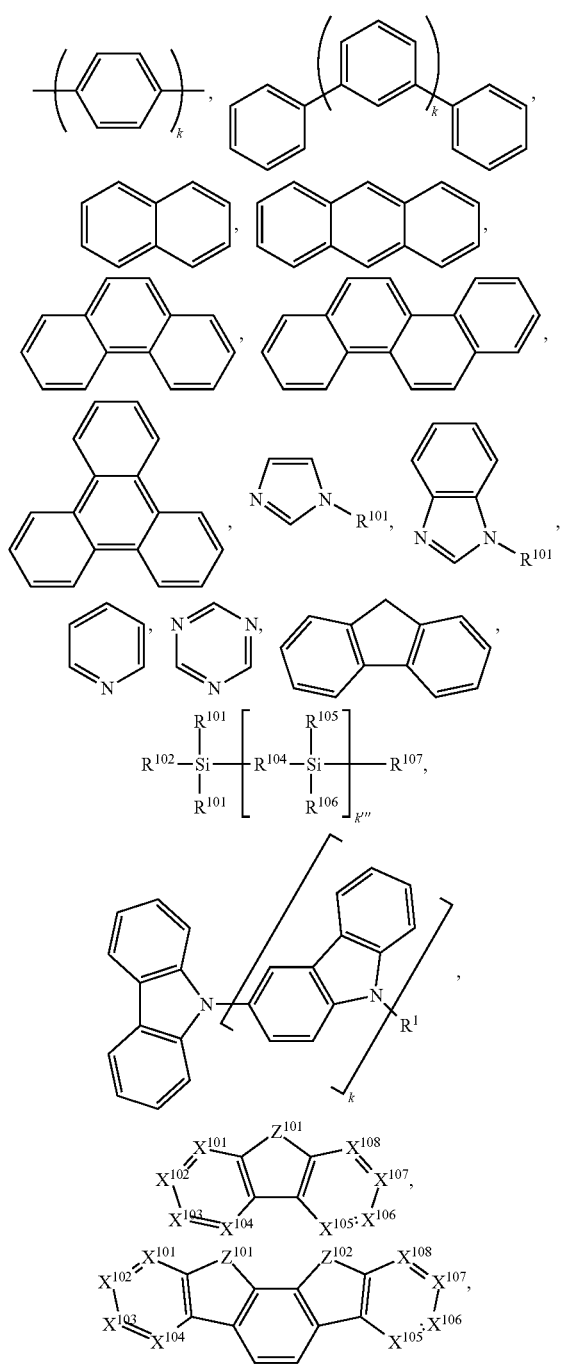

wherein $R^{101}$ to $R^{107}$ is independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. k is an integer from 0 to 20 or 1 to 20: k' is an integer from 0 to 20. $X^{101}$ to $X^{108}$ is selected from C (including CH) or N. $Z^{101}$ and $Z^{102}$ is selected from $NR^{101}$, O, or S.

HBL:

A hole blocking layer (HBL) may be used to reduce the number of holes and/or excitons that leave the emissive layer. The presence of such a blocking layer in a device may result in substantially higher efficiencies as compared to a similar device lacking a blocking layer. Also, a blocking layer may be used to confine emission to a desired region of an OLED.

In one aspect, compound used in HBL contains the same molecule or the same functional groups used as host described above.

In another aspect, compound used in HBL contains at least one of the following groups in the molecule:

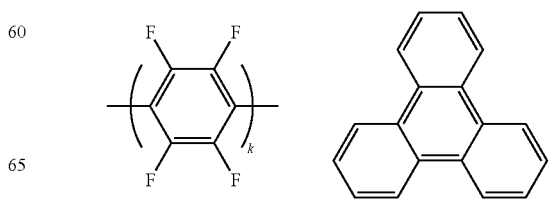

-continued

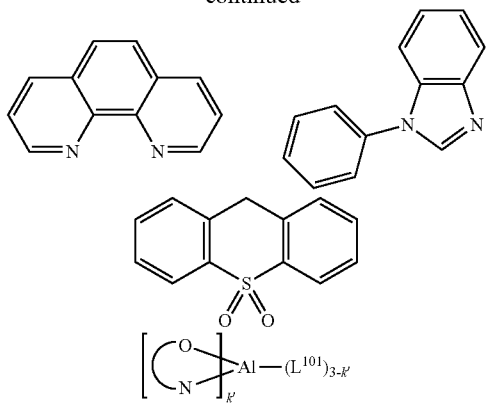

wherein k is an integer from 1 to 20; $L^{101}$ is an another ligand, k' is an integer from 1 to 3.

ETL:

Electron transport layer (ETL) may include a material capable of transporting electrons. Electron transport layer may be intrinsic (undoped), or doped. Doping may be used to enhance conductivity. Examples of the ETL material are not particularly limited, and any metal complexes or organic compounds may be used as long as they are typically used to transport electrons.

In one aspect, compound used in ETL contains at least one of the following groups in the molecule:

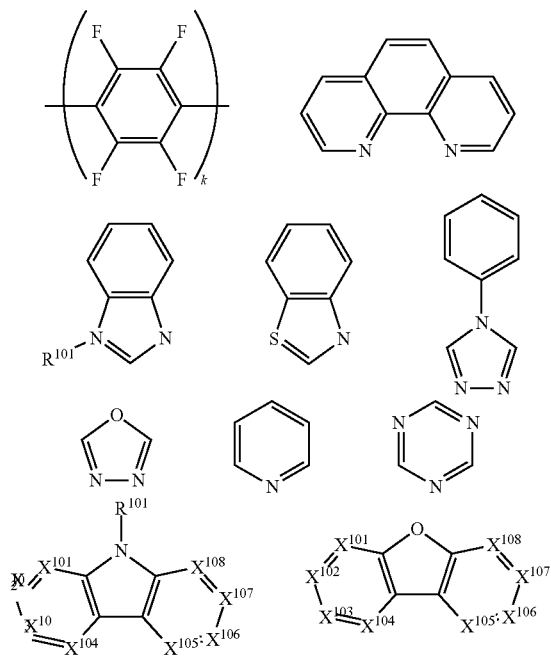

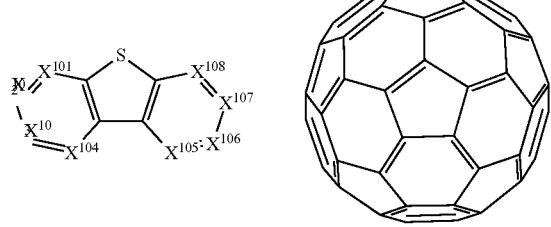

-continued

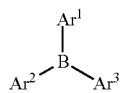

wherein $R^{101}$ is selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof, when it is aryl or heteroaryl, it has the similar definition as Ar's mentioned above. $Ar^1$ to $Ar^3$ has the similar definition as Ar's mentioned above. k is an integer from 1 to 20. $X^{101}$ to $X^{108}$ is selected from C (including CH) or N.

In another aspect, the metal complexes used in ETL include, but are not limited to the following general formula:

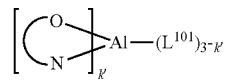

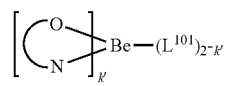

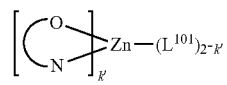

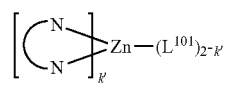

wherein (O—N) or (N—N) is a bidentate ligand, having metal coordinated to atoms O, N or N, N; $L^{101}$ is another ligand; k' is an integer value from 1 to the maximum number of ligands that may be attached to the metal.

In any above-mentioned compounds used in each layer of the OLED device, the hydrogen atoms can be partially or fully deuterated. Thus, any specifically listed substituent, such as, without limitation, methyl, phenyl, pyridyl, etc. encompasses undeuterated, partially deuterated, and fully deuterated versions thereof. Similarly, classes of substituents such as, without limitation, alkyl, aryl, cycloalkyl, heteroaryl, etc. also encompass undeuterated, partially deuterated, and fully deuterated versions thereof.

In addition to and/or in combination with the materials disclosed herein, many hole injection materials, hole transporting materials, host materials, dopant materials, exciton/hole blocking layer materials, electron transporting and electron injecting materials may be used in an OLED. Non-limiting examples of the materials that may be used in an OLED in combination with materials disclosed herein are listed in Table A below. Table A lists non-limiting classes of materials, non-limiting examples of compounds for each class, and references that disclose the materials.

TABLE A

| MATERIAL | EXAMPLES OF MATERIAL | PUBLICATIONS |
|---|---|---|
| Hole injection materials | | |
| Phthalocyanine and porphryin compounds | 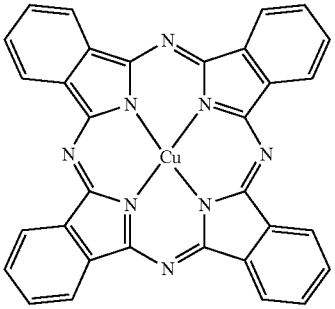 | Appl. Phys. Lett. 69, 2160 (1996) |
| Starburst triarylamines | 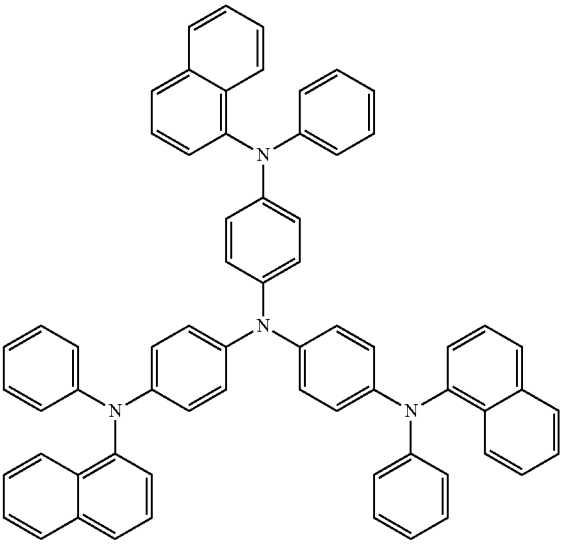 [SMILES: c1ccc(N(c2ccc(N(c3ccc(N(c4ccccc4)c4cccc5ccccc45)cc3)c3ccc(N(c4ccccc4)c4cccc5ccccc45)cc3)cc2)c2cccc3ccccc23)cc1] | J. Lumin. 72-74, 985 (1997) |
| $CF_x$ Fluorohydrocarbon polymer | $-[CH_xF_y]_n-$ | Appl. Phys. Lett. 78, 673 (2001) |
| Conducting polymers (e.g., PEDOT:PSS, polyaniline, polythiophene) | 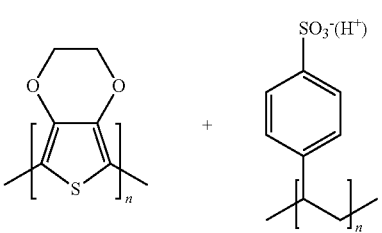 | Synth. Met. 87, 171 (1997) WO2007002683 |
| Phosphonic acid and silane SAMs | 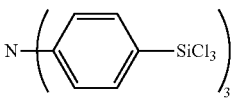 | US20030162053 |
| Triarylamine or polythiophene polymers with conductivity dopants | 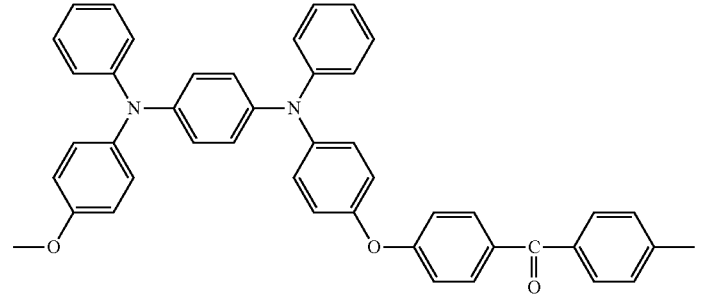 and | EP1725079A1 |

TABLE A-continued
| MATERIAL | EXAMPLES OF MATERIAL | PUBLICATIONS |
|---|---|---|
| | 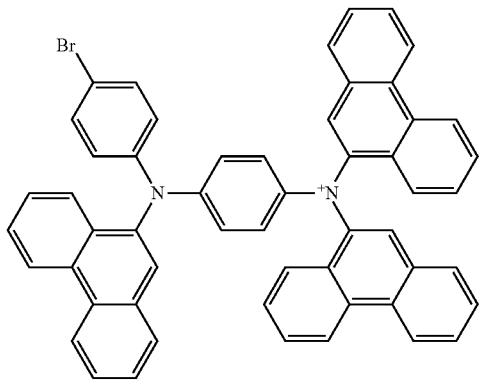 [SMILES: Brc1ccc(N(c2ccc([NH+](c3cc4ccccc4c4ccccc34)c3cc4ccccc4c4ccccc34)cc2)c2cc3ccccc3c3ccccc23)cc1] | |
| | 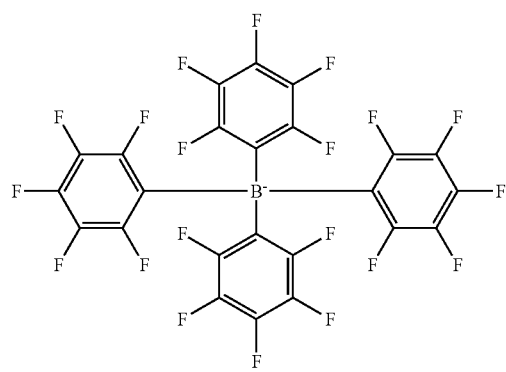 [SMILES: Fc1c(F)c(F)c([B-](c2c(F)c(F)c(F)c(F)c2F)(c2c(F)c(F)c(F)c(F)c2F)c2c(F)c(F)c(F)c(F)c2F)c(F)c1F] | |
| Organic compounds with conductive inorganic compounds, such as molybdenum and tungsten oxides | 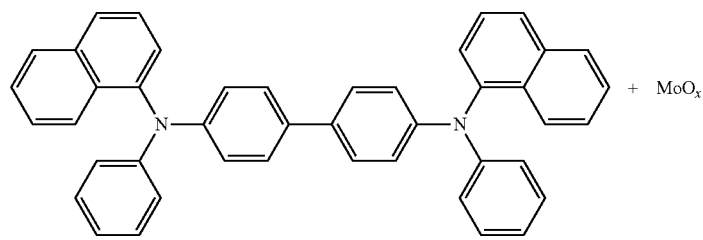 [SMILES: c1ccc(N(c2ccc(-c3ccc(N(c4ccccc4)c4cccc5ccccc45)cc3)cc2)c2cccc3ccccc23)cc1] | US20050123751 SID Symposium Digest, 37, 923 (2006) WO2009018009 |
| n-type semiconducting organic complexes | 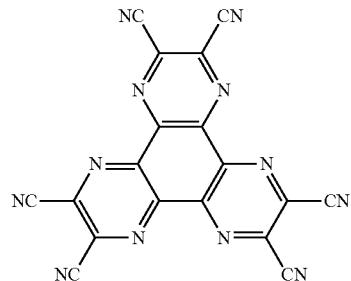 [SMILES: N#Cc1nc2c3nc(C#N)c(C#N)nc3c3nc(C#N)c(C#N)nc3c2nc1C#N] | US20020158242 |
| Metal organometallic complexes | 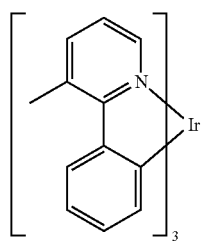 | US20060240279 |

| MATERIAL | EXAMPLES OF MATERIAL | PUBLICATIONS |
|---|---|---|
| Cross-linkable compounds | 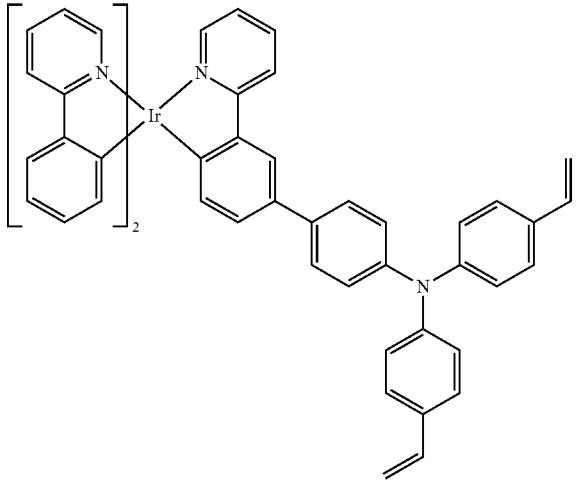 | US20080220265 |
| Polythiophene based polymers and copolymers | 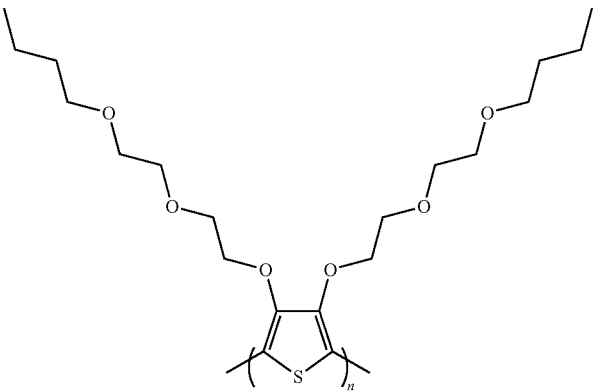 | WO 2011075644<br>EP2350216 |
Hole transporting materials
| | | |
|---|---|---|
| Triarylamines (e.g., TPD, α-NPD) | 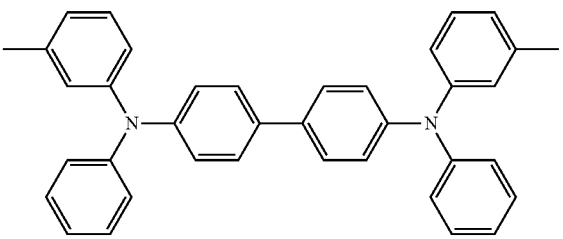 | Appl. Phys. Lett. 51, 913 (1987) |
| | 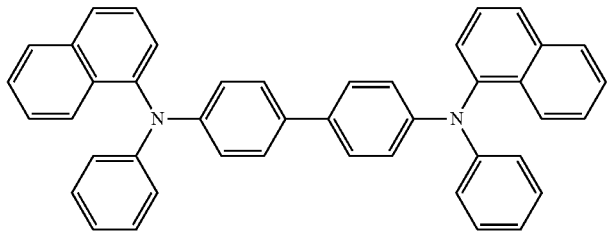 [SMILES: c1ccc(N(c2ccc(-c3ccc(N(c4ccccc4)c4cccc5ccccc45)cc3)cc2)c2cccc3ccccc23)cc1] | U.S. Pat. No. 5,061,569 |

TABLE A-continued
| MATERIAL | EXAMPLES OF MATERIAL | PUBLICATIONS |
|---|---|---|
| | 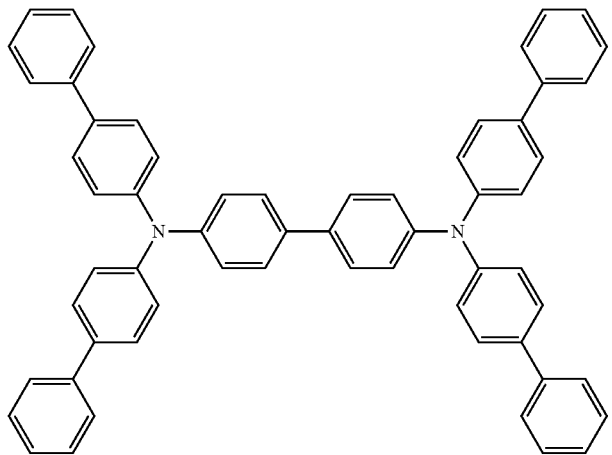 [SMILES: c1ccc(-c2ccc(N(c3ccc(-c4ccccc4)cc3)c3ccc(-c4ccc(N(c5ccc(-c6ccccc6)cc5)c5ccc(-c6ccccc6)cc5)cc4)cc3)cc2)cc1] | EP650955 |
| | 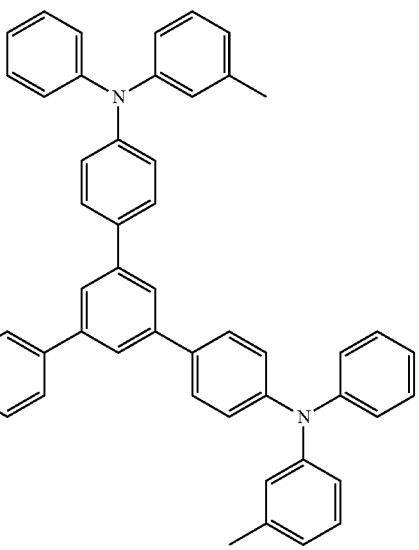 | J. Mater. Chem. 3, 319 (1993) |
| | 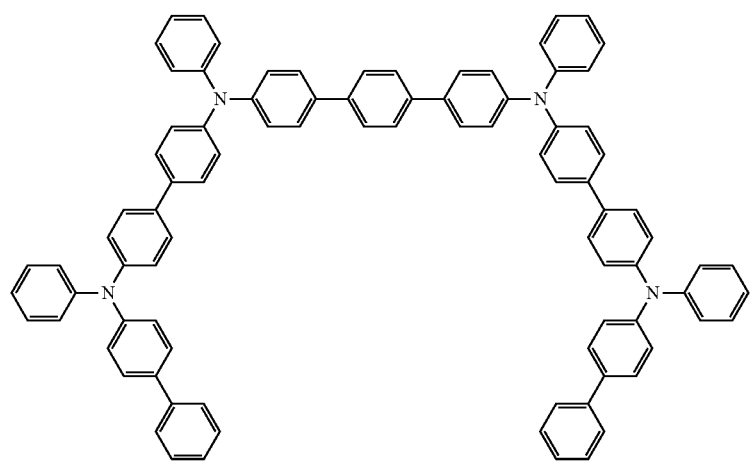 [SMILES: c1ccc(-c2ccc(N(c3ccccc3)c3ccc(-c4ccc(N(c5ccccc5)c5ccc(-c6ccc(-c7ccc(N(c8ccccc8)c8ccc(-c9ccc(N(c%10ccccc%10)c%10ccc(-c%11ccccc%11)cc%10)cc9)cc8)cc7)cc6)cc5)cc4)cc3)cc2)cc1] | Appl. Phys. Lett. 90, 183503 (2007) |

TABLE A-continued
| MATERIAL | EXAMPLES OF MATERIAL | PUBLICATIONS |
|---|---|---|
| | 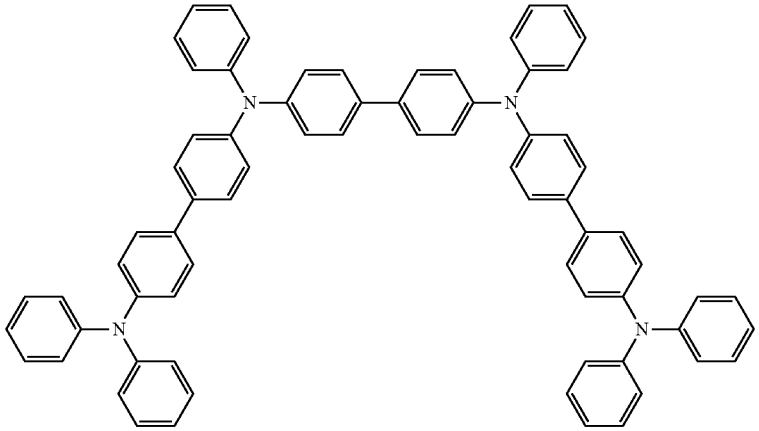 [SMILES: c1ccc(N(c2ccccc2)c2ccc(-c3ccc(N(c4ccccc4)c4ccc(-c5ccc(N(c6ccccc6)c6ccc(-c7ccc(N(c8ccccc8)c8ccccc8)cc7)cc6)cc5)cc4)cc3)cc2)cc1] | Appl. Phys. Lett. 90, 183503 (2007) |
| Triarylamine on spirofluorene core | 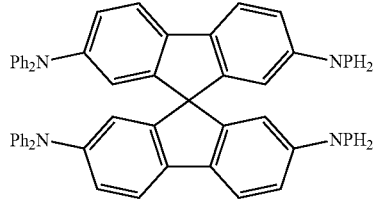 | Synth. Met. 91, 209 (1997) |
| Arylamine carbazole compounds | 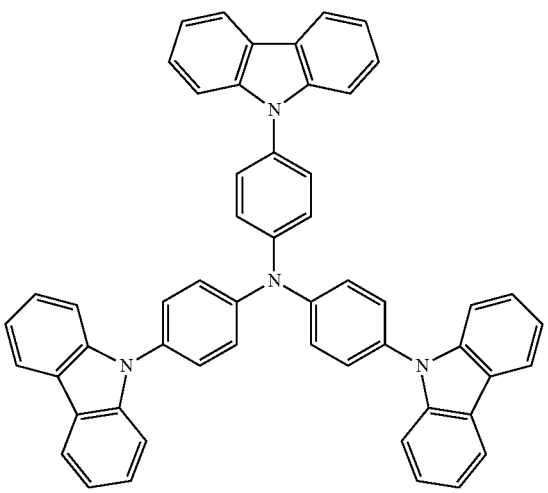 [SMILES: c1ccc2c(c1)c1ccccc1n2-c1ccc(N(c2ccc(-n3c4ccccc4c4ccccc43)cc2)c2ccc(-n3c4ccccc4c4ccccc43)cc2)cc1] | Adv. Mater. 6, 677 (1994), US20080124572 |
| Triarylamine with (di)benzothiophene/ (di)benzofuran | 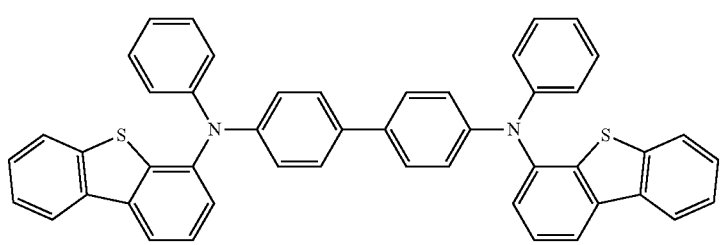 [SMILES: c1ccc(N(c2ccc(-c3ccc(N(c4ccccc4)c4cccc5c4sc4ccccc45)cc3)cc2)c2cccc3c2sc2ccccc23)cc1] | US20070278938, US20080106190 US20110163302 |

TABLE A-continued

| MATERIAL | EXAMPLES OF MATERIAL | PUBLICATIONS |
| --- | --- | --- |
| Indolocarbazoles | | Synth. Met. 111, 421 (2000) |
| Isoindole compounds | | Chem. Mater. 15, 3148 (2003) |
| Metal carbene complexes | | US20080018221 |

Phosphorescent OLED host materials
Red hosts

| | | |
| --- | --- | --- |
| Arylcarbazoles | | Appl. Phys. Lett. 78, 1622 (2001) |

TABLE A-continued
| MATERIAL | EXAMPLES OF MATERIAL | PUBLICATIONS |
|---|---|---|
| Metal 8-hydroxyquinolates (e.g., Alq$_3$, BAlq) | 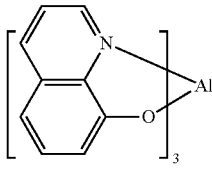 | Nature 395, 151 (1998) |
| | 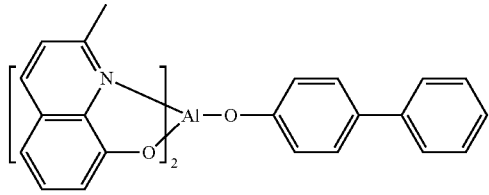 | US20060202194 |
| | 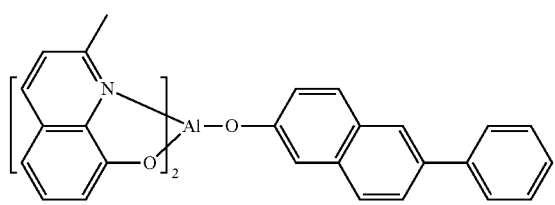 | WO2005014551 |
| | 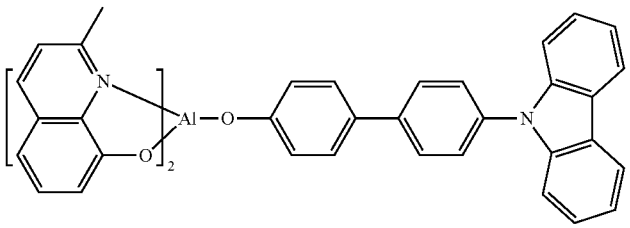 | WO2006072002 |
| Metal phenoxybenzothiazole compounds | 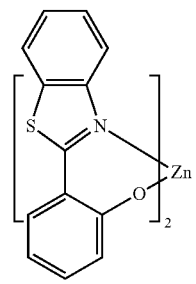 | Appl. Phys. Lett. 90, 123509 (2007) |
| Conjugated oligomers and polymers (e.g., polyfluorene) | 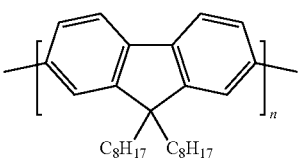 | Org. Electron. 1, 15 (2000) |
| Aromatic fused rings | 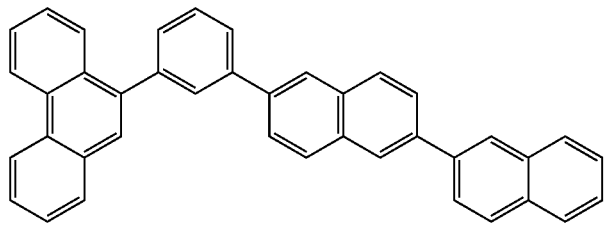 [SMILES: c1cc(-c2ccc3cc(-c4ccc5ccccc5c4)ccc3c2)cc(-c2cc3ccccc3c3ccccc23)c1] | WO2009066779, WO2009066778, WO2009063833, US20090045731, US20090045730, WO2009008311, US20090008605, US20090009065 |

TABLE A-continued
| MATERIAL | EXAMPLES OF MATERIAL | PUBLICATIONS |
|---|---|---|
| Zinc complexes | 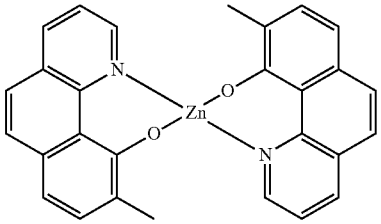 | WO2010056066 |
| Chrysene based compounds | 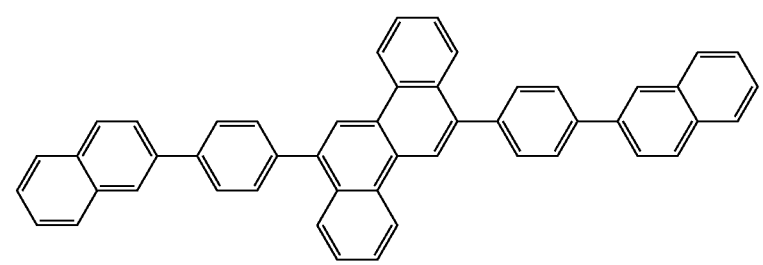 [SMILES: c1ccc2cc(-c3ccc(-c4cc5c6ccccc6c(-c6ccc(-c7ccc8ccccc8c7)cc6)cc5c5ccccc45)cc3)ccc2c1] | WO2011086863 |
Green hosts
| | | |
|---|---|---|
| Arylcarbazoles | 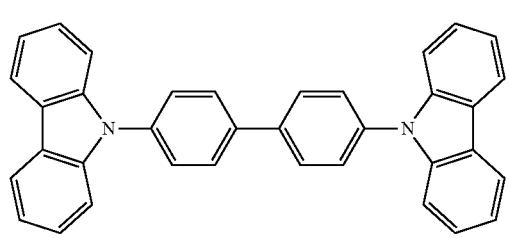 [SMILES: c1ccc2c(c1)c1ccccc1n2-c1ccc(-c2ccc(-n3c4ccccc4c4ccccc43)cc2)cc1] | Appl. Phys. Lett. 78, 1622 (2001) |
| | 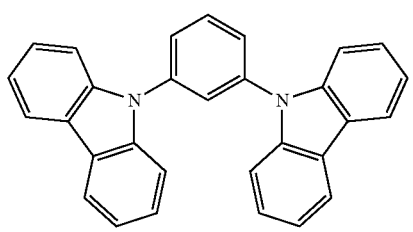 [SMILES: c1cc(-n2c3ccccc3c3ccccc32)cc(-n2c3ccccc3c3ccccc32)c1] | US20030175553 |
| | 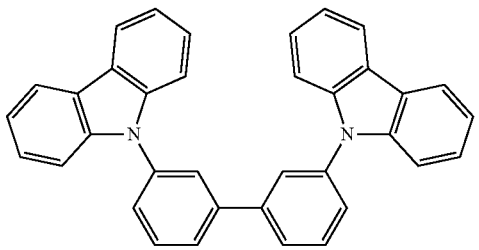 [SMILES: c1cc(-c2cccc(-n3c4ccccc4c4ccccc43)c2)cc(-n2c3ccccc3c3ccccc32)c1] | WO2001039234 |
| Aryltriphenylene compounds | 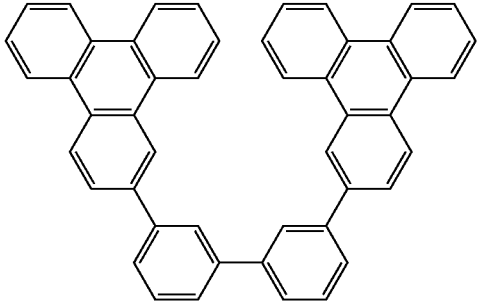 [SMILES: c1cc(-c2cccc(-c3ccc4c5ccccc5c5ccccc5c4c3)c2)cc(-c2ccc3c4ccccc4c4ccccc4c3c2)c1] | US20060280965 |

TABLE A-continued
| MATERIAL | EXAMPLES OF MATERIAL | PUBLICATIONS |
|---|---|---|
| | 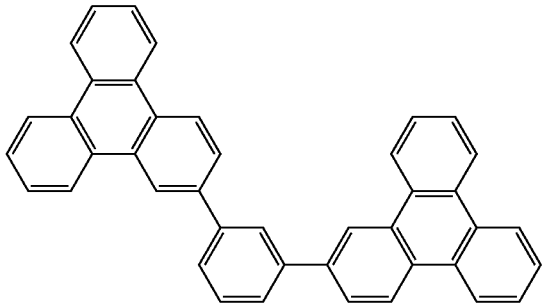 [SMILES: c1cc(-c2ccc3c4ccccc4c4ccccc4c3c2)cc(-c2ccc3c4ccccc4c4ccccc4c3c2)c1] | US20060280965 |
| | 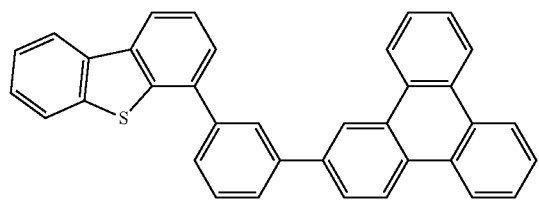 [SMILES: c1cc(-c2ccc3c4ccccc4c4ccccc4c3c2)cc(-c2cccc3c2sc2ccccc23)c1] | WO2009021126 |
| Poly-fused heteroaryl compounds | 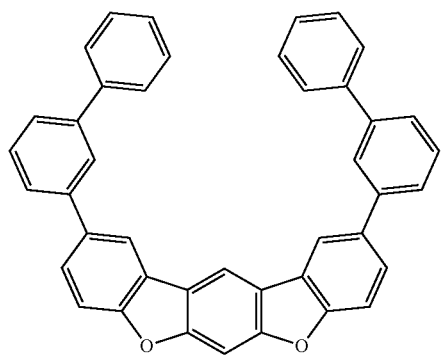 [SMILES: c1ccc(-c2cccc(-c3ccc4oc5cc6oc7ccc(-c8cccc(-c9ccccc9)c8)cc7c6cc5c4c3)c2)cc1] | US20090309488<br>US20090302743<br>US20100012931 |
| Donor acceptor type molecules | 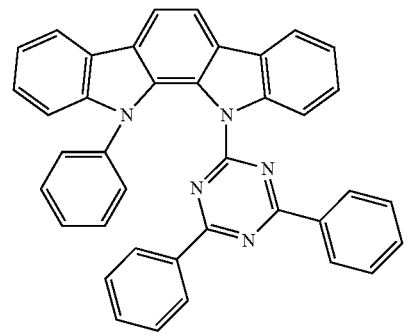 [SMILES: c1ccc(-c2nc(-c3ccccc3)nc(-n3c4ccccc4c4ccc5c6ccccc6n(-c6ccccc6)c5c43)n2)cc1] | WO2008056746 |
| | 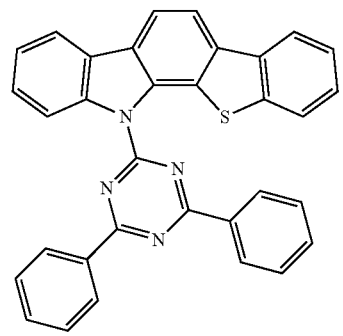 [SMILES: c1ccc(-c2nc(-c3ccccc3)nc(-n3c4ccccc4c4ccc5c6ccccc6sc5c43)n2)cc1] | WO2010107244 |

TABLE A-continued

| MATERIAL | EXAMPLES OF MATERIAL | PUBLICATIONS |
|---|---|---|
| Aza-carbazole/DBT/DBF | | JP2008074939 |
| | | US20100187984 |
| Polymers (e.g., PVK) | | Appl. Phys. Lett. 77, 2280 (2000) |
| Spirofluorene compounds | | WO2004093207 |
| Metal phenoxybenzooxazole compounds | | WO2005089025 |

| MATERIAL | EXAMPLES OF MATERIAL | PUBLICATIONS |
|---|---|---|
| | 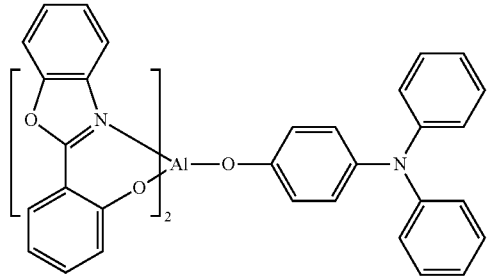 | WO2006132173 |
| | 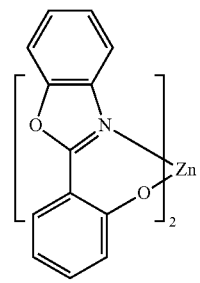 | JP200511610 |
| Spirofluorene-carbazole compounds | 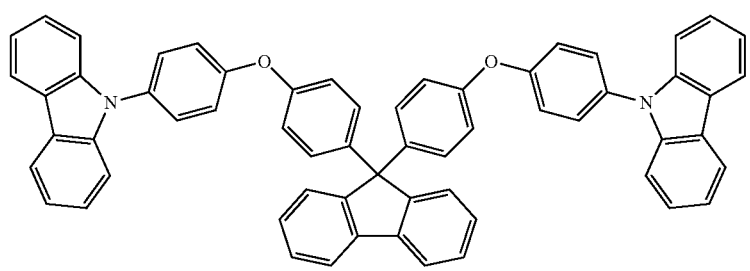 [SMILES: c1ccc2c(c1)-c1ccccc1C2(c1ccc(Oc2ccc(-n3c4ccccc4c4ccccc43)cc2)cc1)c1ccc(Oc2ccc(-n3c4ccccc4c4ccccc43)cc2)cc1] | JP2007254297 |
| | 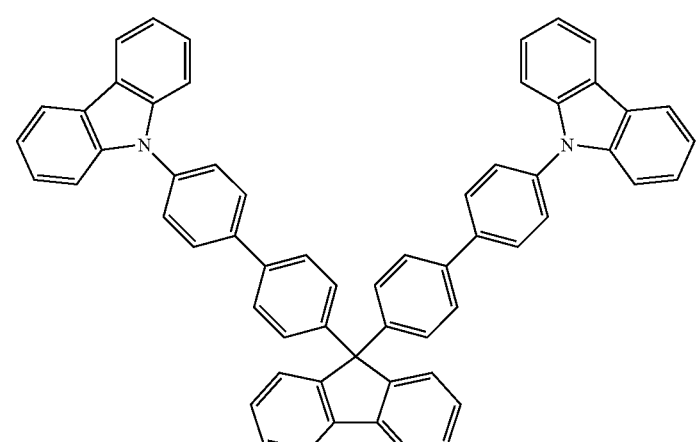 | JP2007254297 |
| Indolocarbazoles | 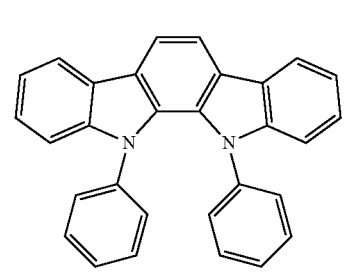 [SMILES: c1ccc(-n2c3ccccc3c3ccc4c5ccccc5n(-c5ccccc5)c4c32)cc1] | WO2007063796 |

TABLE A-continued
| MATERIAL | EXAMPLES OF MATERIAL | PUBLICATIONS |
|---|---|---|
| | 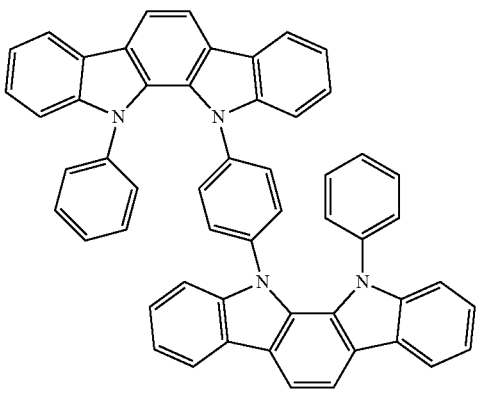 [SMILES: c1ccc(-n2c3ccccc3c3ccc4c5ccccc5n(-c5ccc(-n6c7ccccc7c7ccc8c9ccccc9n(-c9ccccc9)c8c76)cc5)c4c32)cc1] | WO2007063754 |
| 5-member ring electron deficient heterocycles (e.g., triazole, oxadiazole) | 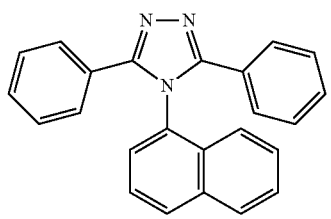 [SMILES: c1ccc(-c2nnc(-c3ccccc3)n2-c2cccc3ccccc23)cc1] | J. Appl. Phys. 90, 5048 (2001) |
| | 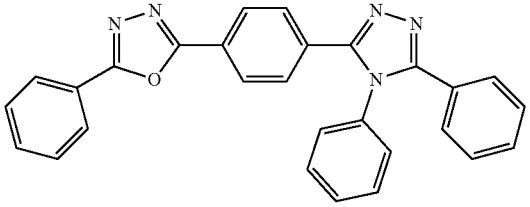 [SMILES: c1ccc(-c2nnc(-c3ccc(-c4nnc(-c5ccccc5)n4-c4ccccc4)cc3)o2)cc1] | WO2004107822 |
| Tetraphenylene complexes | 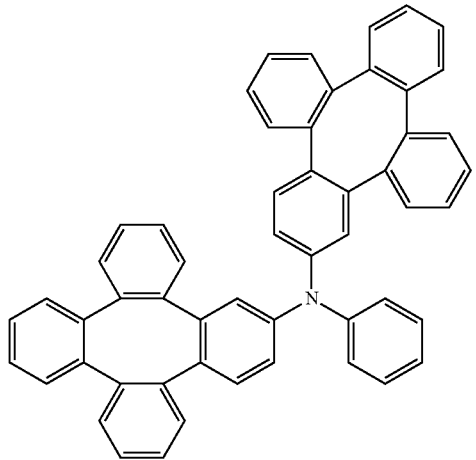 [SMILES: c1ccc(N(c2ccc3c(c2)-c2ccccc2-c2ccccc2-c2ccccc2-3)c2ccc3c(c2)-c2ccccc2-c2ccccc2-c2ccccc2-3)cc1] | US20050112407 |
| Metal phenoxypyridine compounds | 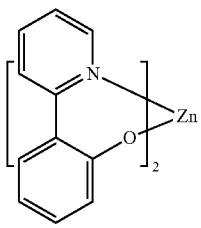 | WO2005030900 |

TABLE A-continued

| MATERIAL | EXAMPLES OF MATERIAL | PUBLICATIONS |
| --- | --- | --- |
| Metal coordination complexes (e.g., Zn, Al with N^N ligands) | | US20040137268, US20040137267 |
| Blue hosts | | |
| Arylcarbazoles | | Appl. Phys. Lett, 82, 2422 (2003) |
| | | US20070190359 |
| Dibenzothiophene/ Dibenzofuran-carbazole compounds | | WO2006114966, US20090167162 |
| | | US20090167162 |
| | | WO2009086028 |

TABLE A-continued
| MATERIAL | EXAMPLES OF MATERIAL | PUBLICATIONS |
|---|---|---|
| | 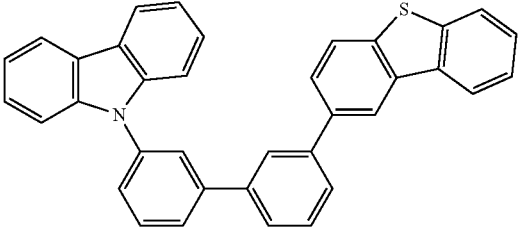 [SMILES: c1cc(-c2cccc(-n3c4ccccc4c4ccccc43)c2)cc(-c2ccc3sc4ccccc4c3c2)c1] | US20090030202, US20090017330 |
| | 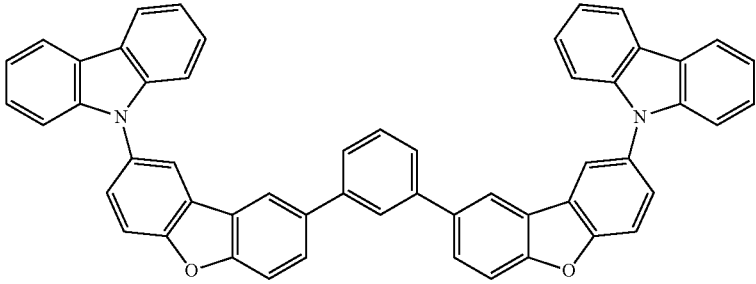 [SMILES: c1cc(-c2ccc3oc4ccc(-n5c6ccccc6c6ccccc65)cc4c3c2)cc(-c2ccc3oc4ccc(-n5c6ccccc6c6ccccc65)cc4c3c2)c1] | US20100084966 |
| Silicon aryl compounds | 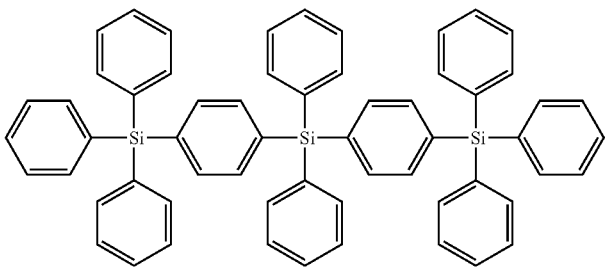 [SMILES: c1ccc([Si](c2ccccc2)(c2ccccc2)c2ccc([Si](c3ccccc3)(c3ccccc3)c3ccc([Si](c4ccccc4)(c4ccccc4)c4ccccc4)cc3)cc2)cc1] | US20050238919 |
| | 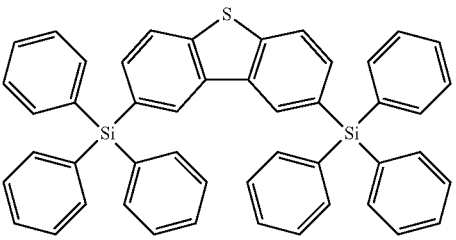 [SMILES: c1ccc([Si](c2ccccc2)(c2ccccc2)c2ccc3sc4ccc([Si](c5ccccc5)(c5ccccc5)c5ccccc5)cc4c3c2)cc1] | WO2009003898 |
| Silicon/Germanium aryl compounds | 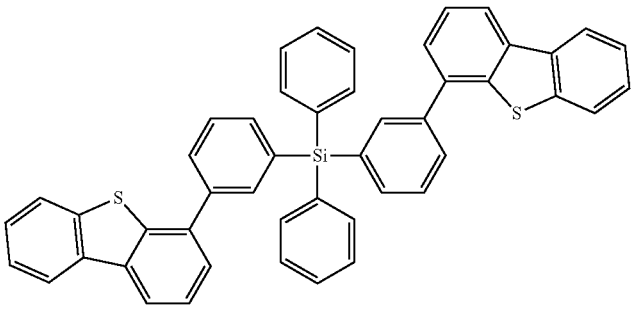 [SMILES: c1ccc([Si](c2ccccc2)(c2cccc(-c3cccc4c3sc3ccccc34)c2)c2cccc(-c3cccc4c3sc3ccccc34)c2)cc1] | EP2034538A |
| Aryl benzoyl ester | 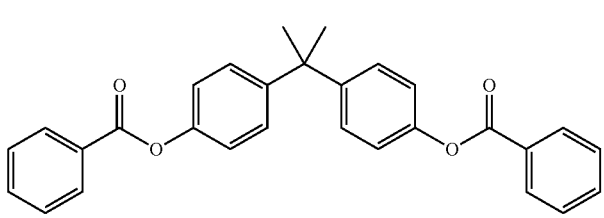 [SMILES: CC(C)(c1ccc(OC(=O)c2ccccc2)cc1)c1ccc(OC(=O)c2ccccc2)cc1] | WO2006100298 |

TABLE A-continued

| MATERIAL | EXAMPLES OF MATERIAL | PUBLICATIONS |
|---|---|---|
| Carbazole linked by non-conjugated groups | | US20040115476 |
| Aza-carbazoles | | US20060121308 |
| High triplet metal organometallic complex | | U.S. Pat. No. 7,154,114 |

Phosphorescent dopants
Red dopants

| | | |
|---|---|---|
| Heavy metal porphyrins (e.g., PtOEP) | | Nature 395, 151 (1998) |
| Iridium(III) organometallic complexes | | Appl. Phys. Lett. 78, 1622 (2001) |

TABLE A-continued

| MATERIAL | EXAMPLES OF MATERIAL | PUBLICATIONS |
|---|---|---|
| | | US20030072964 |
| | | US20030072964 |
| | | US20060202194 |
| | | US20060202194 |
| | | US20070087321 |

TABLE A-continued

| MATERIAL | EXAMPLES OF MATERIAL | PUBLICATIONS |
|---|---|---|
| | | US20080261076<br>US20100090591 |
| | | US20070087321 |
| | | Adv. Mater. 19, 739 (2007) |
| | | WO2009100991 |
| | | WO2008101842 |

TABLE A-continued

| MATERIAL | EXAMPLES OF MATERIAL | PUBLICATIONS |
| --- | --- | --- |
| | [Ir complex with pyridyl-phenyl, Cl, and two PPh₃ ligands] | U.S. Pat. No. 7,232,618 |
| Platinum(II) organometallic complexes | [Pt complex with phenyl-isoquinoline and acetylacetonate ligand] | WO2003040257 |
| | [Pt complex with N-phenyl diarylamine bis-pyridyl tridentate ligand] | US20070103060 |
| Osminum(III) complexes | [Os(PPhMe₂)₂ complex with CF₃-pyrazolyl-pyridine ligand] | Chem. Mater. 17, 3532 (2005) |
| Ruthenium(II) complexes | [Ru(PPhMe₂)₂ complex with tBu-pyrazolyl-isoquinoline ligand] | Adv. Mater. 17, 1059 (2005) |
| Rhenium (I), (II), and (III) complexes | [Re(CO)₄ complex with 8-hydroxyquinoline ligand] | US20050244673 |

TABLE A-continued
| MATERIAL | EXAMPLES OF MATERIAL | PUBLICATIONS |
|---|---|---|
| | Green dopants | |
| Iridium(III) organometallic complexes | 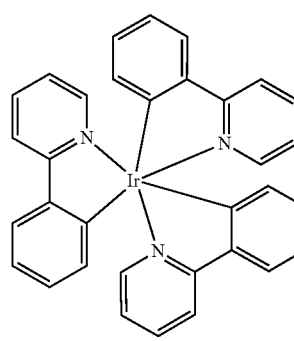 and its derivatives | Inorg. Chem. 40, 1704 (2001) |
| | 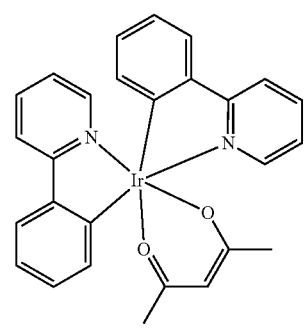 | US20020034656 |
| | 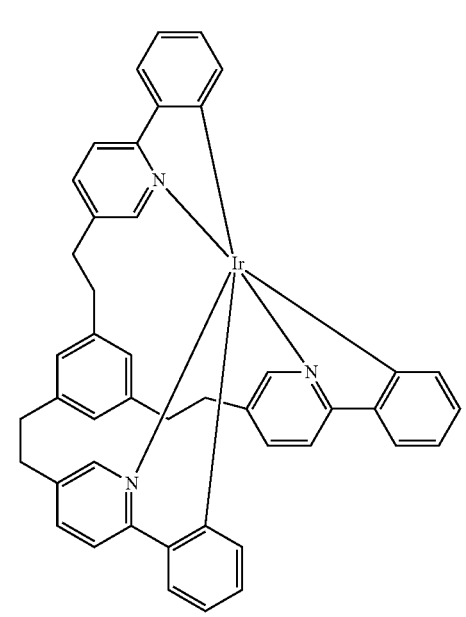 | U.S. Pat. No. 7,332,232 |

TABLE A-continued

| MATERIAL | EXAMPLES OF MATERIAL | PUBLICATIONS |
|---|---|---|
| | | US20090108737 |
| | | WO2010028151 |
| | | EP1841834B |
| | | US20060127696 |
| | | US20090039776 |

TABLE A-continued
| MATERIAL | EXAMPLES OF MATERIAL | PUBLICATIONS |
|---|---|---|
| | 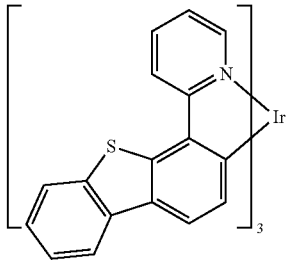 | U.S. Pat. No. 6,921,915 |
| | 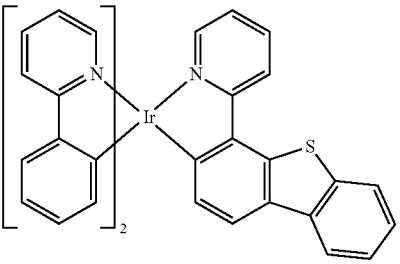 | US20100244004 |
| | 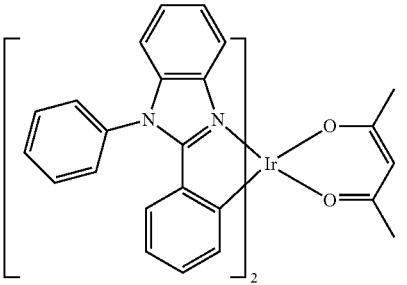 | U.S. Pat. No. 6,687,266 |
| | 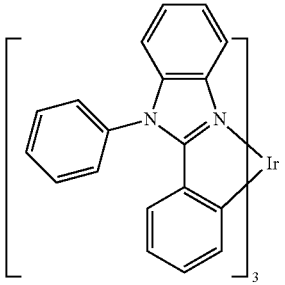 | Chem. Mater. 16, 2480 (2004) |
| | 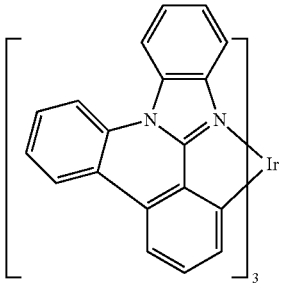 | US20070190359 |

TABLE A-continued

| MATERIAL | EXAMPLES OF MATERIAL | PUBLICATIONS |
|---|---|---|
| | | US 20060008670
JP2007123392 |
| | | WO2010086089,
WO2011044988 |
| | | Adv. Mater. 16, 2003 (2004) |
| | | Angew. Chem. Int. Ed. 2006, 45, 7800 |
| | | WO2009050290 |
| | | US20090165846 |

TABLE A-continued

| MATERIAL | EXAMPLES OF MATERIAL | PUBLICATIONS |
|---|---|---|
| | (benzotriazole-phenyl Ir with acac ligand, bis) | US20080015355 |
| | [Ir(bpy)$_3$](PF$_6$)$_3$ complex | US20010015432 |
| | (Ir complex with B-N pyridyl ligands, tris) | US20100295032 |
| Monomer for polymeric metal organometallic compounds | (Ir complex with phenylpyridine and acac-styryl ligand) | U.S. Pat. No. 7,250,226, U.S. Pat. No. 7,396,598 |
| Pt(II) organometallic complexes, including polydentate ligands | (Pt-Cl complex with N^C^N tridentate ligand) | Appl. Phys. Lett. 86, 153505 (2005) |

TABLE A-continued
| MATERIAL | EXAMPLES OF MATERIAL | PUBLICATIONS |
|---|---|---|
| | 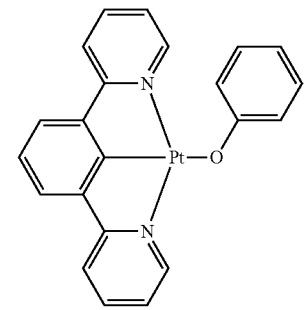 | Appl. Phys. Lett. 86, 153505 (2005) |
| | 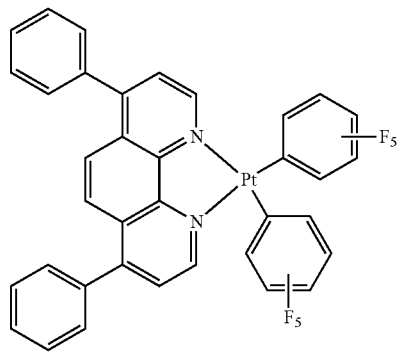 | Chem. Lett. 34, 592 (2005) |
| | 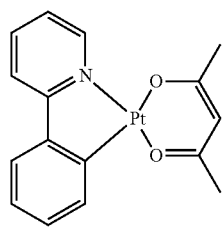 | WO2002015645 |
| | 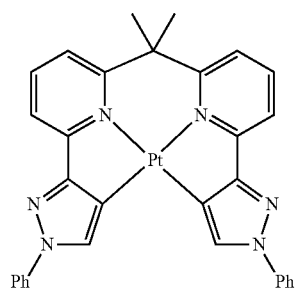 | US20060263635 |
| | 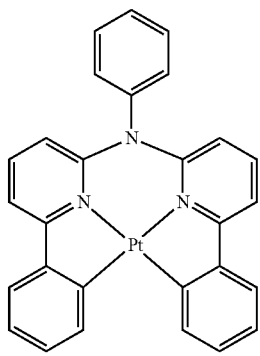 | US20060182992<br>US20070103060 |

TABLE A-continued

| MATERIAL | EXAMPLES OF MATERIAL | PUBLICATIONS |
|---|---|---|
| Cu complexes | | WO2009000673 |
| | | US20070111026 |
| Gold complexes | | Chem. Commun. 2906 (2005) |
| Rhenium(III) complexes | | Inorg. Chem. 42, 1248 (2003) |

TABLE A-continued

| MATERIAL | EXAMPLES OF MATERIAL | PUBLICATIONS |
| --- | --- | --- |
| Osmium(II) complexes | | U.S. Pat. No. 7,279,704 |
| Deuterated organometallic complexes | | US20030138657 |
| Organometallic complexes with two or more metal centers | | US20030152802 |
| | | U.S. Pat. No. 7,090,928 |

TABLE A-continued
| MATERIAL | EXAMPLES OF MATERIAL | PUBLICATIONS |
| --- | --- | --- |
| Blue dopants | | |
| Iridium(III) organometallic complexes | 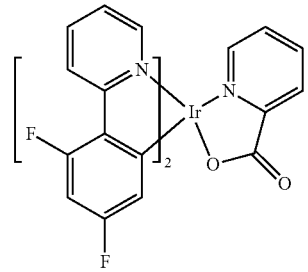 | WO2002002714 |
| | 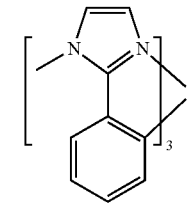 | WO2006009024 |
| | 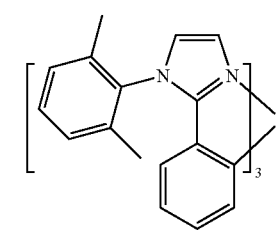 | US20060251923<br>US20110057559<br>US20110204333 |
| | 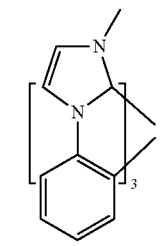 | U.S. Pat. No. 7,393,599,<br>WO2006056418,<br>US20050260441,<br>WO2005019373 |
| | 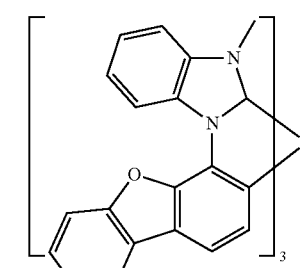 | U.S. Pat. No. 7,534,505 |

TABLE A-continued

| MATERIAL | EXAMPLES OF MATERIAL | PUBLICATIONS |
|---|---|---|
| | | WO2011051404 |
| | | U.S. Pat. No. 7,445,855 |
| | | US20070190359, US20080297033 US20100148663 |
| | | U.S. Pat. No. 7,338,722 |
| | | US20020134984 |

| MATERIAL | EXAMPLES OF MATERIAL | PUBLICATIONS |
|---|---|---|
| | 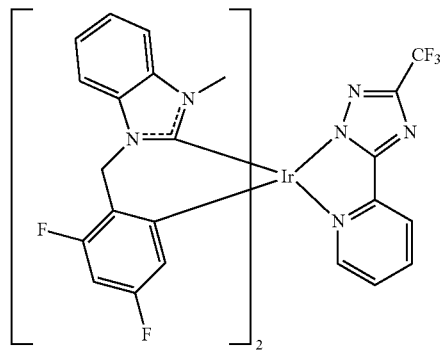 | Angew. Chem. Int. Ed. 47, 4542 (2008) |
| | 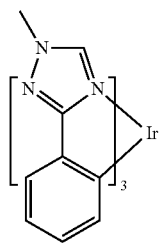 | Chem. Mater. 18, 5119 (2006) |
| | 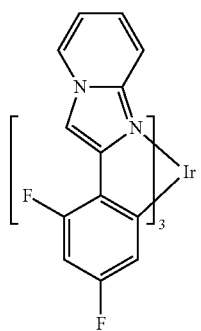 | Inorg. Chem. 46, 4308 (2007) |
| | 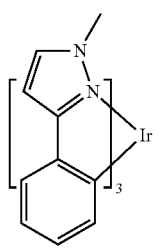 | WO2005123873 |
| | 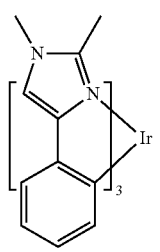 | WO2005123873 |

TABLE A-continued
| MATERIAL | EXAMPLES OF MATERIAL | PUBLICATIONS |
|---|---|---|
| | 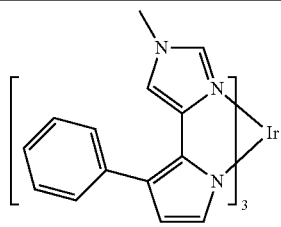 | WO2007004380 |
| | 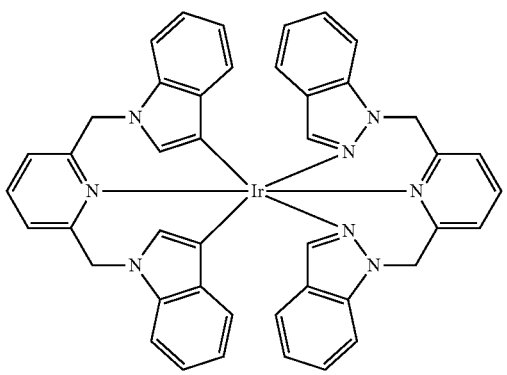 | WO2006082742 |
| Osmium(II) complexes | 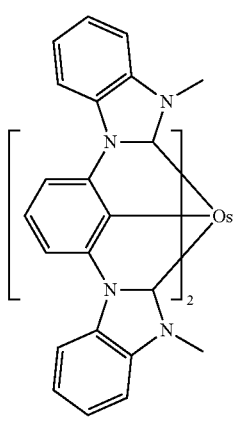 | U.S. Pat. No. 7,279,704 |
| | 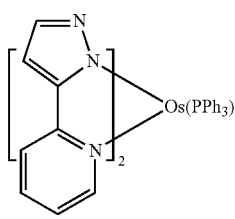 | Organometallics 23, 3745 (2004) |
| Gold complexes | 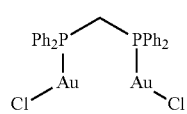 | Appl. Phys. Lett. 74,1361 (1999) |
| Platinum(II) complexes | 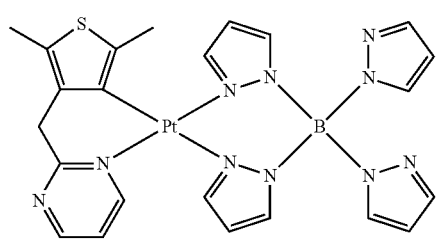 | WO2006098120, WO2006103874 |

TABLE A-continued

| MATERIAL | EXAMPLES OF MATERIAL | PUBLICATIONS |
| --- | --- | --- |
| Pt tetradentate complexes with at least one metal-carbene bond | | U.S. Pat. No. 7,655,323 |

Exciton/hole blocking layer materials

| MATERIAL | EXAMPLES OF MATERIAL | PUBLICATIONS |
| --- | --- | --- |
| Bathocuproine compounds (e.g., BCP, BPhen) | | Appl. Phys. Lett. 75, 4 (1999) |
| | | Appl. Phys. Lett. 79, 449 (2001) |
| Metal 8-hydroxyquinolates (e.g., BAlq) | | Appl. Phys. Lett. 81, 162 (2002) |
| 5-member ring electron deficient heterocycles such as triazole, oxadiazole, imidazole, benzoimidazole | | Appl. Phys. Lett. 81, 162 (2002) |

TABLE A-continued
| MATERIAL | EXAMPLES OF MATERIAL | PUBLICATIONS |
|---|---|---|
| Triphenylene compounds | 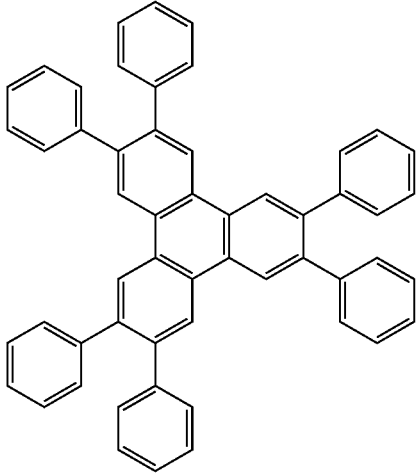 [SMILES: c1ccc(-c2cc3c4cc(-c5ccccc5)c(-c5ccccc5)cc4c4cc(-c5ccccc5)c(-c5ccccc5)cc4c3cc2-c2ccccc2)cc1] | US20050025993 |
| Fluorinated aromatic compounds | 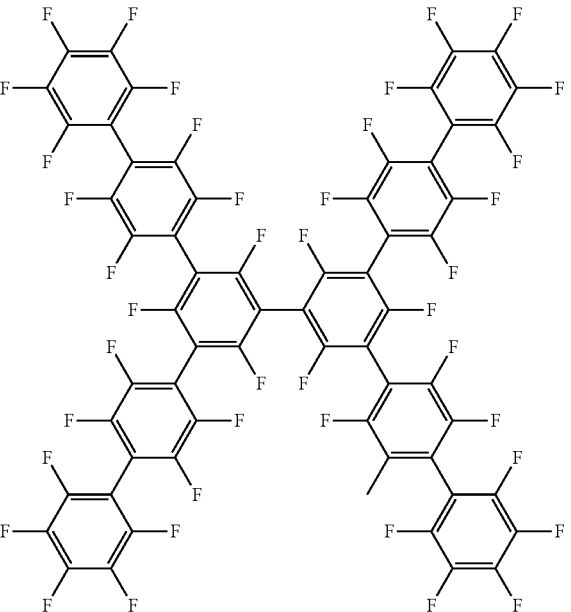 [SMILES: Cc1c(F)c(-c2c(F)c(-c3c(F)c(F)c(-c4c(F)c(F)c(F)c(F)c4F)c(F)c3F)c(F)c(-c3c(F)c(-c4c(F)c(F)c(-c5c(F)c(F)c(F)c(F)c5F)c(F)c4F)c(F)c(-c4c(F)c(F)c(-c5c(F)c(F)c(F)c(F)c5F)c(F)c4F)c3F)c2F)c(F)c(F)c1-c1c(F)c(F)c(F)c(F)c1F] | Appl. Phys. Lett. 79, 156 (2001) |
| Phenothiazine-S-oxide | 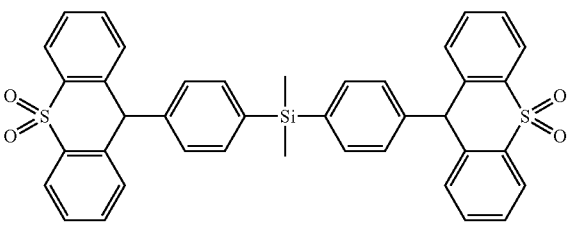 [SMILES: C[Si](C)(c1ccc(C2c3ccccc3S(=O)(=O)c3ccccc32)cc1)c1ccc(C2c3ccccc3S(=O)(=O)c3ccccc32)cc1] | WO2008132085 |
| Silylated five-membered nitrogen, oxygen, sulfur or phosphorus dibenzoheterocycles | 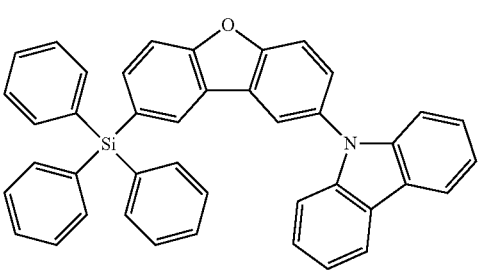 [SMILES: c1ccc([Si](c2ccccc2)(c2ccccc2)c2ccc3oc4ccc(-n5c6ccccc6c6ccccc65)cc4c3c2)cc1] | WO2010079051 |

| MATERIAL | EXAMPLES OF MATERIAL | PUBLICATIONS |
|---|---|---|
| Aza-carbazoles | 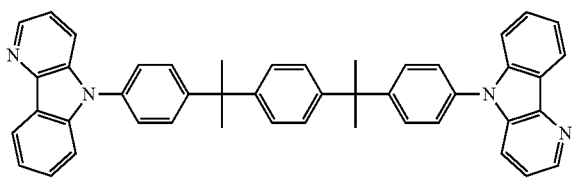 [SMILES: CC(C)(c1ccc(-n2c3ccccc3c3ncccc32)cc1)c1ccc(C(C)(C)c2ccc(-n3c4ccccc4c4ncccc43)cc2)cc1] | US20060121308 |
| Electron transporting materials | | |
| Anthracene-benzoimidazole compounds | 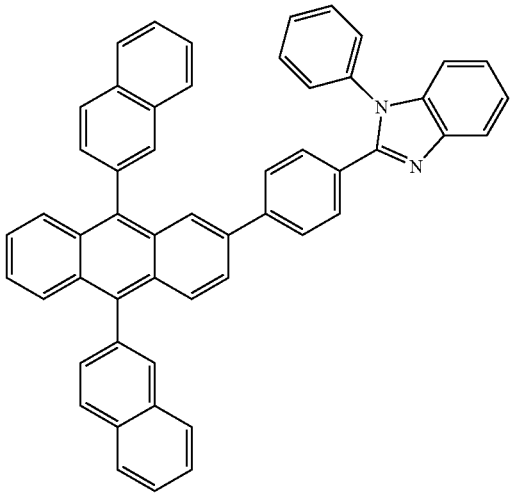 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1] | WO2003060956 |
| | 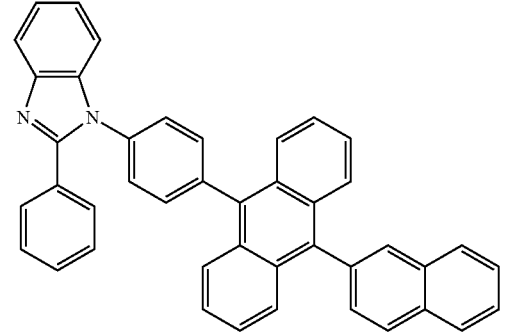 [SMILES: c1ccc(-c2nc3ccccc3n2-c2ccc(-c3c4ccccc4c(-c4ccc5ccccc5c4)c4ccccc34)cc2)cc1] | US20090179554 |
| Aza triphenylene derivatives | 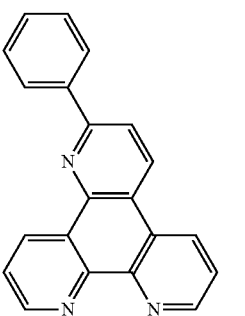 [SMILES: c1ccc(-c2ccc3c4cccnc4c4ncccc4c3n2)cc1] | US20090115316 |
| Anthracene-benzothiazole compounds | 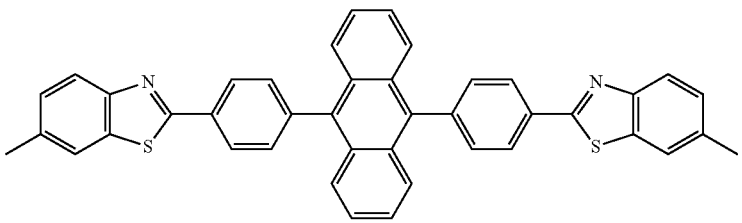 | Appl. Phys. Lett. 89, 063504 (2006) |

TABLE A-continued

| MATERIAL | EXAMPLES OF MATERIAL | PUBLICATIONS |
| --- | --- | --- |
| Metal 8-hydroxyquinolates (e.g., $Alq_3$, $Zrq_4$) | | Appl. Phys. Lett. 51, 913 (1987)<br>U.S. Pat. No. 7,230,107 |
| Metal hydroxybenoquinolates | | Chem. Lett. 5, 905 (1993) |
| Bathocuproine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole, imidazole, benzoimidazole) | | Appl. Phys. Lett. 74, 865 (1999) |
| | | Appl. Phys. Lett. 55, 1489 (1989) |

TABLE A-continued
| MATERIAL | EXAMPLES OF MATERIAL | PUBLICATIONS |
|---|---|---|
|  | 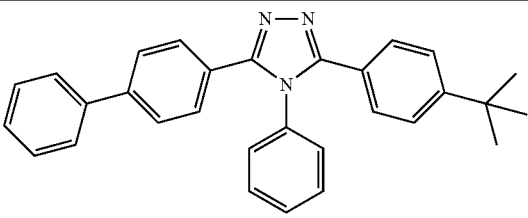 | Jpn. J. Apply. Phys. 32, L917 (1993) |
| Silole compounds | 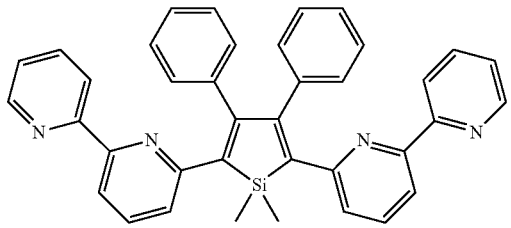 [SMILES: C[Si]1(C)C(c2cccc(-c3ccccn3)n2)=C(c2ccccc2)C(c2ccccc2)=C1c1cccc(-c2ccccn2)n1] | Org. Electron. 4, 113 (2003) |
| Arylborane compounds | 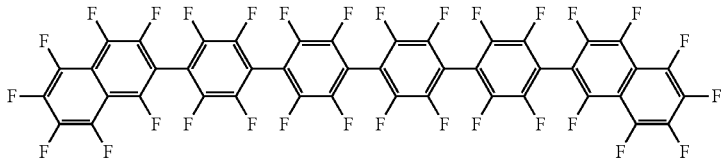 [SMILES: Fc1c(F)c(-c2c(F)c(F)c(-c3c(F)c(F)c4c(F)c(F)c(F)c(F)c4c3F)c(F)c2F)c(F)c(F)c1-c1c(F)c(F)c(-c2c(F)c(F)c(-c3c(F)c(F)c4c(F)c(F)c(F)c(F)c4c3F)c(F)c2F)c(F)c1F] | J. Am. Chem. Soc. 120, 9714 (1998) |
| Fluorinated aromatic compounds | 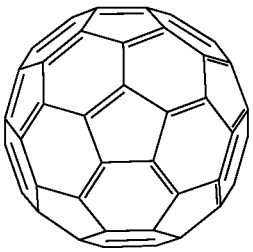 | J. Am. Chem. Soc. 122, 1832 (2000) |
| Fullerene (e.g., C60) | 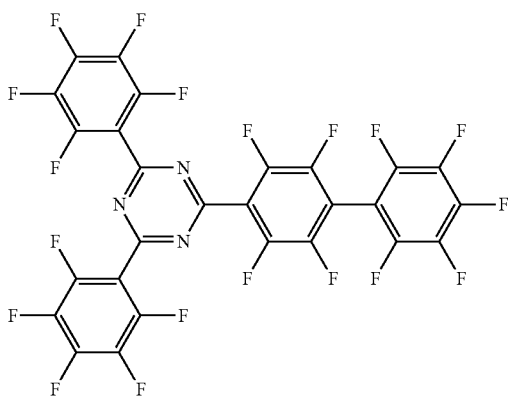 [SMILES: Fc1c(F)c(F)c(-c2nc(-c3c(F)c(F)c(F)c(F)c3F)nc(-c3c(F)c(F)c(-c4c(F)c(F)c(F)c(F)c4F)c(F)c3F)n2)c(F)c1F] | US20090101870 |
| Triazine complexes |  | US20040036077 |

TABLE A-continued

| MATERIAL | EXAMPLES OF MATERIAL | PUBLICATIONS |
|---|---|---|
| Zn (N^N) complexes | 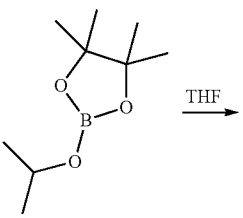 | U.S. Pat. No. 6,528,187 |

EXPERIMENTAL

SYNTHESIS EXAMPLES

Chemical abbreviations used throughout this document are as follows:

SPhos is dicyclohexyl(2',6'-dimethoxy-[1,1'-biphenyl]-2-yl)phosphine

Pd$_2$(dba)$_3$ is tri(dibenzylideneacetone) dipalladium(0),

Pd(PPh$_3$)$_4$ is tetrakis(triphenylphosphine) palladium(0),

DCM is dichloromethane,

EtOAc is ethyl acetate,

DME is dimethoxyethane, and

THF is tetrahydrofuran.

Synthesis of Compound 1

Synthesis of 2-(6-(9,9-dimethyl-9H-fluoren-2-yl)dibenzo[b,d]furan-4-yl)-4,4,5,5-tetramethyl-1,3,2-dioxaborolane

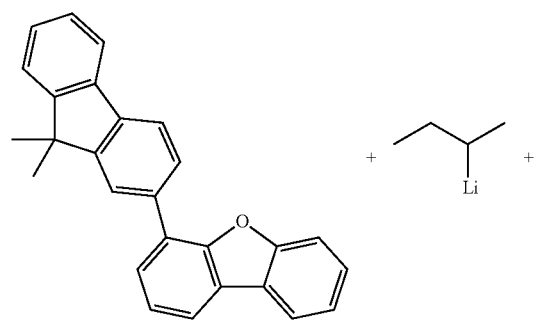

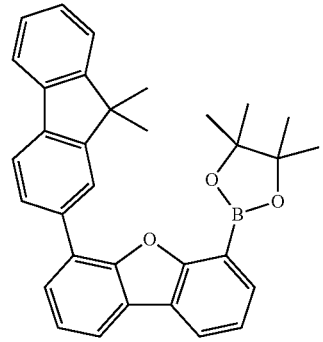

Into a solution of 4-(9,9-dimethyl-9H-fluoren-2-yl)dibenzo[b,d]furan (11.55 g, 32.0 mmol) and THF (200 ml), a solution of sec-butyllithium 1.4 M in cyclohexane (30.9 ml, 43.3 mmol) at −78° C. was slowly added. The resulting mixture was stirred at −78° C. for 2 hours before adding 2-isopropoxy-4,4,5,5-tetramethyl-1,3,2-dioxaborolane (9.81 ml, 48.1 mmol) by syringe. The reaction solution was allowed to gradually warm to room temperature and stirred for 14 h. The reaction was quenched with methanol (MeOH) and the solvent was removed in vacuo. The residue was dissolved in DCM and washed with water and brine. The organic layer was dried over sodium sulfate, then filtered, before the solvent was evaporated. The crude product was purified by column chromatography on silica gel with a heptane/DCM/EtOAc (75/20/5 to 40/50/10, v/v/v) eluent and recrystallization from toluene yielded 2-(6-(9,9-dimethyl-9H-fluoren-2-yl)dibenzo

[b,d]furan-4-yl)-4,4,5,5-tetramethyl-1,3,2-dioxaborolane (13.1 g, 84%) as a white solid.

Synthesis of Compound 1

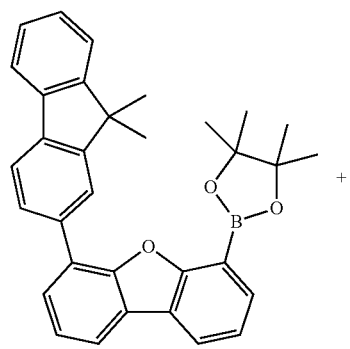

+

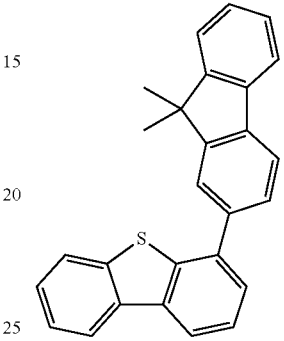

$\xrightarrow{\text{Pd(PPh}_3)_4, \text{K}_2\text{CO}_3}$
Toluene, DME/water

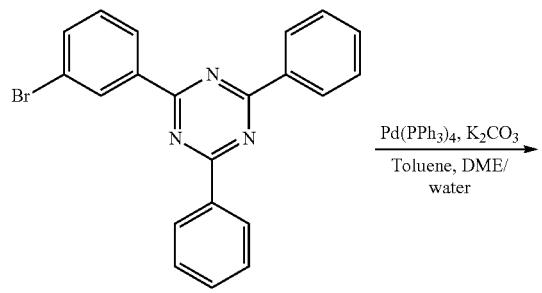

A solution of 2-(6-(9,9-dimethyl-9H-fluoren-2-yl)dibenzo[b,d]furan-4-yl)-4,4,5,5-tetramethyl-1,3,2-dioxaborolane (2.63 g, 5.41 mmol), 2-(3-bromophenyl)-4,6-diphenyl-1,3,5-triazine (2.0 g, 5.15 mmol), Pd(PPh$_3$)$_4$ (0.12 g, 0.10 mmol, and K$_2$CO$_3$ (2.136 g, 15.45 mmol) in DME (31 ml), toluene (10 ml), and water (10 ml) was refluxed under nitrogen for 14 h. After cooling to room temperature, the solid was collected by filtration, washed with ethanol, redissolved in boiling toluene, then filtered through a short plug of silica gel. Upon evaporation of the solvent, the crude product was recrystallized from toluene to yield Compound 1 (3.8 g, 74%) as a white solid.

Synthesis of Compound 2

Synthesis of 2-(6-(9,9-dimethyl-9H-fluoren-2-yl)dibenzo[b,d]thiophen-4-yl)-4,4,5,5-tetramethyl-1,3,2-dioxaborolane

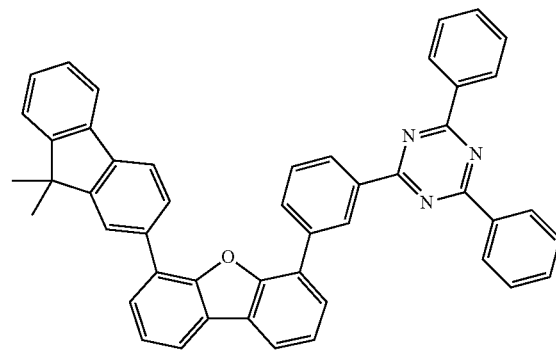

+

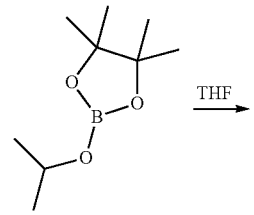

+ Li

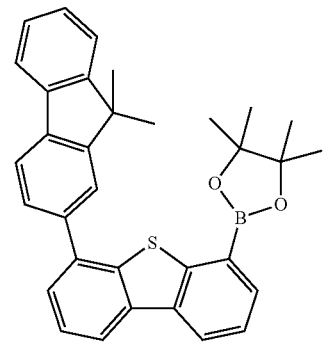

$\xrightarrow{\text{THF}}$

Into a solution of 4-(9,9-dimethyl-9H-fluoren-2-yl)dibenzo[b,d]thiophene (10.637 g, 28.3 mmol) in THF (200 ml), a solution of sec-butyllithium 1.4 M (27.2 ml, 38.1 mmol) in cyclohexane at −78° C. was added slowly. The resulting mixture was stirred at −78° C. for 2 hours before quenching with 2-isopropoxy-4,4,5,5-tetramethyl-1,3,2-dioxaborolane (8.65 ml, 42.4 mmol) added at one portion. The mixture was gradually warmed to room temperature, stirred overnight, and then quenched with methanol. The solvent was evaporated. The residue was purified by column chromatography on silica gel with a heptane/DCM (4/1 to 1/1) eluent and then precipitation in MeOH to yield 2-(6-(9,9-dimethyl- 9H-fluoren-2-yl)dibenzo[b,d]thiophen-4-yl)-4,4,5,5-tetramethyl-1,3,2-dioxaborolane (9.3 g, 65.5% yield) as a white solid.

Synthesis of Compound 2 column chromatography on silica gel with a heptane/DCM (95/5 to 9/1) eluent to yield Compound 2 (3.1 g, 69% yield) as a white solid.

Synthesis of Compound 4

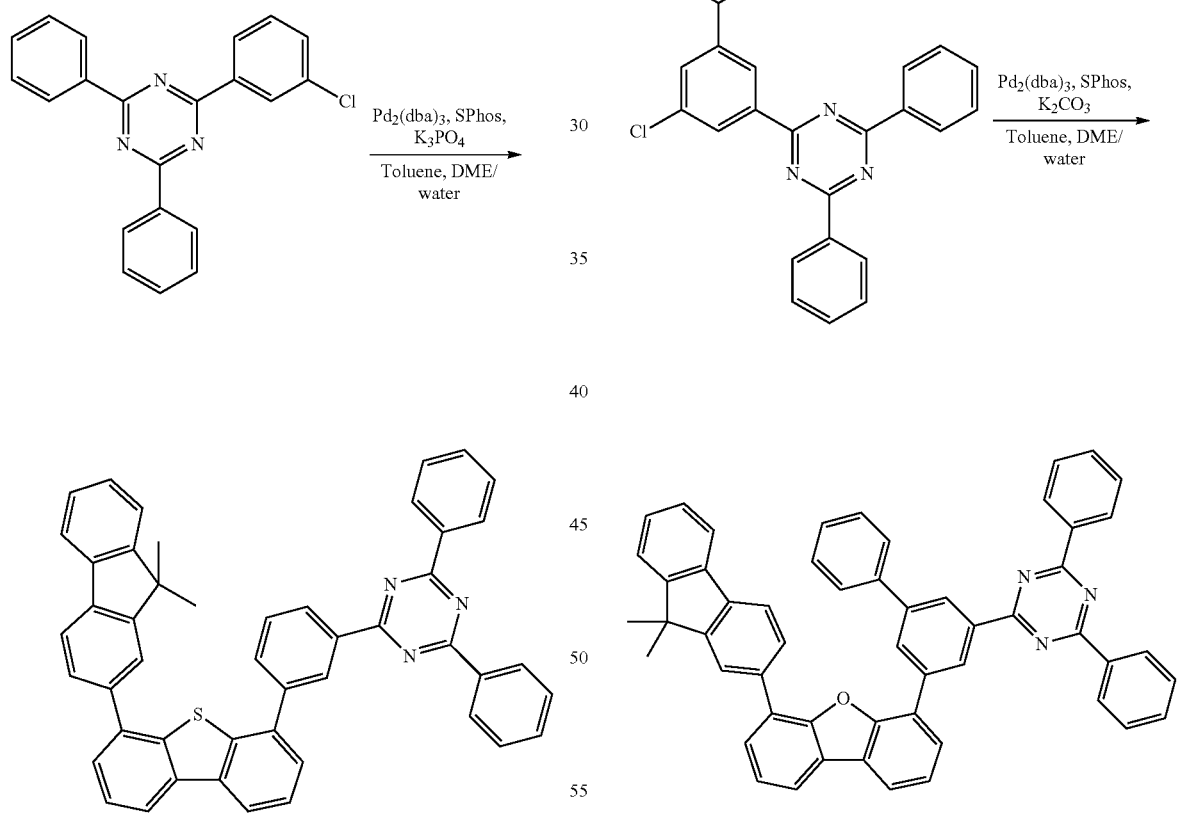

A suspension of 2-(6-(9,9-dimethyl-9H-fluoren-2-yl)dibenzo[b,d]thiophen-4-yl)-4,4,5,5-tetramethyl-1,3,2-dioxaborolane (3.3 g, 6.57 mmol), 2-(3-chlorophenyl)-4,6-diphenyl-1,3,5-triazine (2.258 g, 6.57 mmol), Pd$_2$(dba)$_3$ (0.120 g, 0.131 mmol), SPhos (0.108 g, 0.263 mmol), and K$_3$PO$_4$ (4.18 g, 19.70 mmol) in toluene (15.00 ml), DME (45.0 ml), and water (15 ml) was refluxed under nitrogen for 14 h. After cooling to room temperature, the reaction solution was quenched with water. The organic phase was isolated and the solvent was evaporated. The crude product was purified by A solution of 2-(6-(9,9-dimethyl-9H-fluoren-2-yl)dibenzo[b,d]furan-4-yl)-4,4,5,5-tetramethyl-1,3,2-dioxaborolane (3.65 g, 7.50 mmol), 2-(5-chloro-[1,1'-biphenyl]-3-yl)-4,6-diphenyl-1,3,5-triazine (3.0 g, 7.14 mmol), Pd$_2$(dba)$_3$ (0.164 g, 0.179 mmol), SPhos (0.293 g, 0.714 mmol), and K$_3$PO$_4$ (4.55 g, 21.43 mmol) in DME (43 ml), toluene (14 ml), and water (14 ml) was refluxed under nitrogen for 14 h. After cooling to room temperature, the solid was collected by filtration, washed with ethanol, redissolved in boiling toluene, and then filtered through a short plug of silica gel. After evaporating the solvent, the crude product was recrystallized from toluene to yield Compound 4 (3.5 g, 66%) as a white solid.

Synthesis of Compound 5

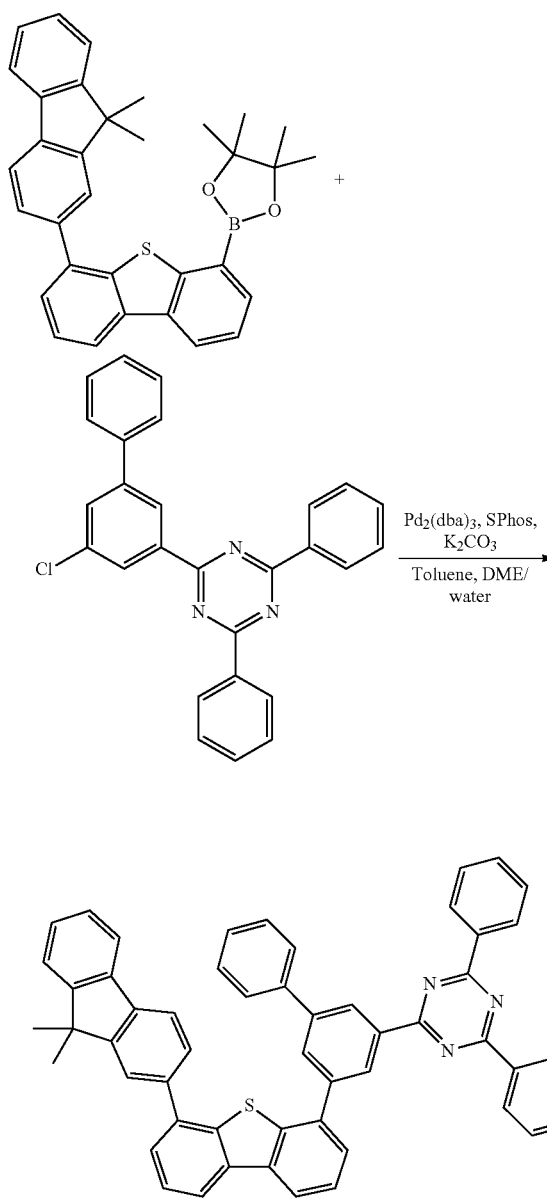

A solution of 2-(6-(9,9-dimethyl-9H-fluoren-2-yl)dibenzo[b,d]thiophen-4-yl)-4,4,5,5-tetramethyl-1,3,2-dioxaborolane (3.14 g, 6.25 mmol), 2-(5-chloro-[1,1'-biphenyl]-3-yl)-4,6-diphenyl-1,3,5-triazine (2.5 g, 5.95 mmol), $Pd_2(dba)_3$ (0.164 g, 0.179 mmol), SPhos (0.147 g, 0.357 mmol), and $K_2CO_3$ (2.469 g, 17.86 mmol) in DME (36 ml), toluene (12 ml), and water (12 ml) was refluxed under nitrogen for 14 h. After cooling to room temperature, the organic layer was isolated, washed with brine, and dried over $Na_2SO_4$. After evaporating the solvent, the residue was purified by column chromatography on silica gel with a heptane/DCM (4/1 to 2/1, v/v) eluent and recrystallization from a mixture of toluene/heptane to yield Compound 5 (2.75 g, 61%) as a white solid.

Synthesis of Compound 35

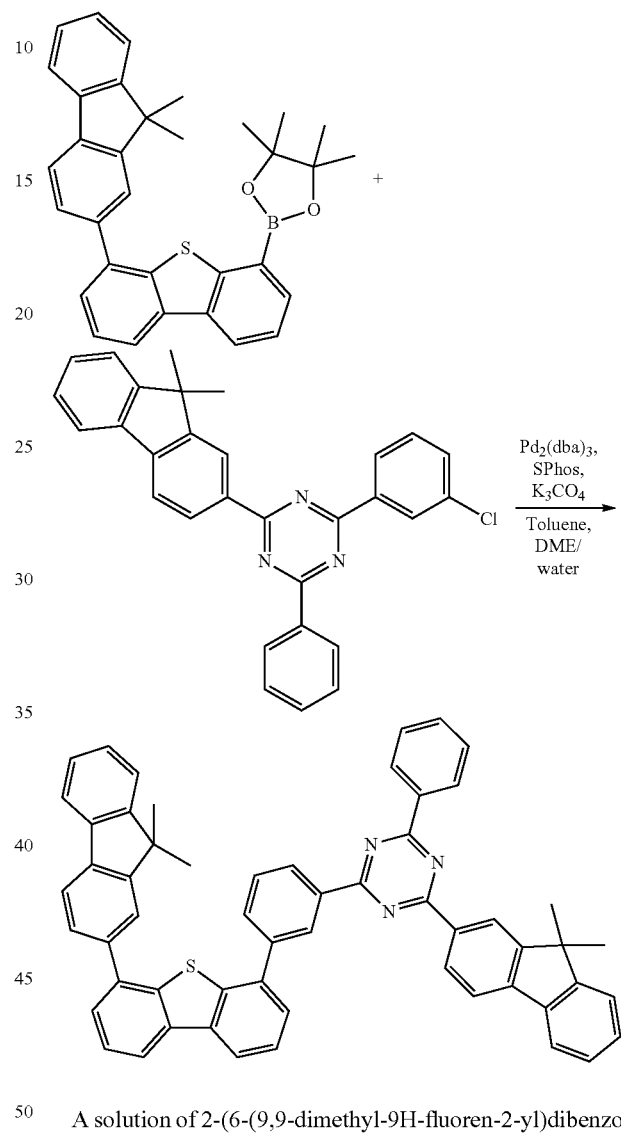

A solution of 2-(6-(9,9-dimethyl-9H-fluoren-2-yl)dibenzo[b,d]thiophen-4-yl)-4,4,5,5-tetramethyl-1,3,2-dioxaborolane (2.83 g, 5.63 mmol), 2-(3-chlorophenyl)-4-(9,9-dimethyl-9H-fluoren-2-yl)-6-phenyl-1,3,5-triazine (2.62 g, 5.69 mmol), $Pd_2(dba)_3$ (0.15 g, 0.164 mmol), SPhos (0.4 g, 0.976 mmol), and $K_3PO_4$ (3.89 g, 16.9 mmol) in toluene (100 ml), DME (100 ml), and water (25 ml) was refluxed under nitrogen for 14 h. After cooling to room temperature, the organic layer was isolated and dried over $MgSO_4$. After evaporating the solvent, the residue was purified by column chromatography on silica gel with a heptane/DCM (4/1 to 2/1, v/v) eluent and triturated with methanol to yield Compound 35 (3.65 g, 81%) as a white solid.

Device Examples

All OLED devices were fabricated by high vacuum (~$10^{-7}$ Torr) thermal evaporation. The anode electrode was 120 nm of indium tin oxide (ITO). The cathode electrode consisted of 1 nm of LiF followed by 100 nm of Al. All devices were encapsulated with a glass lid sealed with an epoxy resin in a nitrogen glove box (<1 ppm of $H_2O$ and $O_2$) immediately after fabrication, and a moisture getter was incorporated inside the package.

Device Construction.

A first set of device examples have organic stacks consisting of, sequentially, from the ITO surface, 10 nm of LG101 (from LG Chem) as the hole injection layer (HIL), 45 nm of 4,4'-bis[N-(1-naphthyl)-N-phenylaminolbiphenyl (NPD) as the hole-transport layer (HTL), and 30 nm of emissive layer (EML). On top of the EML, 50 nm of inventive compounds or comparative compounds was deposited as the hole blocking layer (HBL), followed by 40 nm of tris(8-hydroxyquinolinato)aluminum ($Alq_3$) as the electron-transport layer (ETL). The EML consists of three components: 70 wt % of HH is used as the host, with 20 wt % of inventive compound (Compound 2) or comparative compounds (CC-1, CC-2, CC-3, CC-4 and CC-5) as co-host, and 10 wt % of GD as emissive dopant. The structures of the compounds used are shown below.

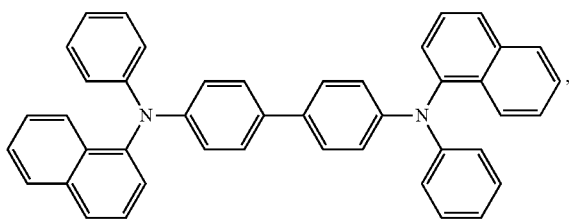

NPD

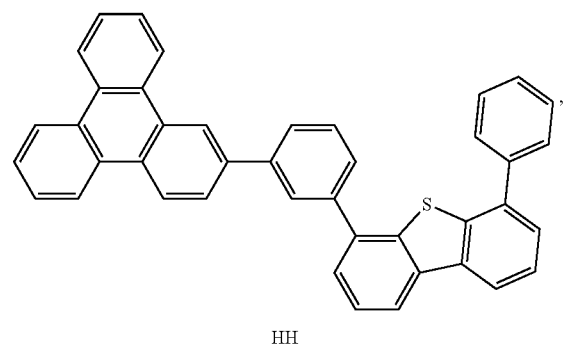

HH

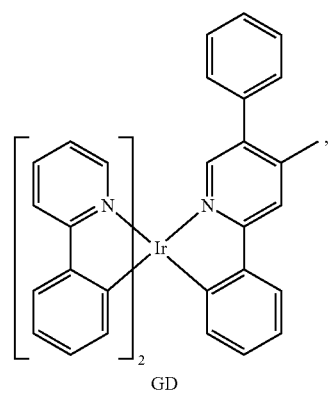

GD

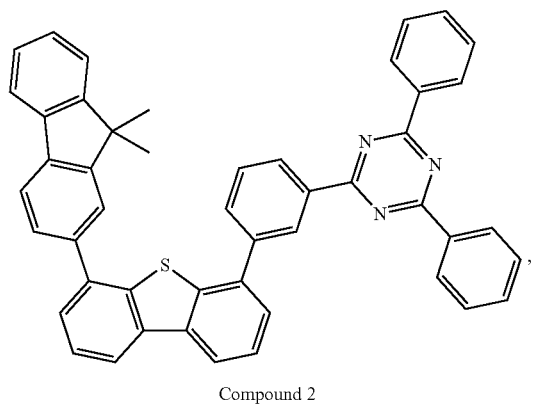

Compound 2

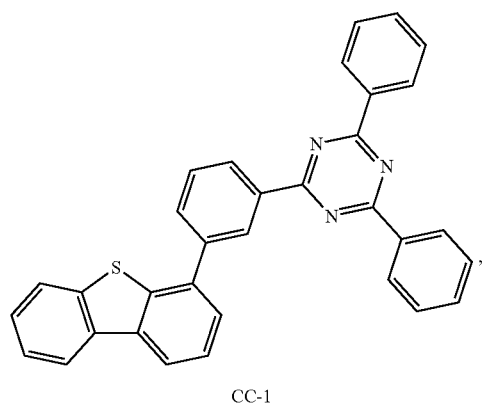

CC-1

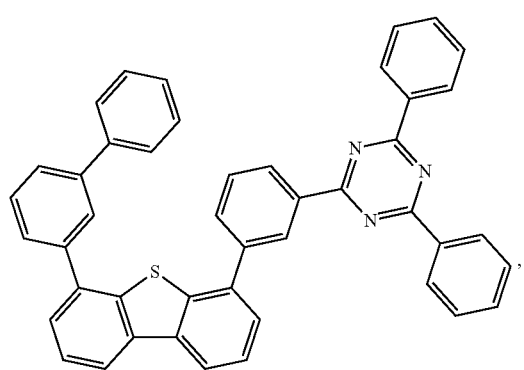

CC-2

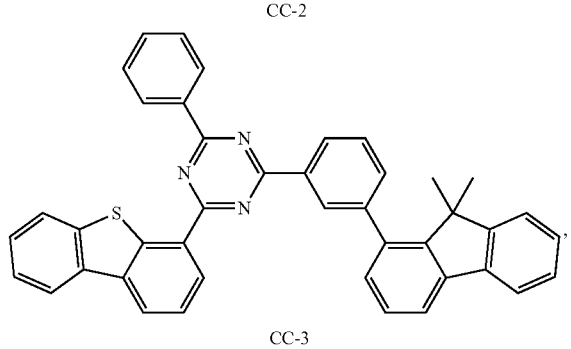

CC-3

-continued

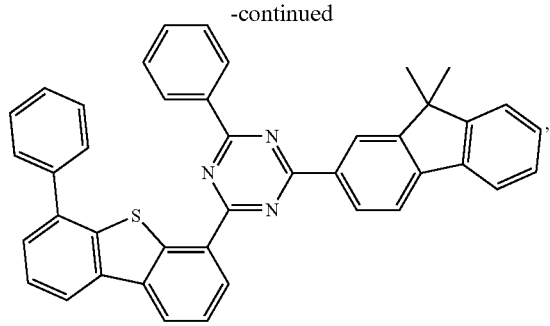

CC-4

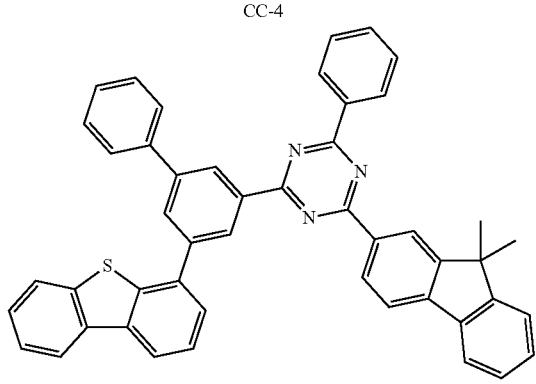

CC-5

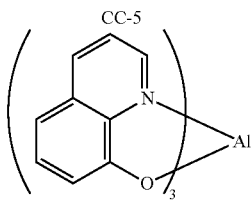

Alq3

Table 1 below is a summary of the device data. Both luminance efficiency (LE) and lifetime (LT97) were recorded at 9000 nits. LT97 is defined as the time it takes to decay to 97% of the initial luminance at a constant current density and is normalized to that of Device C-1.

TABLE 1

Select Device Components and Results

| | EML | | | LE | LT97 |
|---|---|---|---|---|---|
| Device ID | Host | Co-host | Dopant | HBL | [cd/A] | [AU] |
| Device 1 | HH | Compound 2 | GD | Compound 2 | 59.9 | 714 |
| Device C-1 | HH | CC-1 | GD | CC-1 | 58.7 | 100 |
| Device C-2 | HH | CC-2 | GD | CC-2 | 54.8 | 233 |
| Device C-3 | HH | CC-3 | GD | CC-3 | 52.9 | 345 |
| Device C-4 | HH | CC-4 | GD | CC-4 | 44.3 | 476 |
| Device C-5 | HH | CC-5 | GD | CC-5 | 52.8 | 553 |

It was found that Device 1, which uses inventive Compound 2 in the HBL and as a co-host in the EML, has higher efficiency and longer lifetime than Devices C-1, C-2, C-3° C.-4 and C-5, which use comparative compounds in the HBL and as a co-host in the EML. According to the device data, not only is the fluorene moiety an essential building block for the compounds to have high efficiency and long lifetime, but the way the fluorene moiety is connected to the compound is also crucial for superior device performance. In essence, the unique chemical structures containing fluorene, dibenzothiophene and triazine are conducive to the outstanding performance of inventive compounds.

Premixture Examples

The premixability of compounds described herein with a selected hole transporting host (h host) was evaluated by compositional analysis of films fabricated by single-source co-evaporation of the premixture of these two components.

Compound 2 and Compound H8 were physically mixed, grinded and loaded into an evaporation source. The premixed compositions were thermally co-evaporated at a rate of 2 Å/s in a vacuum chamber under a pressure less than $10^{-7}$ Torr, and deposited onto glass substrates. The substrates were replaced continuously after deposition of 500 Å of film without stopping the deposition or cooling the source. The deposition was stopped upon material depletion. The compositions of films were analyzed by high-performance liquid chromatography (HPLC) and the results are shown in Table 2.

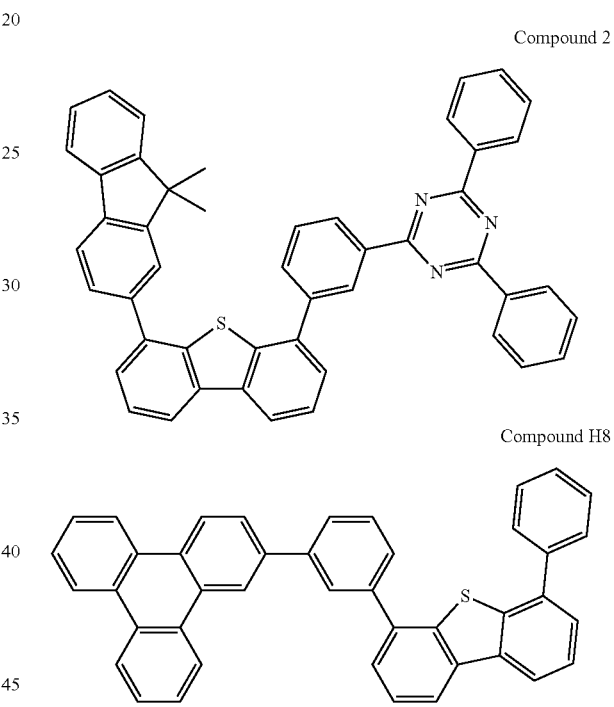

Compound 2

Compound H8

Table 2: HPLC composition (%) of sequentially deposited films from premixture comprising Compound 2 and Compound H8 with weight ratio 1:1. (HPLC Conditions C18, 100 45 min, Detection wavelength 254 nm)

| Films | Compound 2 | Compound H8 |
|---|---|---|
| Plate 1 | 40.7 | 59.3 |
| Plate 2 | 40.7 | 59.3 |
| Plate 3 | 40.4 | 59.6 |
| Plate 4 | 40.4 | 59.6 |
| Plate 5 | 40.2 | 59.8 |
| Plate 6 | 40.1 | 59.9 |
| Plate 7 | 39.5 | 60.5 |
| Plate 8 | 38.5 | 61.5 |
| Plate 9 | 40.2 | 59.8 |

The composition of the components Compound 2 and Compound H8 did not change significantly from plate 1 through plate 9. Some fluctuations in the concentrations do not reveal any trend and can be explained by the accuracy of HPLC analysis. Normally, the change of the concentration before and after depositions within 5% throughout the process is considered to be good and useful for commercial OLED application. These results demonstrate that premixture comprising Compound 2 and Compound H8 is a stable premixture for coevaporation. The coevaporation stability of this premixture is believed to be traceable to the unique chemical structures associated with these two classes of materials.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A compound having a structure of Formula I:

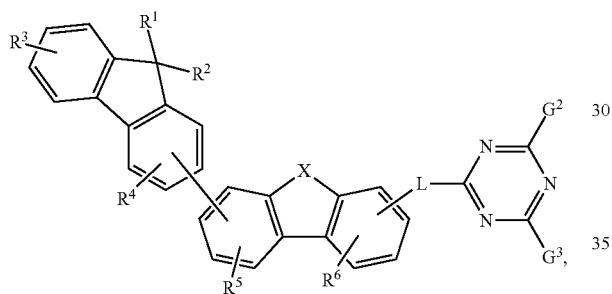

Formula I wherein X is selected from a group consisting of O, S and Se;

wherein $G^2$ and $G^3$ are each independently selected from the group consisting of benzene, biphenyl, fluorene, naphthalene, phenanthrene, triphenylene, dibenzofuran, dibenzothiophene, dibenzoselenophene, pyridine, pyrimidine, quinoline, isoquinoline, phenanthroline, azafluorene, and combinations thereof;

wherein L is selected from the group consisting of phenyl, biphenyl, terphenyl and pyridine, and combinations thereof;

wherein $G^2$, $G^3$ and L are each optionally further substituted with one or more unfused substituents selected from the group consisting of deuterium, alkyl, alkoxyl, cycloalkyl, cycloalkoxyl, halogen, nitro, nitrile, silyl, benzene, biphenyl, terphenyl, pyridine, and combinations thereof;

wherein $R^3$ represents mono, di, tri, or tetra substitution, or no substitution;

wherein $R^4$, $R^5$ and $R^6$ each independently represent mono, di, or tri substitution, or no substitution;

wherein $R^1$, $R^2$, and each $R^3$, $R^4$, $R^5$ and $R^6$ are an unfused substituent selected from the group consisting of hydrogen, deuterium, alkyl, alkoxyl, cycloalkyl, cycloalkoxyl, halogen, nitro, nitrile, silyl, benzene, biphenyl, terphenyl, pyridine, and combinations thereof; and wherein $R^1$ and $R^2$ are optionally joined to form a ring.

2. The compound of claim 1, wherein $R^1$ and $R^2$ are not joined to form a ring.

3. The compound of claim 1, wherein $R^1$ and $R^2$ are joined to form a ring.

4. The compound of claim 1, wherein $R^1$, $R^2$, and each $R^3$, $R^4$, $R^5$ and $R^6$ are an unfused substituent selected from the group consisting of hydrogen, deuterium, halogen, nitro, methyl, ethyl, propyl, butyl, pentyl, hexyl, heptyl, octyl, isopropyl, isobutyl, tert-butyl, tert-butylmethyl, 2-ethylhexyl, 2-ethyloctyl, cyclopentyl, cyclohexyl, benzene, biphenyl, terphenyl, pyridine, naphthalene, quinoline, and combinations thereof.

5. The compound of claim 1, wherein the compound is selected from the group consisting of:

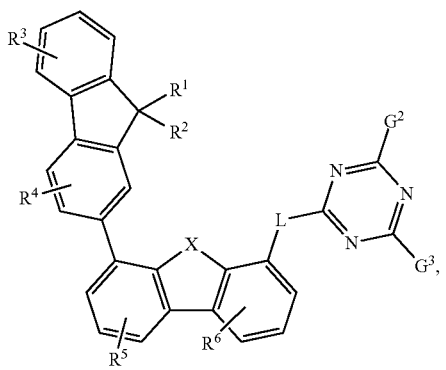

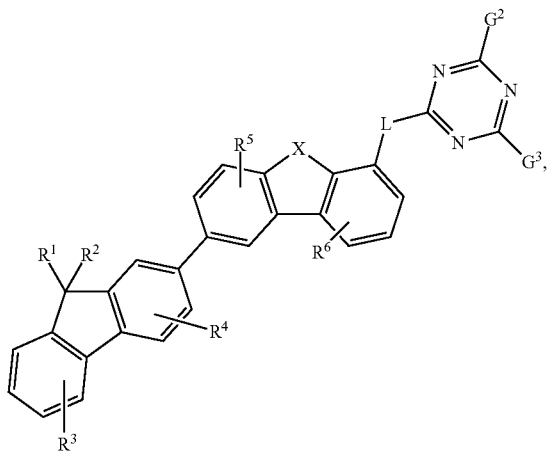

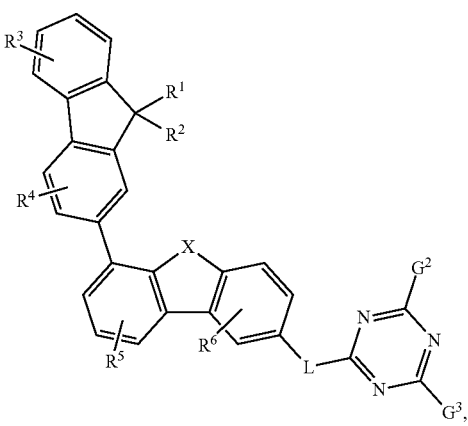

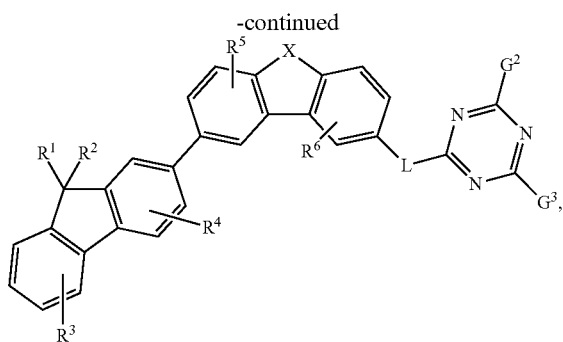

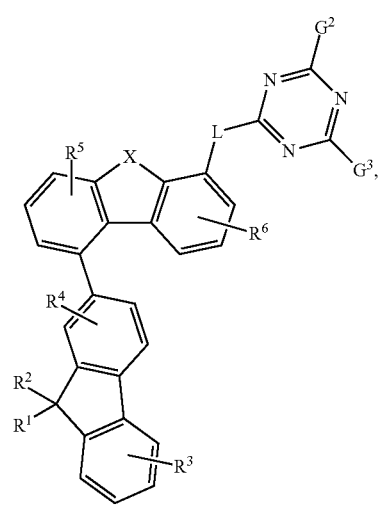

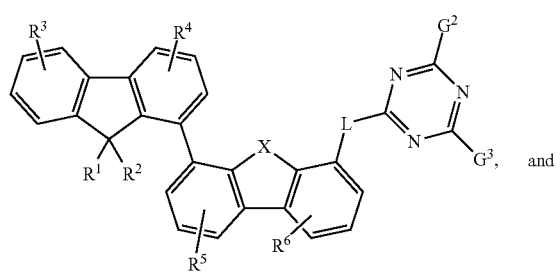

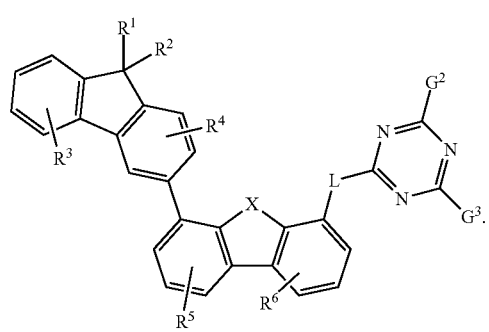

6. The compound of claim 1, wherein the compound has a structure of Formula II:

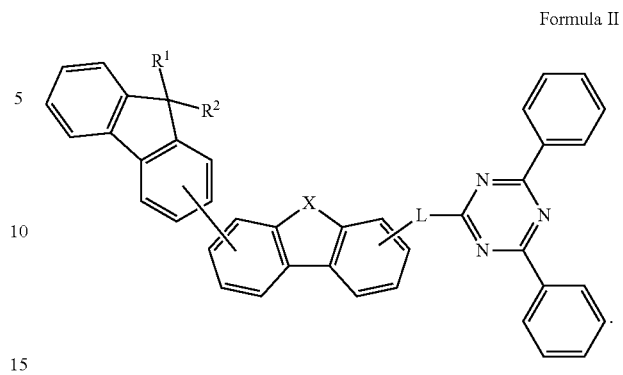

7. The compound of claim 1, wherein $G^2$ and $G^3$ are each independently a moiety selected from the group consisting of:

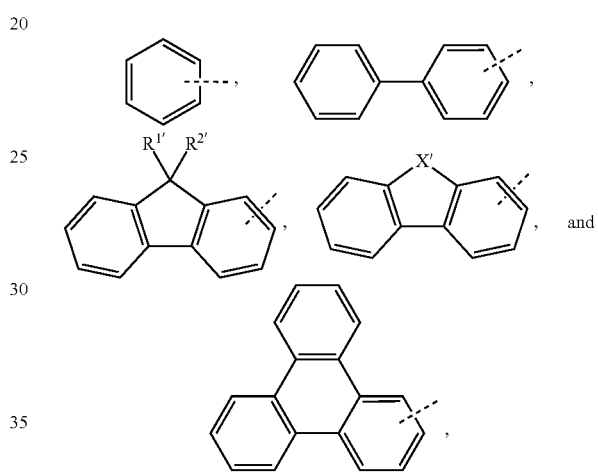

wherein $R^{1'}$ and $R^{2'}$ are independently selected from the group consisting of hydrogen, deuterium, methyl, ethyl, propyl, butyl, pentyl, hexyl, heptyl, octyl, isopropyl, isobutyl, terbutyl, terbutylmethyl, 2-ethylhexyl, 2-ethyloctyl, cyclopentyl, cyclohexyl, benzene, biphenyl, terphenyl, and combinations thereof;

wherein $R^{1'}$ and $R^{2'}$ are optionally joined to form a ring; and wherein X' is selected from a group consisting of O, S and Se.

8. The compound of claim 1, wherein L is a moiety selected from the group consisting of:

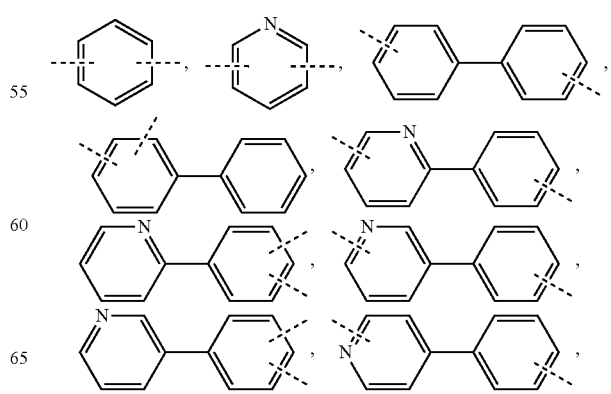

-continued
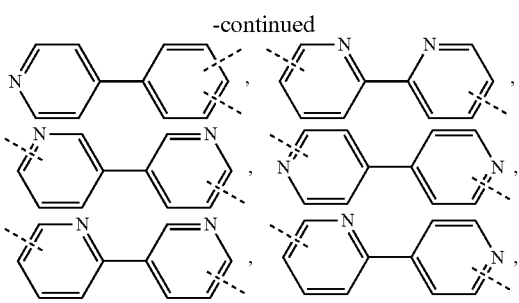
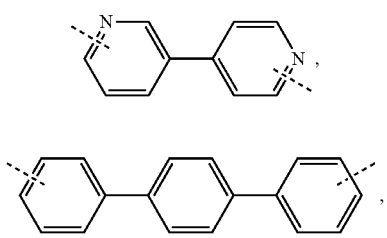
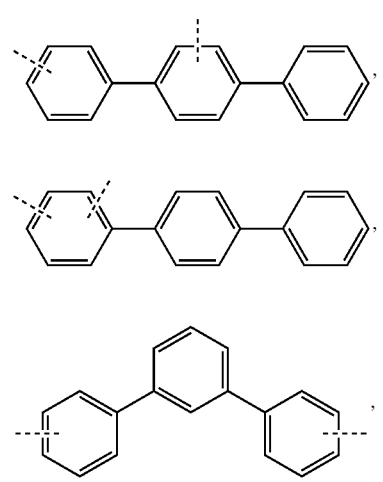
-continued
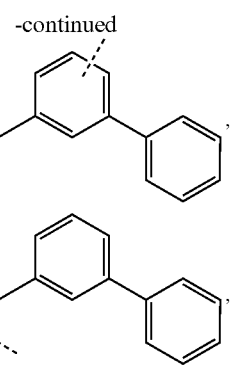
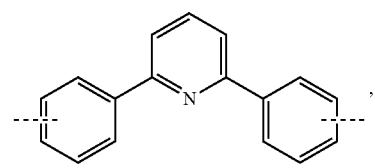
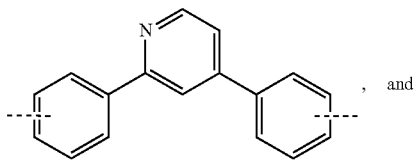
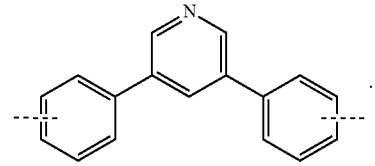, and
9. The compound of claim 1, wherein the compound is selected from the group consisting of:
Compounds 1 through 3, each represented the formula:
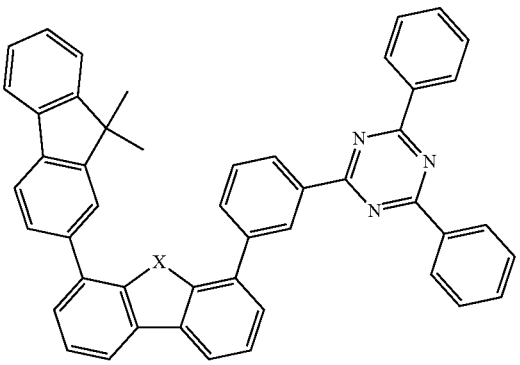
where in Compound 1: X = O,
in Compound 2, X = S, and
in Compound 3, X = Se, Compounds 4 through 6, each represented by the formula:
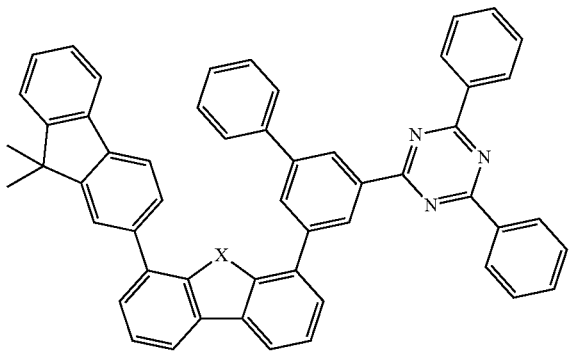
where in Compound 4: X = O,
in Compound 5, X = S, and
in Compound 6, X = Se,
Compounds 7 through 9, each represented by the formula:
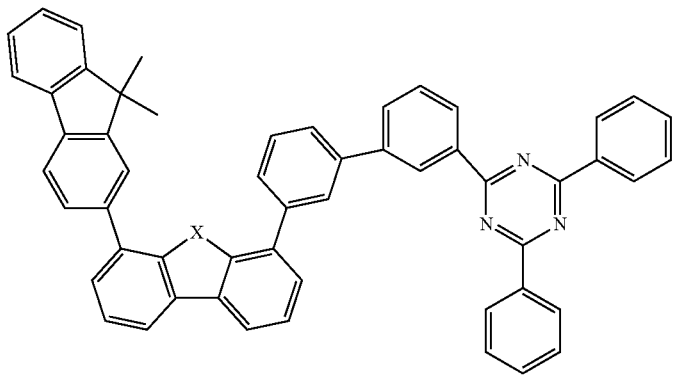
where in Compound 7: X = O,
in Compound 8, X = S, and
in Compound 9, X = Se,
Compounds 10 through 12, each represented by the formula:
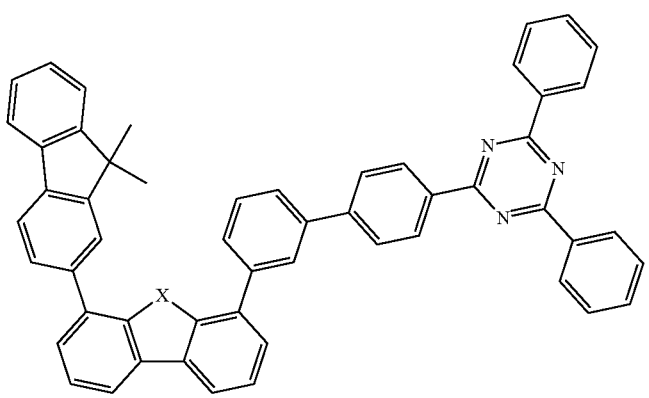
where in Compound 10: X = O,
in Compound 11, X = S, and
in Compound 12, X = Se, Compounds 13 through 15, each represented by the formula:
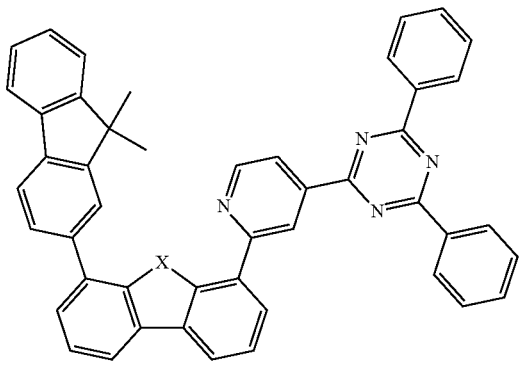
where in Compound 13: X = O,
in Compound 14, X = S, and
in Compound 15, X = Se,
Compounds 16 through 18, each represented by the formula:
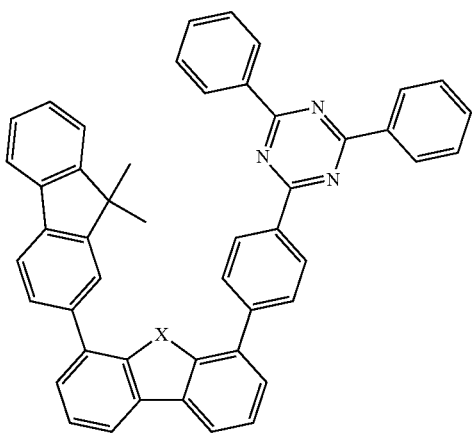
where in Compound 16: X = O,
in Compound 17, X = S, and
in Compound 18, X = Se,
Compounds 19 through 21, each represented by the formula:
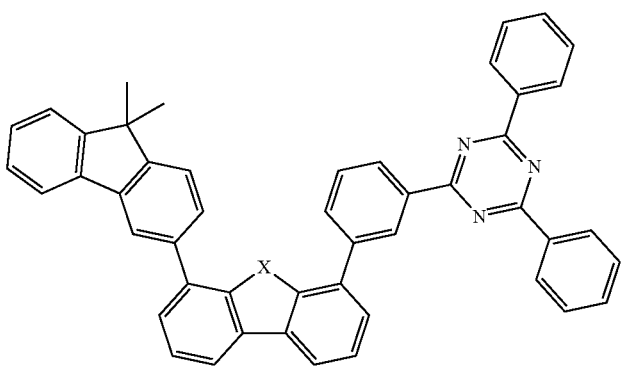
where in Compound 19: X = O,
in Compound 20, X = S, and
in Compound 21, X = Se, -continued
Compounds 22 through 24, each represented by the formula:
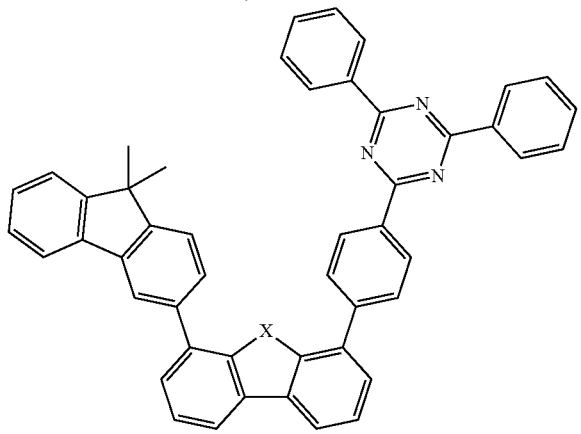
where in Compound 22: X = O,
in Compound 23, X = S, and
in Compound 24, X = Se,
Compounds 25 through 27, each represented by the formula:
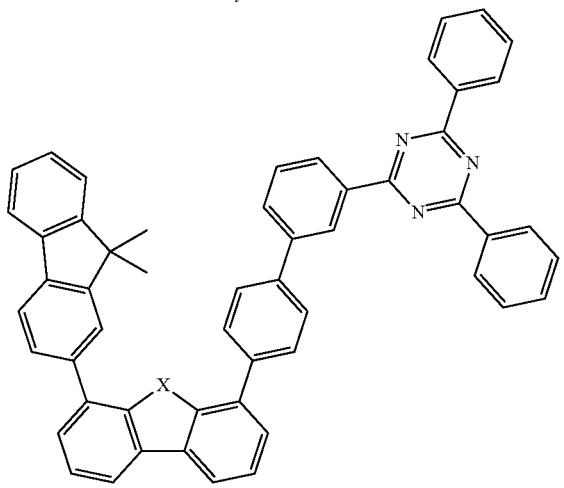
where in Compound 25: X = O,
in Compound 26, X = S, and
in Compound 27, X = Se,
Compounds 28 through 30, each represented by the formula:
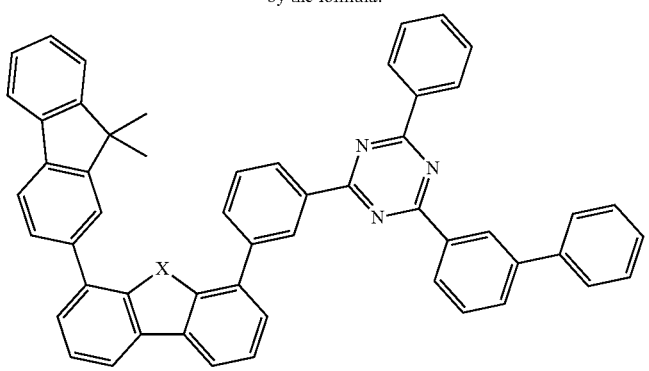
where in Compound 28: X = O,
in Compound 29, X = S, and
in Compound 30, X = Se, Compounds 31 through 33, each represented by the formula:
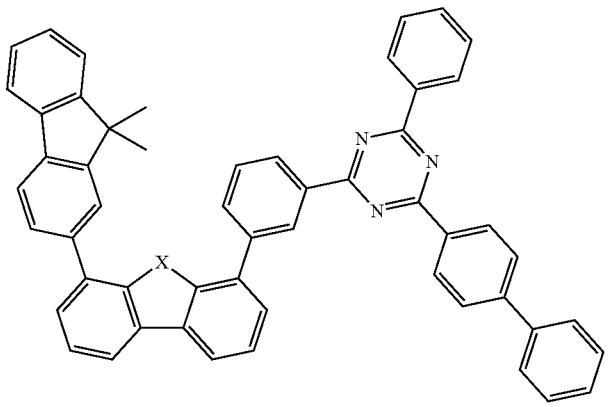
where in Compound 31: X
in Compound 32, X = S, and
in Compound 33, X = Se,
Compounds 34 through 36, each represented by the formula:
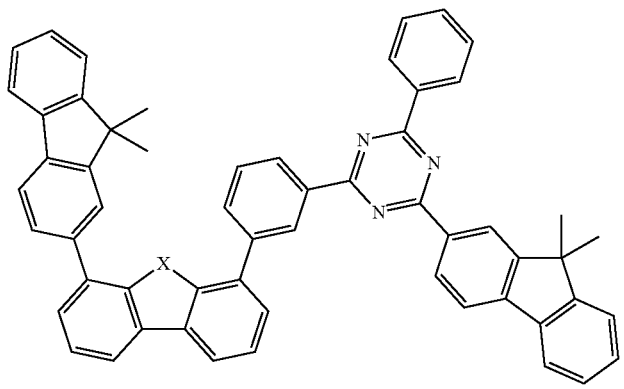
where in Compound 34: X = O,
in Compound 35, X = S, and
in Compound 36, X = Se,
Compounds 37 through 39, each represented by the formula:
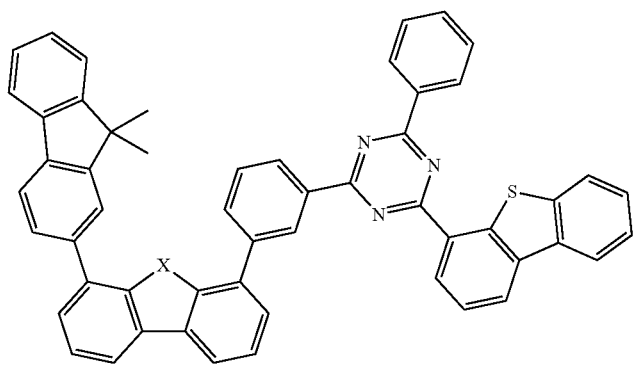
where in Compound 37: X = O,
in Compound 38, X = S, and
in Compound 39, X = Se, Compounds 40 through 42, each represented by the formula:
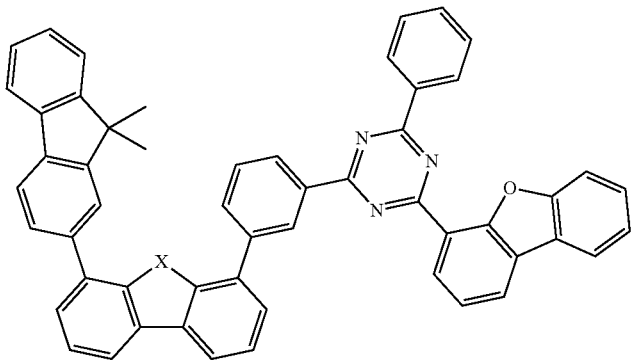
where in Compound 40: X = O,
in Compound 41, X = S, and
in Compound 42, X = Se,
Compounds 43 through 45, each represented by the formula:
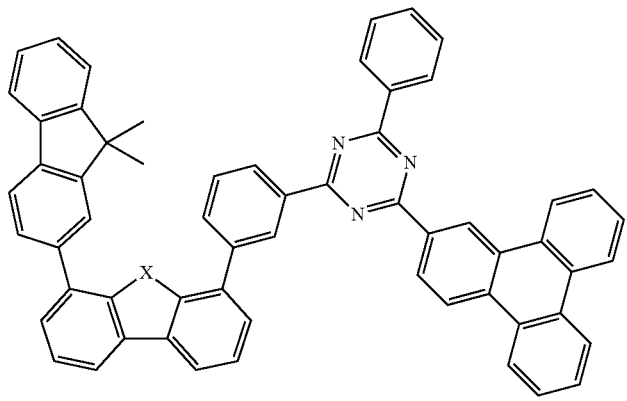
where in Compound 43: X = O,
in Compound 44, X = S, and
in Compound 45, X = Se,
Compounds 46 through 48, each represented by the formula:
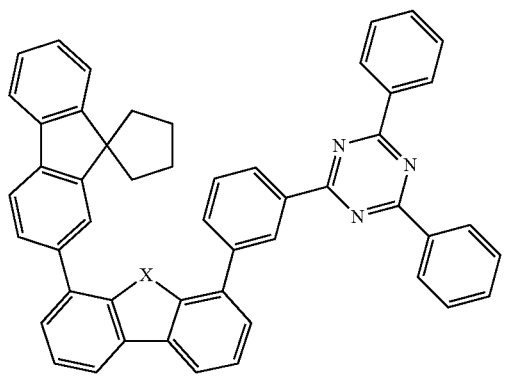
where in Compound 46: X = O,
in Compound 47, X = S, and
in Compound 48, X = Se, Compounds 49 through 51, each represented by the formula:
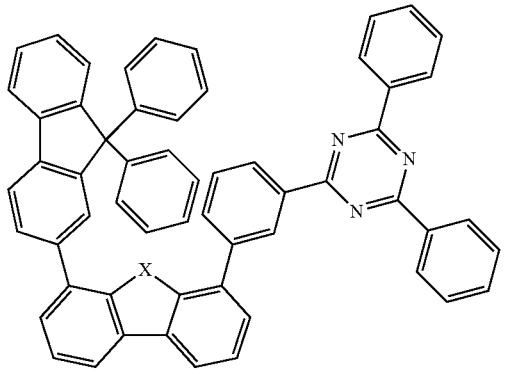
where in Compound 49: X = O,
in Compound 50, X = S, and
in Compound 51, X = Se,
Compounds 52 through 54, each represented by the formula:
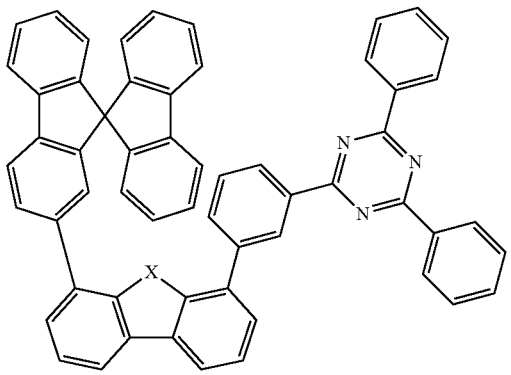
where in Compound 52: X = O,
in Compound 53, X = S, and
in Compound 54, X = Se,
Compounds 55 through 57, each represented by the formula:
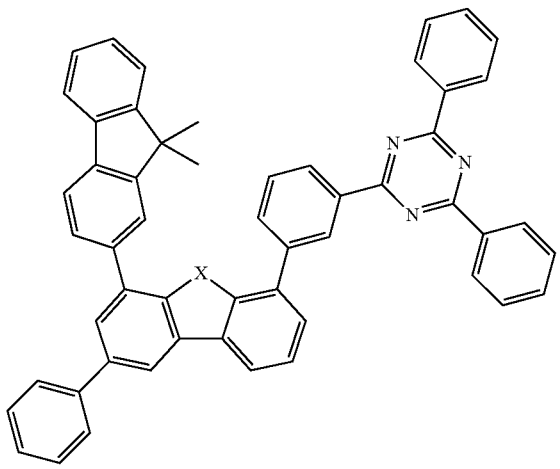
where in Compound 55: X = O,
in Compound 56, X = S, and
in Compound 57, X = Se, Compounds 58 through 60, each represented by the formula:
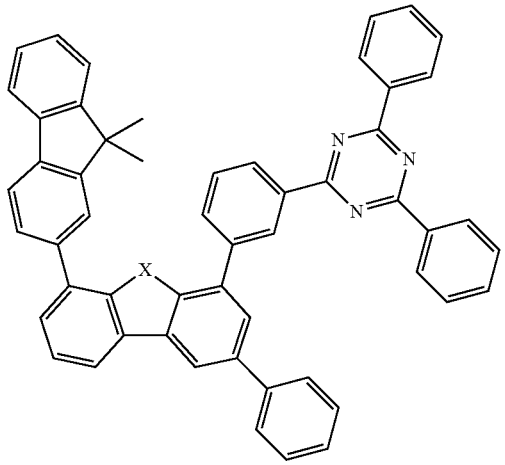
where in Compound 58: X = O,
in Compound 59, X = S, and
in Compound 60, X = Se,
Compounds 61 through 63, each represented by the formula:
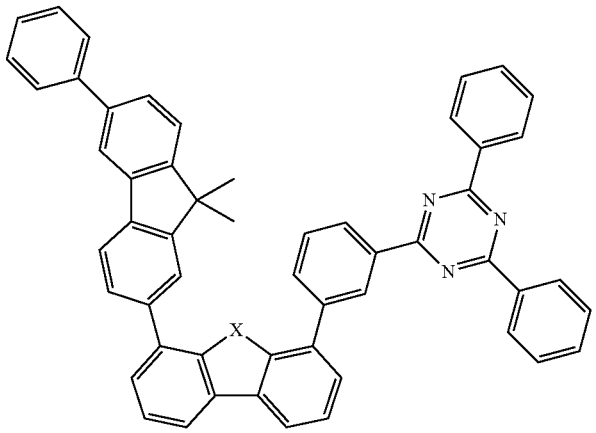
where in Compound 61: X = O,
in Compound 62, X = S, and
in Compound 63, X = Se,
Compounds 64 through 66, each represented by the formula:
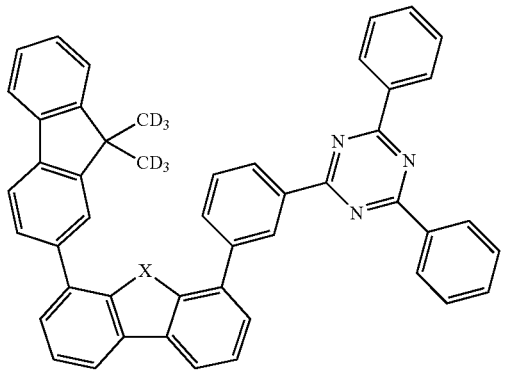
where in Compound 64: X = O,
in Compound 65, X = S, and
in Compound 66, X = Se, Compounds 67 through 69, each represented by the formula:
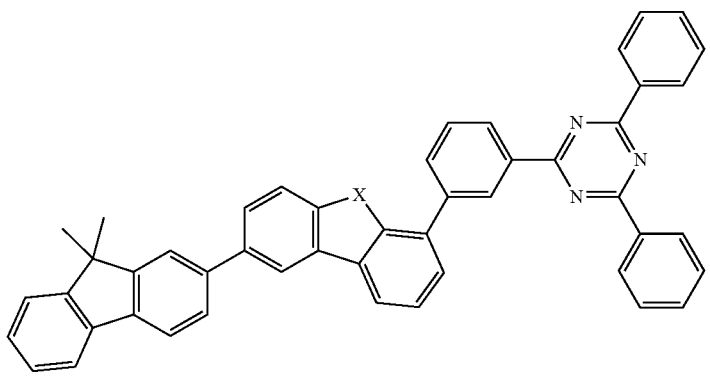
where in Compound 67: X = O,
in Compound 68, X = S, and
in Compound 69, X = Se,
Compounds 70 through 72, each represented by the formula:
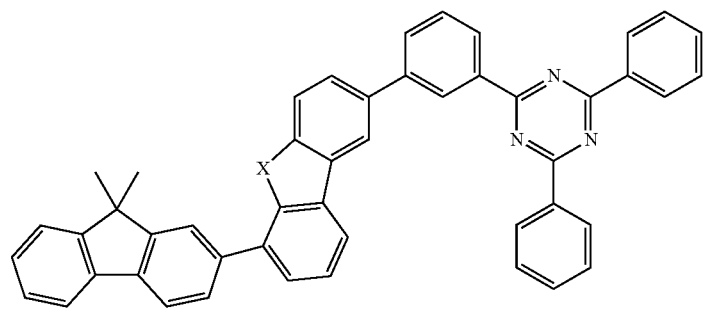
where in Compound 70: X = O,
in Compound 71, X = S, and
in Compound 72, X = Se,
Compounds 73 through 75, each represented by the formula:
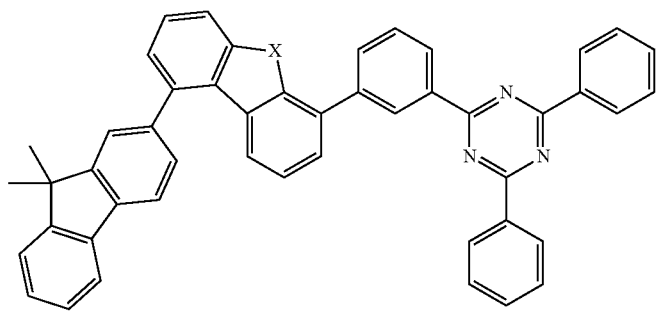
where in Compound 73: X = O
in Compound 74, X = S, and
in Compound 75, X = Se, Compounds 76 through 78, each represented by the formula:
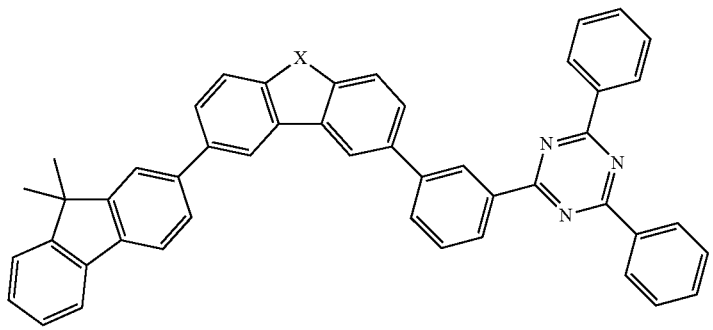
where in Compound 76: X = O,
in Compound 77, X = S, and
in Compound 78, X = Se,
Compounds 79 through 81, each represented by the formula:
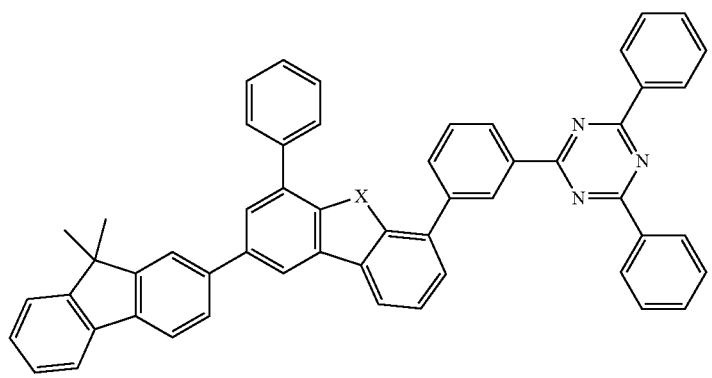
where in Compound 79: X = O,
in Compound 80, X = S, and
in Compound 81, X = Se,
Compounds 79 through 81, each represented by the formula:
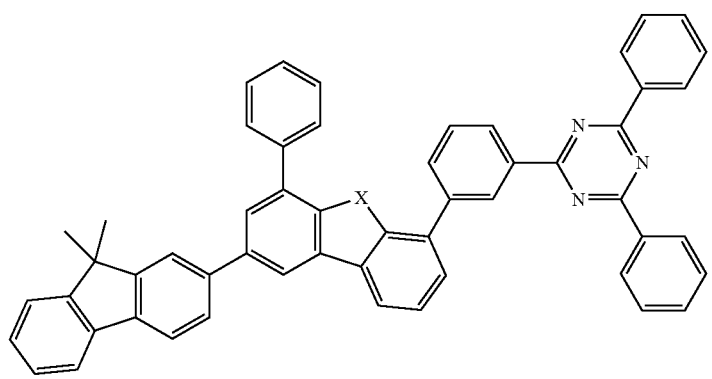
where in Compound 79: X = O,
in Compound 80, X = S, and
in Compound 81, X = Se, Compounds 82 through 84, each represented by the formula:
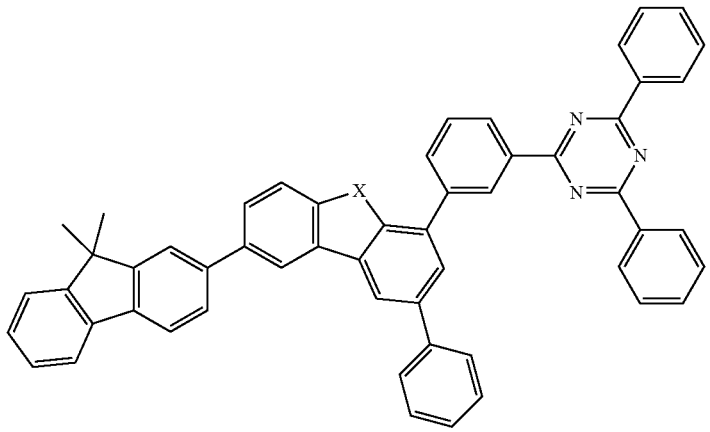
where in Compound 82: X = O,
in Compound 83, X = S, and
in Compound 84, X = Se,
Compounds 85 through 87, each represented by the formula:
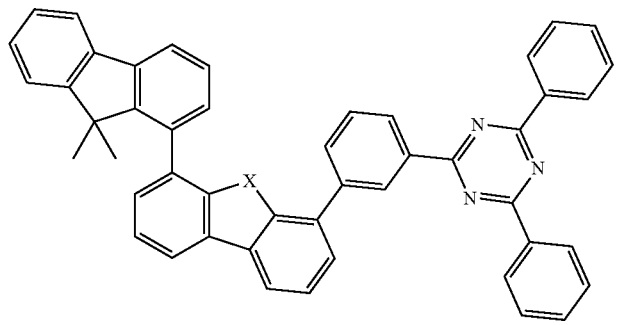
where in Compound 85: X = O,
in Compound 86, X = S, and
in Compound 87, X = Se,
Compounds 88 through 90 each represented by the formula:
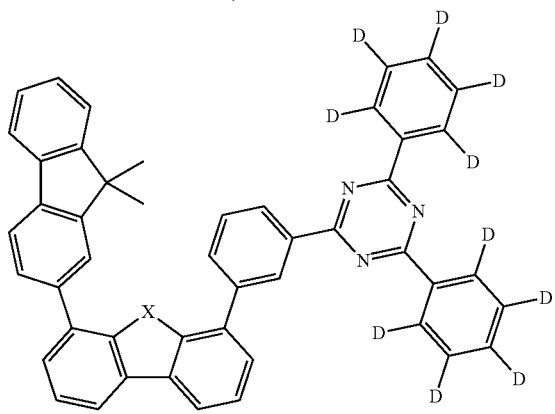
where in Compound 88: X = O,
in Compound 89, X = S, and
in Compound 90, X = Se, Compounds 91 through 93 each represented by the formula:
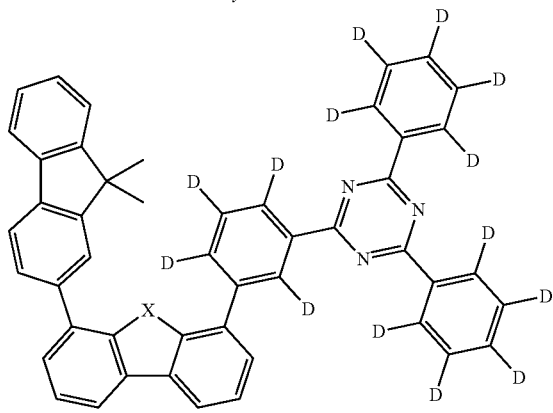
where in Compound 91: X = O,
in Compound 92, X = S, and
in Compound 93, X = Se,
Compounds 94 through 96, each represented by the formula:
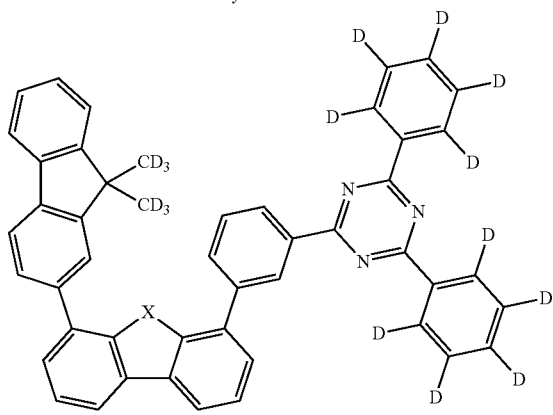
where in Compound 94: X = O,
in Compound 95, X = S, and
in Compound 96, X = Se, and
Compounds 97 through 99, each represented by the formula:
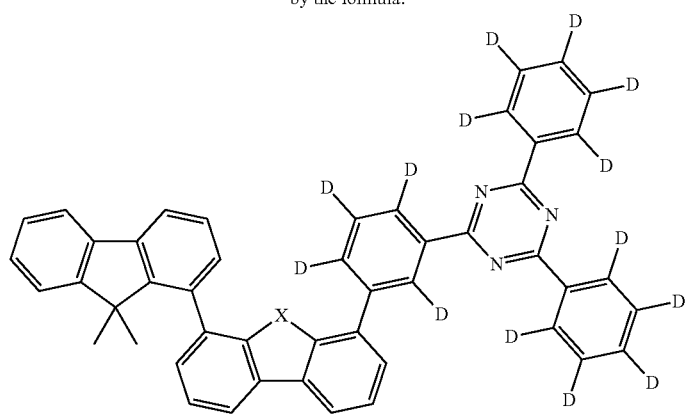
where in Compound 97: X = O,
in Compound 98, X = S, and
in Compound 99, X = Se.

10. A device comprising one or more organic light emitting devices, at least one of the one or more organic light emitting devices comprising:

an anode;

a cathode; and an organic layer, disposed between the anode and the cathode, comprising a compound having Formula I:

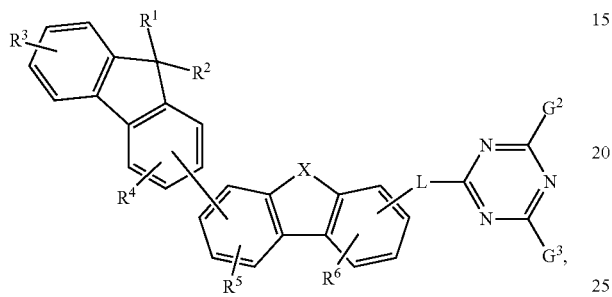

Formula I wherein X is selected from a group consisting of O, S and Se;

wherein $G^2$ and $G^3$ are each independently selected from the group consisting of benzene, biphenyl, fluorene, naphthalene, phenanthrene, triphenylene, dibenzofuran, dibenzothiophene, dibenzoselenophene, pyridine, pyrimidine, quinoline, isoquinoline, phenanthroline, azafluorene, and combinations thereof;

wherein L is selected from the group consisting of phenyl, biphenyl, terphenyl and pyridine, and combinations thereof;

wherein $G^2$, $G^3$ and L are each optionally further substituted with one or more unfused substituents selected from the group consisting of deuterium, alkyl, alkoxyl, cycloalkyl, cycloalkoxyl, halogen, nitro, nitrile, silyl, benzene, biphenyl, terphenyl, pyridine, and combinations thereof;

wherein $R^3$ represents mono, di, tri, or tetra substitution, or no substitution;

wherein $R^4$, $R^5$ and $R^6$ each independently represent mono, di, or tri substitution, or no substitution;

wherein $R^1$, $R^2$, and each $R^3$, $R^4$, $R^5$ and $R^6$ are an unfused substituent selected from the group consisting of hydrogen, deuterium, alkyl, alkoxyl, cycloalkyl, cycloalkoxyl, halogen, nitro, nitrile, silyl, benzene, biphenyl, terphenyl, pyridine, and combinations thereof; and wherein $R^1$ and $R^2$ are optionally joined to form a ring.

11. The device of claim 10, wherein the organic layer is an emissive layer and the compound of Formula I is a host.

12. The device of claim 10, wherein the organic layer further comprises an emissive dopant, wherein the emissive dopant is a transition metal complex having at least one ligand selected from the group consisting of:

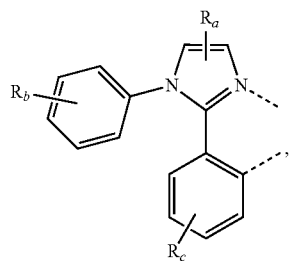

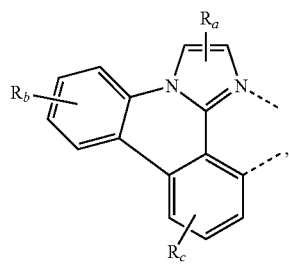

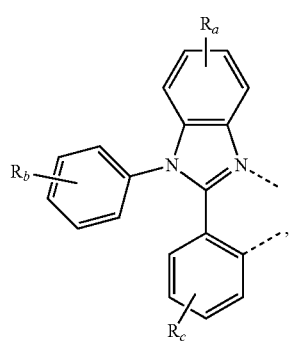

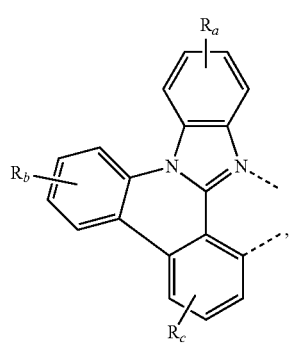

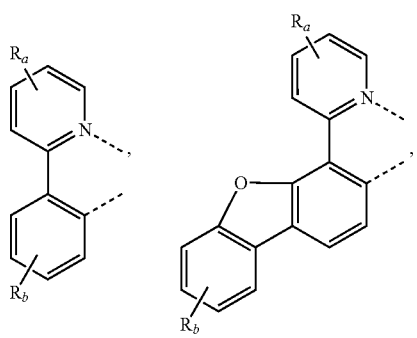

-continued

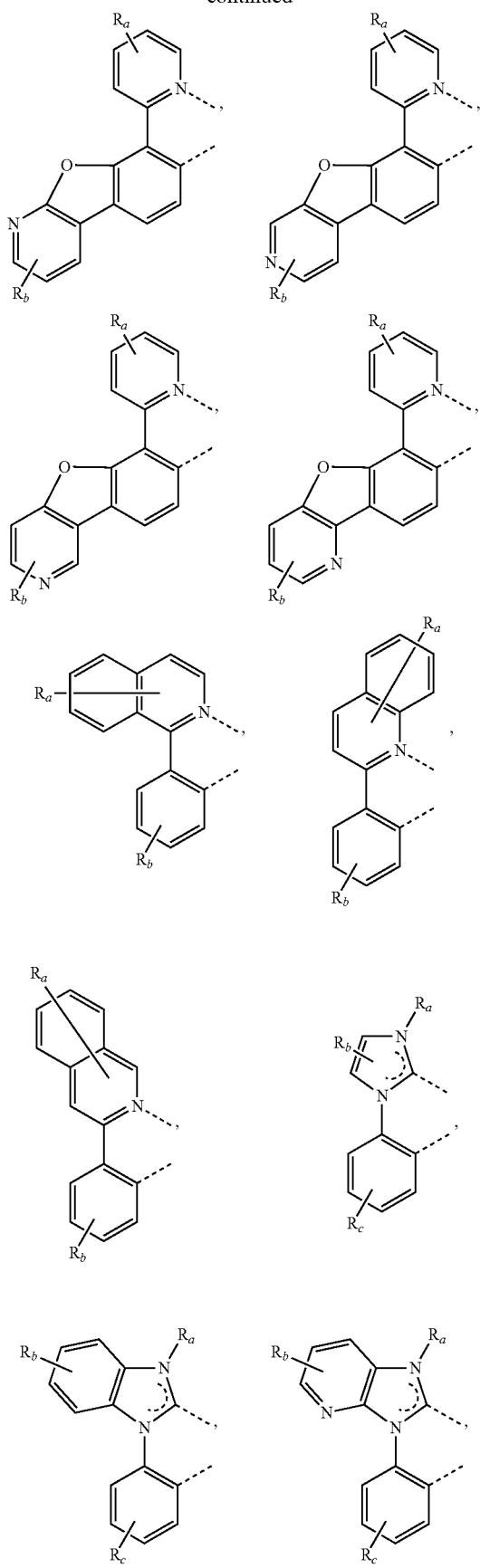
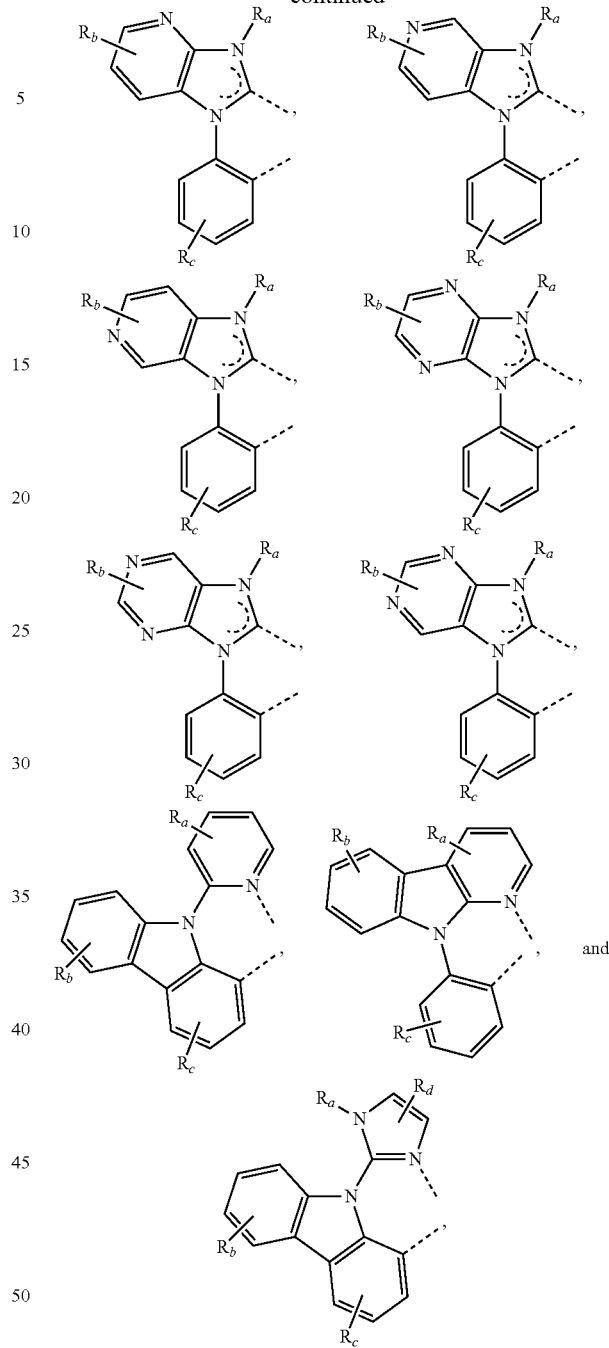

wherein $R_a$, $R_b$, $R_c$, and $R_d$ may represent mono, di, tri, or tetra substitution, or no substitution;

wherein $R_a$, $R_b$, $R_c$, and $R_d$ are independently selected from the group consisting of hydrogen, deuterium, halide, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acids, ester, nitrile, isonitrile, sulfanyl, sulfinyl, sulfonyl, phosphino, and combinations thereof; and wherein two adjacent substituents of $R_a$, $R_b$, $R_c$, and $R_d$ are optionally joined to form a fused ring or form a multidentate ligand.

13. The device of claim 10, wherein the organic layer is a blocking layer and the compound having Formula I is a blocking material in the organic layer, or wherein the organic layer is an electron transporting layer and the compound having Formula I is an electron transporting material in the organic layer.

14. The device of claim 10, wherein the device is selected from the group consisting of a consumer product, an electronic component module, an organic light-emitting device, and a lighting panel.

15. The device according to claim 10,
wherein the organic layer comprises a first composition comprising a mixture of the first compound and a second compound;
wherein the second compound has a structure of Formula III:

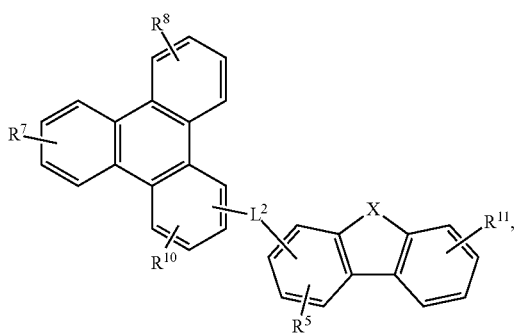

Formula III wherein X is selected from the group consisting of S, O, Se, and NR',
wherein $L^2$ is selected from a group consisting of direct bond, phenyl, biphenyl, terphenyl, fluorene, triphenylene, dibenzofuran, dibenzothiophene, dibenzoselenophene, carbazole and pyridine, and combinations thereof,
wherein $L^2$ is optionally further substituted with one or more substituents selected from a group consisting of hydrogen, deuterium, alkyl, alkoxyl, cycloalkyl, cycloalkoxyl, halogen, nitro, nitrile, silyl, aryl, heteroaryl, and combinations thereof,
wherein R', $R^7$, $R^8$, $R^9$, $R^{10}$ and $R^{11}$ are each an unfused substituent selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfinyl, sulfonyl, phosphino, and combinations thereof,
wherein $R^7$, $R^8$ and $R^{11}$ each independently represent mono, di, tri, or tetra substitution, or no substitution, and
wherein $R^9$ and $R^{10}$ each independently represent mono, di, or tri substitution, or no substitution.

16. A composition of materials comprising a first compound and a second compound,
wherein the first compound has a structure of Formula I:

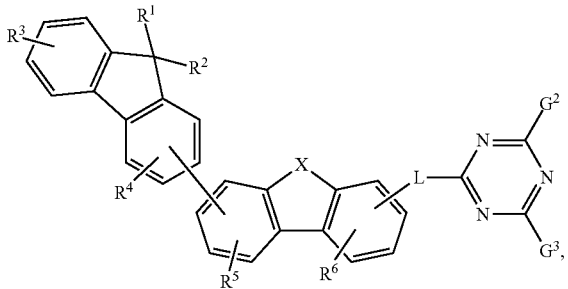

Formula I wherein X is selected from a group consisting of O, S and Se,
wherein $G^2$ and $G^3$ are each independently selected from the group consisting of benzene, biphenyl, fluorene, naphthalene, phenanthrene, triphenylene, dibenzofuran, dibenzothiophene, dibenzoselenophene, pyridine, pyrimidine, quinoline, isoquinoline, phenanthroline, azafluorene, and combinations thereof,
wherein L is selected from the group consisting of phenyl, biphenyl, terphenyl and pyridine, and combinations thereof,
wherein $G^2$, $G^3$ and L are each optionally further substituted with one or more unfused substituents selected from the group consisting of deuterium, alkyl, alkoxyl, cycloalkyl, cycloalkoxyl, halogen, nitro, nitrile, silyl, benzene, biphenyl, terphenyl, pyridine, and combinations thereof,
wherein $R^3$ represents mono, di, tri, or tetra substitution, or no substitution,
wherein $R^4$, $R^5$ and $R^6$ each independently represent mono, di, or tri substitution, or no substitution,
wherein $R^1$, $R^2$, and each $R^3$, $R^4$, $R^5$ and $R^6$ are an unfused substituent selected from the group consisting of hydrogen, deuterium, alkyl, alkoxyl, cycloalkyl, cycloalkoxyl, halogen, nitro, nitrile, silyl, benzene, biphenyl, terphenyl, pyridine, and combinations thereof, and
wherein $R^1$ and $R^2$ are optionally joined to form a ring; and
wherein the second compound has a structure of Formula III:

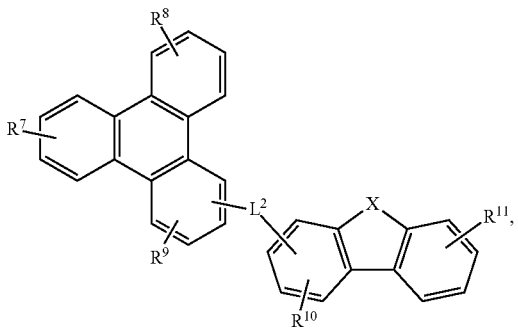

Formula III wherein X is selected from the group consisting of S, O, Se, and NR',
wherein $L^2$ is selected from a group consisting of direct bond, phenyl, biphenyl, terphenyl, fluorene, triphenylene, dibenzofuran, dibenzothiophene, dibenzoselenophene, carbazole and pyridine, and combinations thereof, wherein $L^2$ is optionally further substituted with one or more substituents selected from a group consisting of hydrogen, deuterium, alkyl, alkoxyl, cycloalkyl, cycloalkoxyl, halogen, nitro, nitrile, silyl, aryl, heteroaryl, and combinations thereof, wherein R', $R^7$, $R^8$, $R^9$, $R^{10}$ and $R^{11}$ are each an unfused substituent selected from the group consisting of hydrogen, deuterium, halogen, alkyl, cycloalkyl, heteroalkyl, arylalkyl, alkoxy, aryloxy, amino, silyl, alkenyl, cycloalkenyl, heteroalkenyl, alkynyl, aryl, heteroaryl, acyl, carbonyl, carboxylic acid, ester, nitrile, isonitrile, sulfanyl, sulfanyl, sulfonyl, phosphino, and combinations thereof, wherein $R^7$, $R^8$ and $R^{11}$ each independently represent mono, di, tri, or tetra substitution, or no substitution, and wherein $R^9$ and $R^{10}$ each independently represent mono, di, or tri substitution, or no substitution.

17. The composition of claim 16, wherein the second compound is selected from the group consisting of:

Compounds H1 through H3, each represented by the formula:

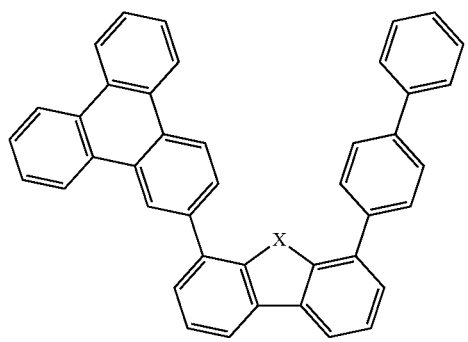

where in Compound H1: X = O,
in Compound H2, X = S, and
in Compound H3, X = Se,

Compounds H4 through H6, each represented by the formula:

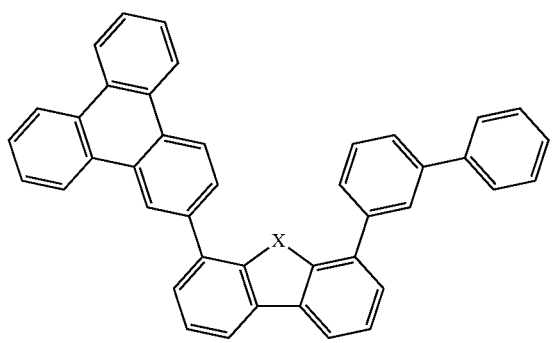

where in Compound H4: X = O,
in Compound H5, X = S, and
in Compound H6, X = Se,

Compounds H7 through H9, each represented by the formula:

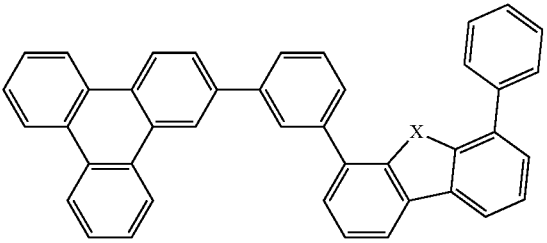

where in Compound H7: X = O,
in Compound H8, X = S, and
in Compound H9, X = Se,

Compounds H10 through H12, each represented by the formula:

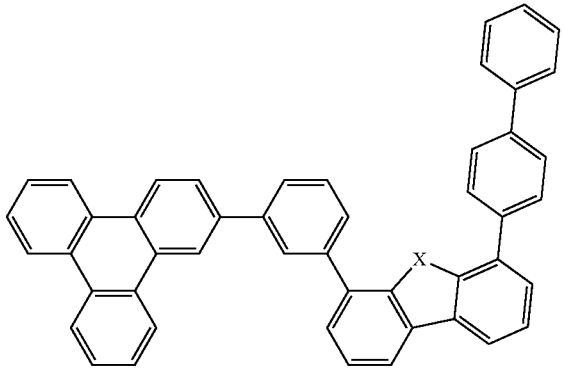

where in Compound H10: X = O,
in Compound H11, X = S, and
in Compound H12, X = Se, Compounds H13 through H15, each represented by the formula:

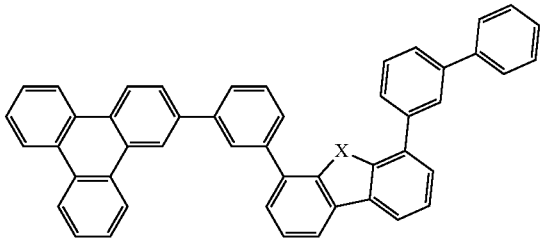

where in Compound H13: X = O,
in Compound H14, X = S, and
in Compound H15, X = Se, Compounds H16 through H18, each represented by the formula:

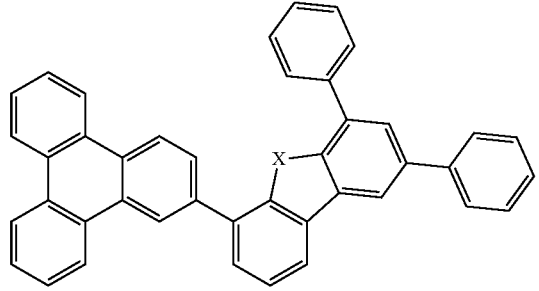

where in Compound H16: X = O,
in Compound H17, X = S, and
in Compound H18, X = Se, Compounds H19 through H21, each represented by the formula:

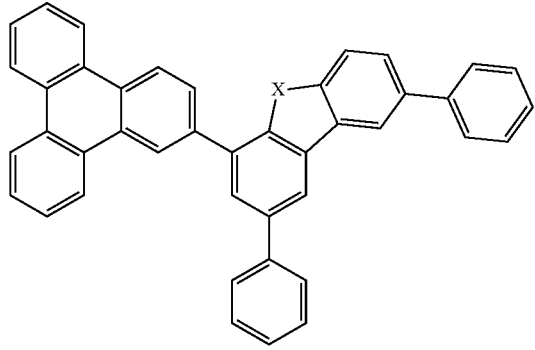

where in Compound H19: X = O,
in Compound H20, X = S, and
in Compound H21, X = Se, Compounds H22 through H24, each represented by the formula:

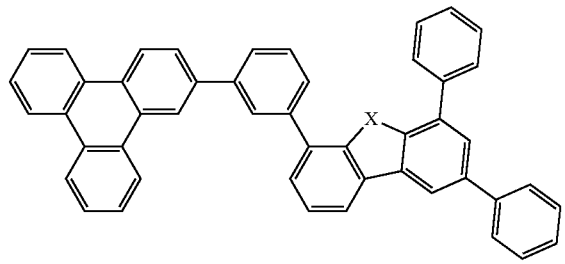

where in Compound H22: X = O,
in Compound H23, X = S, and
in Compound H24, X = Se, Compounds H25 through H27, each represented by the formula:

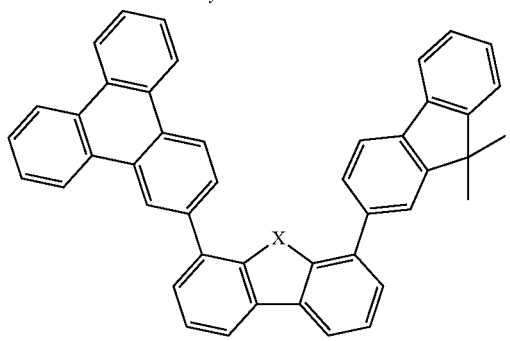

where in Compound H25: X = O,
in Compound H26, X = S, and
in Compound H27, X = Se, and Compounds H28 through H30, each represented by the formula:

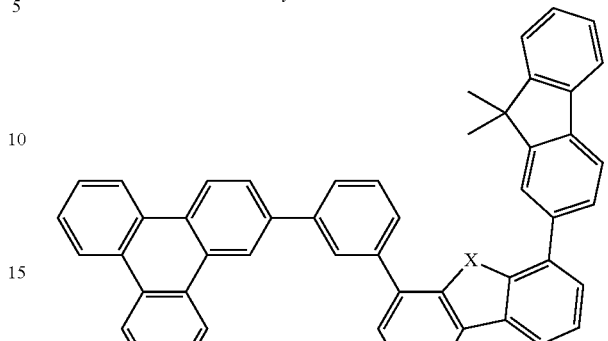

where in Compound H28: X = O,
in Compound H29, X = S, and
in Compound H30, X = Se.

18. The composition of claim 16, wherein the composition is selected from the group consisting of:

| Compositions | First compound | Second compound |
|---|---|---|
| CP1 | Compound 2 | Compound H2 |
| CP2 | Compound 2 | Compound H5 |
| CP3 | Compound 2 | Compound H8 |
| CP4 | Compound 2 | Compound H17 |
| CP5 | Compound 2 | Compound H26 |
| CP6 | Compound 5 | Compound H11 |
| CP7 | Compound 5 | Compound H14 |
| CP8 | Compound 5 | Compound H29 |
| CP9 | Compound 65 | Compound H2 |
| CP10 | Compound 65 | Compound H5. |

19. The composition of claim 16, wherein the first compound has an evaporation temperature T1 of 150 to 350° C.; wherein the second compound has an evaporation temperature T2 of 150 to 350° C.; wherein absolute value of T1-T2 is less than 20° C.; wherein the first compound has a concentration C1 in said mixture and a concentration C2 in a film formed by evaporating the mixture in a vacuum deposition tool at a constant pressure between $1 \times 10^{-6}$ Torr to $1 \times 10^{-9}$ Torr, at a 2 Å/sec deposition rate on a surface positioned at a predefined distance away from the mixture being evaporated; and
wherein absolute value of (C1−C2)/C1 is less than 5%.

20. The composition of claim 16, wherein the first compound has a first mass loss rate and the second compound has a second mass loss rate, wherein the ratio between the first mass loss rate and the second mass loss rate is within the range of 0.90 to 1.10.

* * * * *